US010575765B2

(12) United States Patent
Brill

(10) Patent No.: US 10,575,765 B2
(45) Date of Patent: Mar. 3, 2020

(54) ANALYTE-SENSING DEVICE

(71) Applicant: GLUSENSE LTD., Rehovot (IL)

(72) Inventor: Boaz Brill, Rehovot (IL)

(73) Assignee: GLUSENSE LTD., Rehovot (IL)

( * ) Notice: Subject to any disclaimer, the term of this patent is extended or adjusted under 35 U.S.C. 154(b) by 345 days.

(21) Appl. No.: 15/517,318

(22) PCT Filed: Oct. 13, 2015

(86) PCT No.: PCT/IL2015/051022
§ 371 (c)(1),
(2) Date: Apr. 6, 2017

(87) PCT Pub. No.: WO2016/059635
PCT Pub. Date: Apr. 21, 2016

(65) Prior Publication Data
US 2017/0303838 A1 Oct. 26, 2017

Related U.S. Application Data

(60) Provisional application No. 62/063,211, filed on Oct. 13, 2014.

(51) Int. Cl.
*A61B 5/1455* (2006.01)
*A61B 5/145* (2006.01)
(Continued)

(52) U.S. Cl.
CPC ........ *A61B 5/14556* (2013.01); *A61B 5/0071* (2013.01); *A61B 5/1459* (2013.01);
(Continued)

(58) Field of Classification Search
CPC .............. A61B 5/14556; A61B 5/0071; A61B 5/14532; A61B 5/1459; G01N 21/6428; G01N 21/6456; G01N 2201/021
See application file for complete search history.

(56) References Cited

U.S. PATENT DOCUMENTS

| 3,486,506 A | 12/1969 | Auphan |
| 3,554,199 A | 1/1971 | Auphan |

(Continued)

FOREIGN PATENT DOCUMENTS

| AU | 2011253785 | 1/2012 |
| EP | 1645243 | 12/2007 |

(Continued)

OTHER PUBLICATIONS

DexCom, Suimmary of Safety and Effectiveness Data, 2006 (Year: 2006).*

(Continued)

*Primary Examiner* — Eric F Winakur
*Assistant Examiner* — Marjan Fardanesh
(74) *Attorney, Agent, or Firm* — Sughrue Mion, PLLC

(57) ABSTRACT

An implantable unit includes fluorescent sensor molecules, each of which includes a binding site for an analyte, a donor fluorophore, and an acceptor fluorophore; and a first light source. An external system includes an external reading unit, which includes a light sensor; and a processor, which is configured to (i) during a first time period: (a) drive the first light source to generate light having a first illumination peak wavelength appropriate for excitation of the donor fluorophore, and (b) receive, from the light sensor, a first measurement of the fluorescent light emitted from the acceptor fluorophore, (ii) during a second time period: (a) drive a second light source to generate light having a second illumination peak wavelength appropriate for direct excitation of the acceptor fluorophore, and (b) receive, from the light sensor, a second measurement of the fluorescent light emitted from the acceptor fluorophore, and (iii) calculate the concentration of the analyte based on the measurements.

18 Claims, 11 Drawing Sheets

(51) Int. Cl.
*A61B 5/00* (2006.01)
*A61B 5/1459* (2006.01)
*G01N 21/64* (2006.01)

(52) U.S. Cl.
CPC ..... *A61B 5/14532* (2013.01); *G01N 21/6428* (2013.01); *G01N 21/6456* (2013.01); *G01N 2201/021* (2013.01)

(56) References Cited

U.S. PATENT DOCUMENTS

| | | |
|---|---|---|
| 3,774,243 A | 11/1973 | Ng et al. |
| 3,826,265 A | 7/1974 | Giori et al. |
| 3,837,339 A | 9/1974 | Aisenberg et al. |
| 3,837,922 A | 9/1974 | Ng et al. |
| 3,861,397 A | 1/1975 | Rao et al. |
| 4,140,963 A | 2/1979 | Rao et al. |
| 4,344,438 A | 8/1982 | Schultz |
| 4,352,883 A | 10/1982 | Lim |
| 4,402,694 A | 9/1983 | Ash et al. |
| 4,453,537 A | 6/1984 | Spitzer |
| 4,578,323 A | 3/1986 | Hertl et al. |
| 4,631,053 A | 12/1986 | Taheri |
| 4,661,107 A | 4/1987 | Fink |
| 4,721,677 A | 1/1988 | Clark, Jr. |
| 4,745,279 A | 5/1988 | Karkar et al. |
| 4,801,291 A | 1/1989 | Loori |
| 4,953,976 A | 9/1990 | Adler-Golden et al. |
| 4,981,779 A | 1/1991 | Wagner |
| 5,001,054 A | 3/1991 | Wagner |
| 5,011,472 A | 4/1991 | Aebischer et al. |
| 5,029,579 A | 7/1991 | Trammell |
| 5,089,697 A | 2/1992 | Prohaska |
| 5,101,814 A | 4/1992 | Palti |
| 5,116,494 A | 5/1992 | Chick et al. |
| 5,143,066 A | 9/1992 | Komives et al. |
| 5,209,231 A | 5/1993 | Cote et al. |
| 5,246,867 A | 9/1993 | Lakowicz et al. |
| 5,262,055 A | 11/1993 | Bae |
| 5,336,209 A | 8/1994 | Porzilli |
| 5,368,028 A | 11/1994 | Palti |
| 5,372,135 A | 12/1994 | Mendelson et al. |
| 5,373,855 A | 12/1994 | Skrabal et al. |
| 5,381,075 A | 1/1995 | Jordan |
| 5,387,522 A | 2/1995 | Vasington |
| 5,407,685 A | 4/1995 | Malchesky |
| 5,427,935 A | 6/1995 | Wang et al. |
| 5,431,694 A | 7/1995 | Snaper et al. |
| 5,443,504 A | 8/1995 | Hill |
| 5,443,508 A | 8/1995 | Giampapa |
| 5,512,474 A | 4/1996 | Clapper et al. |
| 5,529,066 A | 6/1996 | Palti |
| 5,545,191 A | 8/1996 | Mann et al. |
| 5,578,022 A | 11/1996 | Scherson |
| 5,614,378 A | 3/1997 | Yang et al. |
| 5,626,134 A | 5/1997 | Zuckerman |
| 5,660,940 A | 8/1997 | Larsson et al. |
| 5,662,625 A | 9/1997 | Geary, Jr. |
| 5,702,444 A | 12/1997 | Struthers et al. |
| 5,713,888 A | 2/1998 | Neuenfeldt |
| 5,741,334 A | 4/1998 | Mullon et al. |
| 5,770,454 A | 6/1998 | Essenpreis et al. |
| 5,788,682 A | 8/1998 | Maget |
| 5,792,090 A | 8/1998 | Ladin |
| 5,833,603 A | 11/1998 | Kovacs et al. |
| 5,834,005 A | 11/1998 | Usala |
| 5,855,570 A | 1/1999 | Scherson |
| 5,855,613 A | 1/1999 | Antanavich et al. |
| 5,879,709 A | 3/1999 | Soon-Shiong et al. |
| 5,902,745 A | 5/1999 | Butler et al. |
| 5,912,005 A | 6/1999 | Lanza et al. |
| 5,998,204 A | 12/1999 | Tsien et al. |
| 6,000,403 A | 12/1999 | Cantwell |
| 6,049,727 A | 4/2000 | Crothall |
| 6,049,728 A | 4/2000 | Chou |
| 6,061,582 A | 5/2000 | Small et al. |
| 6,091,974 A | 7/2000 | Palti |
| 6,148,232 A | 11/2000 | Avrahami |
| 6,163,714 A | 12/2000 | Stanley et al. |
| 6,179,804 B1 | 1/2001 | Satterfield |
| 6,187,043 B1 | 2/2001 | Ledergerber |
| 6,188,477 B1 | 2/2001 | Pu et al. |
| 6,197,534 B1 | 3/2001 | Lakowicz et al. |
| 6,254,601 B1 | 7/2001 | Burbank et al. |
| 6,256,522 B1 | 7/2001 | Schultz |
| 6,268,161 B1 | 7/2001 | Han |
| 6,294,281 B1 | 9/2001 | Heller |
| 6,330,464 B1 | 12/2001 | Colvin, Jr. et al. |
| 6,349,234 B2 | 2/2002 | Pauly et al. |
| 6,368,592 B1 | 4/2002 | Colton et al. |
| 6,372,244 B1 | 4/2002 | Antanavich |
| 6,383,478 B1 | 5/2002 | Prokop |
| 6,400,974 B1 | 6/2002 | Lesho |
| 6,471,687 B2 | 10/2002 | Butler et al. |
| 6,485,703 B1 | 11/2002 | Cote et al. |
| 6,521,446 B2 | 2/2003 | Hellinga |
| 6,531,239 B2 | 3/2003 | Heller |
| 6,556,867 B1 | 4/2003 | Kohls |
| 6,577,393 B1 | 6/2003 | Potzschke et al. |
| 6,584,335 B1 | 6/2003 | Haar et al. |
| 6,587,704 B1 | 7/2003 | Fine et al. |
| 6,602,251 B2 | 8/2003 | Burbank et al. |
| 6,605,039 B2 | 8/2003 | Houben et al. |
| 6,625,479 B1 | 9/2003 | Weber et al. |
| 6,630,154 B1 | 10/2003 | Fraker et al. |
| 6,650,919 B2 | 11/2003 | Edelberg et al. |
| 6,666,821 B2 | 12/2003 | Keimel |
| 6,671,527 B2 | 12/2003 | Petersson et al. |
| 6,673,596 B1 | 1/2004 | Sayler et al. |
| RE38,525 E | 6/2004 | Stanley et al. |
| 6,764,488 B1 | 7/2004 | Burbank et al. |
| 6,766,183 B2 | 7/2004 | Walsh et al. |
| 6,767,342 B1 | 7/2004 | Cantwell |
| 6,804,544 B2 | 10/2004 | Van Antwerp et al. |
| 6,821,107 B1 | 11/2004 | Hara |
| 6,846,288 B2 | 1/2005 | Nagar et al. |
| 6,855,556 B2 | 2/2005 | Amiss et al. |
| 6,960,351 B2 | 11/2005 | Dionne |
| 6,979,088 B2 | 12/2005 | Currie |
| 6,979,290 B2 | 12/2005 | Mourlas et al. |
| 7,068,867 B2 | 6/2006 | Adoram et al. |
| 7,161,679 B2 | 1/2007 | Masseschmidt et al. |
| 7,184,810 B2 | 2/2007 | Caduff et al. |
| 7,208,286 B2 | 4/2007 | Simpson et al. |
| 7,223,279 B2 | 5/2007 | Burbank et al. |
| 7,259,906 B1 | 8/2007 | Islam |
| 7,325,546 B2 | 2/2008 | Burbank et al. |
| 7,489,402 B2 | 2/2009 | Selker et al. |
| 7,729,767 B2 | 6/2010 | Baker et al. |
| 7,771,357 B2 | 8/2010 | Burbank et al. |
| 7,775,975 B2 | 8/2010 | Brister et al. |
| 7,863,038 B2 | 1/2011 | Motamedi et al. |
| 7,892,222 B2 | 2/2011 | Vardi et al. |
| 7,951,357 B2 | 5/2011 | Gross et al. |
| 7,964,390 B2 | 6/2011 | Rozakis et al. |
| 8,012,500 B2 | 9/2011 | Rotem |
| 8,043,271 B2 | 10/2011 | Stern |
| 8,088,595 B2 | 1/2012 | They et al. |
| 8,204,565 B2 | 6/2012 | Arnold et al. |
| 8,444,630 B2 | 5/2013 | Rotem |
| 8,700,115 B2 | 4/2014 | Markle et al. |
| 8,738,107 B2 | 5/2014 | Markle et al. |
| 9,037,205 B2 | 5/2015 | Gil et al. |
| 9,737,245 B2 | 8/2017 | Besling |
| 2002/0016535 A1 | 2/2002 | Martin et al. |
| 2002/0025469 A1 | 2/2002 | Heller |
| 2002/0038083 A1 | 3/2002 | Houben et al. |
| 2002/0072657 A1 | 6/2002 | Bousquet et al. |
| 2002/0120186 A1 | 8/2002 | Keimel |
| 2002/0193672 A1 | 12/2002 | Walsh et al. |
| 2003/0050622 A1 | 3/2003 | Humes |
| 2003/0087427 A1 | 5/2003 | Colton et al. |
| 2003/0113302 A1 | 6/2003 | Revazova |
| 2003/0117629 A1 | 6/2003 | Messerschmidt et al. |

(56) References Cited

U.S. PATENT DOCUMENTS

| | | |
|---|---|---|
| 2003/0134346 A1 | 7/2003 | Amiss et al. |
| 2003/0216759 A1 | 11/2003 | Burbank et al. |
| 2003/0227681 A1 | 12/2003 | Currie |
| 2003/0232370 A1 | 12/2003 | Trifiro |
| 2004/0091757 A1 | 5/2004 | Wang et al. |
| 2004/0097788 A1 | 5/2004 | Mourlas et al. |
| 2004/0109302 A1 | 6/2004 | Yoneda et al. |
| 2004/0111018 A1 | 6/2004 | Isenberg et al. |
| 2004/0133188 A1 | 7/2004 | Vardi et al. |
| 2004/0199059 A1 | 10/2004 | Brauker et al. |
| 2004/0199062 A1* | 10/2004 | Petersson ............ A61B 5/14532 600/316 |
| 2004/0259270 A1 | 12/2004 | Wolf |
| 2005/0025680 A1 | 2/2005 | Monzyk |
| 2005/0027332 A1 | 2/2005 | Avrahami et al. |
| 2005/0054100 A1 | 3/2005 | Rennard et al. |
| 2005/0085868 A1 | 4/2005 | Tehrani et al. |
| 2005/0095174 A1 | 5/2005 | Wolf |
| 2005/0096516 A1 | 5/2005 | Soykan et al. |
| 2005/0113852 A1 | 5/2005 | Burbank et al. |
| 2005/0118726 A1 | 6/2005 | Schultz et al. |
| 2005/0136092 A1 | 6/2005 | Rotem |
| 2005/0211572 A1 | 9/2005 | Buck et al. |
| 2005/0221072 A1 | 10/2005 | Dubrow et al. |
| 2005/0221276 A1 | 10/2005 | Rozakis et al. |
| 2005/0267326 A1 | 12/2005 | Loeb et al. |
| 2006/0000479 A9 | 1/2006 | Burbank et al. |
| 2006/0063140 A1 | 3/2006 | Nussinovitch |
| 2006/0184206 A1 | 8/2006 | Baker et al. |
| 2006/0241365 A1 | 10/2006 | Botvinick et al. |
| 2007/0003994 A1 | 1/2007 | Simpson |
| 2007/0004974 A1 | 1/2007 | Nagar et al. |
| 2007/0066877 A1 | 3/2007 | Arnold et al. |
| 2007/0190038 A1 | 8/2007 | Suzuki |
| 2008/0086042 A1 | 4/2008 | Brister |
| 2008/0166329 A1 | 7/2008 | Sung et al. |
| 2008/0188722 A1 | 8/2008 | Markle et al. |
| 2008/0262567 A1 | 10/2008 | Avrahami et al. |
| 2008/0287776 A1 | 11/2008 | Ephrath et al. |
| 2008/0319287 A1 | 12/2008 | Gross et al. |
| 2009/0012502 A1 | 1/2009 | Rotem |
| 2009/0178459 A1 | 7/2009 | Li et al. |
| 2009/0192493 A1 | 7/2009 | Meng et al. |
| 2009/0287060 A1 | 11/2009 | Pell et al. |
| 2010/0015709 A1 | 1/2010 | Rehfeldt et al. |
| 2010/0037329 A1 | 2/2010 | Frommer et al. |
| 2010/0047311 A1 | 2/2010 | Rotem |
| 2010/0145317 A1 | 6/2010 | Laster et al. |
| 2010/0160749 A1 | 6/2010 | Gross et al. |
| 2010/0202966 A1 | 8/2010 | Gross et al. |
| 2010/0312165 A1 | 12/2010 | Stern |
| 2010/0312483 A1* | 12/2010 | Peyser .................. G01N 33/52 702/19 |
| 2011/0165219 A1 | 7/2011 | Barkai et al. |
| 2011/0190679 A1 | 8/2011 | Humes et al. |
| 2011/0251471 A1 | 10/2011 | Gross et al. |
| 2012/0059232 A1 | 3/2012 | Gross et al. |
| 2012/0113997 A1 | 5/2012 | Islam |
| 2012/0290043 A1 | 11/2012 | Gross |
| 2013/0006069 A1 | 1/2013 | Gil et al. |
| 2013/0116664 A1 | 5/2013 | Tai et al. |
| 2013/0331667 A1 | 12/2013 | Colvin, Jr. et al. |
| 2014/0018644 A1 | 1/2014 | Colvin, Jr. et al. |
| 2014/0088383 A1 | 3/2014 | Colvin, Jr. et al. |
| 2014/0128694 A1* | 5/2014 | Gallant ................. A61B 5/1459 600/316 |
| 2014/0187878 A1 | 7/2014 | Emken et al. |
| 2015/0343093 A1 | 12/2015 | Gladnikoff et al. |
| 2015/0352229 A1 | 12/2015 | Brill et al. |
| 2016/0324449 A1 | 11/2016 | Brill et al. |
| 2017/0100598 A1 | 4/2017 | Brill et al. |

FOREIGN PATENT DOCUMENTS

| | | |
|---|---|---|
| EP | 2196795 A1 | 6/2010 |
| GB | 2024012 | 1/1980 |
| WO | 90/15526 | 12/1990 |
| WO | 91/01680 | 2/1991 |
| WO | 91/09312 | 6/1991 |
| WO | 1992/019195 | 11/1992 |
| WO | 1994/000602 | 1/1994 |
| WO | 1994/020076 | 9/1994 |
| WO | 96/00106 | 1/1996 |
| WO | 98/54294 | 12/1998 |
| WO | 98/55869 | 12/1998 |
| WO | 2000/078920 | 12/2000 |
| WO | 01/50983 | 7/2001 |
| WO | 03/011445 | 2/2003 |
| WO | 03/025220 | 3/2003 |
| WO | 04/028358 | 4/2004 |
| WO | 04/051774 | 6/2004 |
| WO | 04/089465 | 10/2004 |
| WO | 2005/002467 | 1/2005 |
| WO | 2005/033659 | 4/2005 |
| WO | 05/053523 | 6/2005 |
| WO | 01351623 | 6/2005 |
| WO | 06/006166 | 1/2006 |
| WO | 2006/044612 | 4/2006 |
| WO | 2006/059322 | 6/2006 |
| WO | 06/097933 | 9/2006 |
| WO | 07/110867 | 10/2007 |
| WO | 08/018079 | 2/2008 |
| WO | 2008/062417 | 5/2008 |
| WO | 2008/065660 | 6/2008 |
| WO | 2008/079997 | 7/2008 |
| WO | 2009/031154 | 3/2009 |
| WO | 2009/039207 | 3/2009 |
| WO | 2009/140757 | 11/2009 |
| WO | 2010/032242 | 3/2010 |
| WO | 2010/061387 | 6/2010 |
| WO | 2010/073249 | 7/2010 |
| WO | 2010/089739 | 8/2010 |
| WO | 2011/072401 | 6/2011 |
| WO | 2013/001532 | 1/2013 |
| WO | 2013/155553 | 10/2013 |
| WO | 2014/102743 | 7/2014 |
| WO | 2015/128826 | 9/2015 |
| WO | 2016/059635 | 4/2016 |
| WO | 2017/183030 | 10/2017 |

OTHER PUBLICATIONS

An International Preliminary Report on Patentability dated Jun. 29, 2011 which issued during the prosecution of Applicant's PCT/IL 09/01214.

An International Search Report and a Written Opinion both dated Jul. 1, 2010 which issued during the prosecution of Applicant's PCT/IL 09/01214.

U.S. Appl. No. 61/746,691, filed Dec. 28, 2012.

An International Preliminary Report on Patentability dated Mar. 24, 2009 which issued during the prosecution of Applicant's PCT/IL2005/000743.

Written Opinion dated Mar. 20, 2009 which issued during the prosecution of Applicant's PCT/IL2005/000743.

An International Search Report dated May 7, 2009 which issued during the prosecution of Applicant's PCT/IL2005/000743.

European Search Report dated Dec. 16, 2009, which issued during the prosecution of Applicant's European Patent Application No. EP 05 75 8905.

A Supplementary European Search Report dated Mar. 3, 2010 which issued during the prosecution of Applicant's European Patent Application No. 05758905.3.

An International Search Report dated Jan. 24, 2008 which issued during the prosecution of Applicant's PCT/IL2007/000399.

An International Preliminary Report on Patentability together with Written Opinion dated Sep. 30, 2008 which issued during the prosecution of Applicant's PCT/IL2007/000399.

(56) References Cited

OTHER PUBLICATIONS

An Office Action dated Jan. 13, 2012, which issued during the prosecution of European Patent Application No. 05758905.3.
An Office Action dated Sep. 23, 2011 which issued during the prosecution of U.S. Appl. No. 12/225,749.
A Supplementary European Search Report dated Feb. 4, 2010 which issued during the prosecution of Applicant's European Patent Application No. 07736139.2.
An Office Action dated Oct. 3, 2012, which issued during the prosecution of U.S. Appl. No. 12/344,103.
An Office Action dated Nov. 16, 2011 which issued during the prosecution of European Patent Application No. 07736139.2.
U.S. Appl. No. 60/820,130, filed Jul. 24, 2006.
U.S. Appl. No. 60/658,716, filed Mar. 3, 2005.
U.S. Appl. No. 60/588,211, filed Jul. 14, 2004.
Wan Q, "Dual wavelength polarimetry for monitoring glucose in the presence of varying birefringence," A thesis submitted to the Office of Graduate Studies of Texas A&M University (2004).
Klueh U. et al., entitled, "Enhancement of implantable glucose sensor function in vivo using gene transfer-induced neovascularization," Biomaterials, Apr. 2005, 26(10):1155-63.
An Office Action dated Feb. 2, 2012, which issued during the prosecution of U.S. Appl. No. 12/225,749.
Yu-Lung L et al., "A polarimetric glucose sensor using a liquid-crystal polarization modulator driven by a sinusoidal signal," Optics Communications 259(1), pp. 40-48 (2006).
Olesberg JT et al., "Tunable Laser Diode System for Noninvasive Blood Glucose Measurements," Appl. Spectrosc. 59, pp. 1480-1484 (2005).
Olesberg JT et al., "In vivo near-infrared spectroscopy of rat skin tissue with varying blood glucose levels," Analytical Chemistry 78, pp. 215-223 (2006).
Ye K et al., "Genetic engineering of an allosterically based glucose indicator protein for continuous glucose monitoring by fluorescence resonance energy transfer," Analytical Chemistry, 2003, 75(14), 3451-3459.
Fillat C et al., "Suicide gene therapy mediated by the herpes simplex virus thymidine kinase gene / ganciclovir system: Fifteen years of application," Current Gene Therapy, 3(1), pp. 13-26, (Feb. 2003).
Scognamiglio V et al., "Protein-based biosensors for diabetic patients," Journal of Fluorescence, 14(5), 491-498 (Sep. 2004).
Moschou E et al., "Fluorescence glucose detection: Advances toward the ideal in vivo biosensor," Journal of Fluorescence, 14(5), 535-547 (Sep. 2004).
Reszka R et al., "Liposome-mediated suicide gene therapy in humans," Methods in Enzymology, 391, 200-208 (2005).
Deuschle K et al., "Construction and optimization of a family of genetically encoded metabolite sensors by semirational protein engineering," Protein Sci. 14: 2304-2314 (2005).
Yonzon CR et al., "A glucose biosensor based on surface-enhanced Raman scattering: Improved partition layer, temporal stability, reversibility, and resistance to serum protein interference," Anal. Chem., 76 (1), pp. 78-85 2004.
Liua L et al., "Glucose permeable poly (dimethyl siloxane) poly (N-isopropyl acrylamide) interpenetrating networks as ophthalmic biomaterials," Biomaterials vol. 26, Issue 3 pp. 233-244 (2005).
Yokota M et al., "A compact polarimetric glucose sensor using a high-performance fibre-optic Faraday rotator," Meas. Sci. Technol. 15 pp. 143-147 (2004).
McNichols J et al., "Development of a non-invasive polarimetric glucose sensor," IEEE-LEOS Newsletter, 12:30-31 (1998).
Olesberg JT, "Noninvasive blood glucose monitoring in the 2.0-2.5 μm wavelength range," Lasers and Electro-Optics Society. LEOS 2001. The 14th Annual Meeting of the IEEE. vol. 2, p. 529.
Dvir D et al., "Non invasive blood glucose monitoring in the critically ill patients," European Society for Clinical Nutrition and Metabolism Congress, Istanbul (2006)—an abstract.
Koo TW et al., "Measurement of glucose in human blood serum using Raman spectroscopy", IEEE-LEOS Newsletter 12(2) 18 (1998).
Amir O. et al., "Accurate home and clinical use of a non-invasive continuous glucose monitor," (2006)—an abstract.
H.P. Bennetto, "Electricity generation by microorganisms", Biotech. Educ. vol. 1, No. 4, pp. 163-168, 1990.
K. Yamada, et al., "Measurement of glucose uptake and intracellular calcium concentration in single, living pancreatic β-cells", The Journal of Biological Chemistry, vol. 275, No. 29, Jul. 2000, pp. 22278-22283.
P. Turkewitsch, "The synthesis of fluorescent chemosensors responsive to cAMP and other nucleotides", Montreal Quebec, Sep. 1998.
G. Gilardi, et al., "Spectroscopic properties of an engineered maltose binding protein", Protein Engineering vol. 10 No. 5, pp. 479-486, 1997.
Hellinga Homme W.et al., "Protein engineering and the development of generic biosensors", TIBTECH Apr. 1998, vol. 16.
Higson S.P.J. et al., "Biosensors: a viable monitoring technology?", Med. & Biol. Eng. & Comput., 1994, 32, 601-609.
Tolosa Leah et al., "Optical assay for glucose based on the luminescnence decay time of the long wavelength dye Cy5™", Sensors and Actuators B 45 (1997) 93-99.
Tolosa Leah et al., "Glucose sensor for low-cost lifetime-based sensing using a genetically engineered protein", Analytical Biochemistry 267, 114-120 (1999).
J.C. Pickup, et al., "Fluorescence-based glucose sensors", Biosensors and Bioelectronics 20 (2005) 2555-2565.
Sakurada M et al., "Relation between glucose-stimulated insulin secretion and intracellular calcium accumulation studied with a superfusion system of a glucose-responsive pancreatic β-cell line MIN6", Endo. 1993, vol. 132, No. 6.
Tsujimura, et al., "Photosynthetic bioelectrochemical cell utilizing cyanobacteria and water-generating oxidase", Enzyme and Microbial Tech. 29 (2001) 225-231.
Deuschle, et al., "Genetically encoded sensors for metabolities", Cytometry A. Mar. 2005;64(1):3-9.
Serganova, et al., "Reporter gene imaging: potential impact on therapy", Nucl Med Biol. Oct. 2005;32(7):763-80.
Laxman, et al., "Noninvasive real-time imaging of apoptosis", Proc Natl Acad Sci USA Dec. 24, 2002;99(26):16551-5.
Fehr, et al., "In vivo imaging of the dynamics of glucose uptake in the cytosol of COS-7 cells by fluorescent nanosensors", J Biol Chem. May 23, 2003;278(21):19127-33.
Fehr, et al., "Minimally invasive dynamic imaging of ions and metabolites in living cells", Curr Opin Plant Biol. Jun. 2004;7(3):345-51.
Philippe et al., "Vaginal ligature of uterine arteries during postpartum hemorrhage", International Journal of Gynecology & Obstetrics 56 (1997) 267-270.
Tolosa Leah et al., "Lifetime-based sensing of glucose using energy transfer with a long lifetime donor", Analytical Biochemistry 250, 102-108, 1997.
Pickup, et al., "In vivo glucose monitoring: the clinical reality and the promise", Biosens Bioelectron. Apr. 15, 2005;20(10):1897-902.
Olesberg JT et al., "Optical microsensor for continuous glucose measurements in interstitial fluid," Optical Diagnostics and Sensing VI, Proc. of SPIE vol. 6094, 609403, pp. 1605-7422 (2006).
Amir O et al., "Highly accurate non-invasive continuous glucose monitoring in clinical and home use settings," American Diabetes Association, 66th Scientific Session, Washington, D.C. (2006)—an abstract.
Patounakis G., et al., "Active CMOS array sensor for time-resolved fluorescence detection", IEEE Journal of Solid-State Circuits, vol. 41, No. 11, Nov. 2006.
Primack H, "Non-invasive sensing of glucose and hemoglobin," Optical Imaging (2006)—an abstract.
Ackland-Berglund, C et al., "Efficacy of tetracycline-controlled gene expression is influenced by cell type," BioTechniques 18, 196-200 (1995).
Amir O et al., "Evaluation of a non-invasive continuous glucose monitoring device in a home use setting," European Association for the Study of Diabetes, 42nd Annual Meeting, Copenhagen—Malmoe, Denmark—Sweden (2006)—an abstract.
Cote GL "Noninvasive and minimally-invasive optical monitoring technologies," The Journal of Nutrition 131:1596S-1604S (2001).

(56) References Cited

OTHER PUBLICATIONS

Berrebi A et al., "A non-invasive evaluation of hematocrit with a new optical sensor," European Hematology Association, 11th Congress, Amstaerdam (2006).
Kononenko A et al., "Evaluation of a non-invasive blood glucose monitoring device for critically ill patients," 26th International Symposium on Intensive Care and Emergency Medicine, Brussels (2006).
Marvin, et al., "The rational design of allosteric interactions in a monomeric protein and its applications to the construction of biosensors", Proc. Natl. Acad. Sci. USA vol. 94, pp. 4366-4371, Apr. 1997.
Communication dated Aug. 29, 2012 which issued during the prosecution of European Patent Application No. 05758905.3.
Written Opinion dated Sep. 29, 2008 which issued during the prosecution of Applicant's PCT/IL2007/000399.
An Office Action dated Aug. 26, 2014, which issued during the prosecution of U.S. Appl. No. 13/173,831.
An Office Action dated Oct. 7, 2013, which issued during the prosecution of U.S. Appl. No. 13/173,831.
U.S. Appl. No. 60/786,532, filed Mar. 28, 2006.
Jadlowiec J et al., "Bone tissue engineering: Recent advances and promising therapeutic agents", Expert opinion on Biological therapy Jan. 2003.
An Office Action dated Jan. 10, 2013 which issued during the prosecution of U.S. Appl. No. 12/225,749.
An Office Action dated Dec. 6, 2012, which issued during the prosecution of U.S. Appl. No. 12/064,946.
Notice of Allowance dated Mar. 20, 2013, which issued during the prosecution U.S. Appl. No. 12/064,946.
An Office Action dated May 14, 2012, which issued during the prosecution of U.S. Appl. No. 12/515,818.
Stagner, et al., "The pancreas as an islet transplantation site", Sep. 1, 2007, Journal of the Pancreas, vol. 8, No. 5, pp. 628-636.
T. Yagishita, S. Sawayama, K.-I. Tsukahara, and T. Ogi, "Effects of intensity of incident light and concentrations of *Synechococcus* sp. and 2-hydroxy-1,4-naphthoquinone on the current output of photosynthetic electrochemical cell," Solar Energy, vol. 61, No. 5, pp. 347-353, 1997. Abstract.
T. Yagishita, S. Sawayama, K.-I. Tsukahara, and T. Ogi, "Performance of photosynthetic celectrochemical cells using immobilized Anabaena variabilis M-3 in discharge/culture cycles," J. Ferment. Bioeng., vol. 85, No. 5, pp. 546-549, 1998. Abstract.
A. Solovev, E. Y. Katz, V. A. Shuvalov, and Y. E. Erokhin, "Photoelectrochemical effects for chemicall modified platinum electrodes with immobilized reaction centers from Rhodobacter sphaerides R-26," Bioelectrochem. Bioenerg., vol. 26, pp. 29-41, 1991. Abstract.
E. Y. Katz, and A. A. Solovev, "Photobioelectrodes on the basis of photosynthetic reaction centers. Study of exogenous quinines as possible electron transfer mediators," Anal. Chim. Acta., vol. 266, pp. 97-106, 1992. Abstract.
A. Halme, X. Zhang and N. Rintala, "Monitoring and control of a bacteria fuel cell process by colour analysis," in Proc. 7th Int. Conf. Computer Applications on Biotechnology, Osaka, Japan, May 31-Jun. 4, 1998, pp. 467-462.
An International Search Report dated Apr. 17, 2001, which issued during the prosecution of Applicant's PCT/IL01/00031.
An International Preliminary Report on Patentability dated Jul. 12, 2003, which issued during the prosecution of Applicant's PCT/IL/00031.
A Restriction Requirement dated Nov. 2, 2006, which issued during the prosecution of U.S. Appl. No. 10/466,069.
An International Search Report and a Written Opinion both dated Jun. 9, 2010, which issued during the prosecution of Applicant's PCT/IL2009/001114.
An International Preliminary Report on Patentability dated May 31, 2011, which issued during the prosecution of Applicant's PCT/IL2009/001114.

An English Translation of an Office Action dated Dec. 8, 2011, which issued during the prosecution of Chinese Patent Application No. 200580047325.4.
An Office Action dated Jan. 23, 2009, which issued during the prosecution of U.S. Appl. No. 10/466,069.
An Office Action dated Jun. 22, 2010, which issued during the prosecution of U.S. Appl. No. 10/466,069.
Notice of Allowance dated Oct. 28, 2010, which issued during the prosecution of U.S. Appl. No. 10/466,069.
An International Search Report and a Written Opinion both dated Oct. 1, 2008, which issued during the prosecution of Applicant's PCT/IL2007/001471.
An International Preliminary Report on Patentability dated Jun. 3, 2009, which issued during the prosecution of Applicant's PCT/IL2007/001471.
An International Search Report and a Written Opinion both dated May 11, 2006, which issued during the prosecution of Applicant's PCT/IL2005/001262.
An International Preliminary Report on Patentability dated Jun. 5, 2007, which issued during the prosecution of Applicant's PCT/IL2005/001262.
Partial International Search Report dated Mar. 24, 2014, which issued during the prosecution of Applicant's PCT/IB2013/061368.
An International Search Report and a Written Opinion both dated Jun. 12, 2014, which issued during the prosecution of Applicant's PCT/IB2013/061368.
An Office Action dated Aug. 26, 2013, which issued during the prosecution of U.S. Appl. No. 12/344,103.
An English Translation of an Office Action dated Mar. 3, 2014, which issued during the prosecution of Chinese Patent Application No. 200980157599.7.
An English Translation of an Office Action dated Mar. 10, 2014, which issued during the prosecution of Chinese Patent Application No. 200980157599.7.
European Search Report dated Apr. 15, 2013, which issued during the prosecution of Applicant's European App No. 09834227.2.
Communication dated Feb. 26, 2013, which issued during the prosecution of EP Patent Application No. 07736139.2.
An International Search Report and a Written Opinion both dated Nov. 21, 2012, which issued during the prosecution of Applicant's PCT/IL2012/000268.
An English Translation of an Office Action dated Apr. 12, 2013 which issued during the prosecution of Chinese Patent Application No. 200980157599.
A European Search Report and communication dated Oct. 31, 2012, which issued during the prosecution of EP Patent Application No. 12 15 9273.
U.S. Appl. No. 62/258,783, filed Nov. 23, 2015.
An International Search Report and a Written Opinion both dated Apr. 1, 2016, which issued during the prosecution of Applicant's PCT/IL2015/051022.
An Office Action dated Jul. 2, 2014, which issued during the prosecution of U.S. Appl. No. 13/141,936.
An Office Action dated Jan. 22, 2015, which issued during the prosecution of U.S. Appl. No. 13/141,936.
An Office Action dated Aug. 26, 2013, which issued during the prosecution of U.S. Appl. No. 13/141,936.
Wu H et al., In "In situ electrochemical oxygen generation with an immunoisolation device," Ann N Y Acad Sci 875:105-25 (1999).
Khamsi R, , "Microbes Pass Valuable Gas," Wired News, May 20, 2003.
Parikh et al., "Role of Spirulina in the control of glycemia and lipidemia in type 2 diabetes mellitus," J Med Food 2001, Winter 4(4): 193-199.
Katz E et al., "Biochemical fuel cells," Chapter 21 of Handbook of Fuel Cells—Fundamentals, Technology and Applications, Vielstich W et al, eds., vol. 1: Fundamentals and Survey of Systems, John Wiley & Sons (2003).
Haselkorn A, "Microbial fuel cells to power future: new design promises medical breakthroughs," The Daily Californian Online, Aug. 28, 2002.

(56) References Cited

OTHER PUBLICATIONS

Pescovitz D, "Body battery," Lab Notes—Research from the College of Engineering, University of California, Berkeley, vol. 2, Issue 6 (Aug. 2002).

K. B. Lam, E. Johnson, and L. Lin, "A Bio-Solar Cell Powered by Sub-Cellular Plant Photosystems," in Proc. IEEE Conf. on Micro Electro Mechanical Syst.(MEMS 2004), Maastricht, The Netherlands, Jan. 25-29, 2004, pp. 220-223.Abstract.

E. Y. Katz, A. Y. Shkuropatov, and V. A. Shuvalov, "Electrochemical approach to the development of a photoelectrode on the basis of photosynthetic reaction centers," Bioelectrochem. Bioenerg., vol. 23, pp. 239-247, 1990. Abstract.

N. Mano, F. Mao, and A. Heller, "Characteristics of a miniature compartment-less glucose-O2 biofuel cell and its operation in a living plant," J. Am. Chem. Soc., vol. 125, No. 21, pp. 6588-6594, 2003. Abstract.

M. Chiao, K. B. Lam, Y.-C. Su, and L. Lin, "A Miniaturized Microbial Fuel Cell," Technical Digest of Solid-State Sensors and Actuators Workshop, Hilton Head Island, Jun. 2002, pp. 59-60.

M. Chiao, K. B. Lam, and L. Lin, "A micromachined microbial fuel cell," in Proc. IEEE Conf. on Micro Electro Mechanical Syst. (MEMS 2003), Kyoto, Japan, Jan. 19-23, 2003, pp. 383-386. Abstract.

E. Y. Katz, A. Y. Shkuropatov, O. I. Vagabova, and V. A. Shuvalov, "Coupling of photoinduced charge separation in reaction centers of photosynthetic bacteria with electron-transfer to a chemically modified electrode," Biochima et Biophysica Acta., vol. 976, pp. 121-128, 1989.

X. Zhang and A. Halme, "Modelling of a microbial fuel cell process," Biotechnology Letters, vol. 17, No. 8, pp. 809-814, 1995. Abstract.

Lam KB et al, "A micro photosynthetic electrochemical cell," Micro Electro Mechanical Systems, 2003. MEMS-03 Kyoto. IEEE the Sixteenth Annual International Conference on, pp. 391-394 (ISSN: 1084-6999) (Jan. 19-23, 2003). Abstract.

T. Yagishita, T. Horigome, "Effects of light, CO2, and inhibitors on the current output of biofuel cells containing the photosynthetic organism *Synechococcus* sp.," J. Chem. Tech. Biotech, vol. 56, No. 4, pp. 393-399, 1993. Abstract.

T. Yagishita, T. Horigome, K. Tanaka, "Biofuel-cells containing photosynthetic microorganisms," J. Electrochem. Soc. Japan, vol. 61, No. 6, pp. 687-688, 1993. Abstract.

T. Yagishita, S. Sawayama, K.-I. Tsukahara, and T. Ogi, "Effects of glucose addition and light on current outputs in photosynthetic electrochemical cells using *Synechocystis* sp. PCC6714," J. Biosci. Bioeng., vol. 99, No. 2, pp. 210-214, 1999 Abstract.

R. M. Allen and H. P. Bennetto, "Microbial fuel cells: electricity production from carbohydrates," Appl. Biochem. Biotech., vol. 39/40, pp. 27-40, 1993. Abstract.

Notice of Allowance dated Jan. 20, 2011, which issued during the prosecution of U.S. Appl. No. 11/632,587.

An Office Action dated Nov. 28, 2011, which issued during the prosecution of U.S. Appl. No. 12/064,946.

An Office Action dated Apr. 24, 2012, which issued during the prosecution of U.S. Appl. No. 12/064,946.

An Office Action dated Jul. 26, 2012, which issued during the prosecution of European Patent Application No. 05812146.

A Supplementary European Search Report dated Jul. 26, 2012, which issued during the prosecution of Applicant's European Patent Application No. 05812146.

An International Search Report and a Written Opinion both dated Oct. 1, 2008, which issued during the prosecution of Applicant's PCT/IL2007/001447.

An International Search Report and a Written Opinion both dated Jan. 25, 2012 which issued during the prosecution of Applicant's PCT/IL2011/000445.

An English Translation of an Office Action dated Mar. 2, 2012, which issued during the prosecution of Japanese Patent Application No. 2007-544006.

An English Translation of an Office Action dated May 31, 2011, which issued during the prosecution of Japanese Patent Application No. 2007-544006.

Yun Jung Heo et al., "Towards Smart Tattoos: Implantable Biosensors for Continuous Glucose Monitoring" Adv. Healthcare Mater. 2013, 2, 43-56.

Beningo et al. Double-Hydrogel Substrate as a Model System for Three-Dimensional Cell Culture; Methods in Cell Biology, vol. 370; Adhesion Protein Protocols, 2nd Ed. (2007) pp. 203-211.

An International Search Report and a Written Opinion both dated Jan. 25, 2010, which issued during the prosecution of Applicant's PCT/IL2009/000905.

An Office Action dated May 14, 2010, which issued during the prosecution of U.S. Appl. No. 12/315,102.

An Office Action dated Jan. 7, 2011, which issued during the prosecution of U.S. Appl. No. 11/001,556.

Faithful, N. S. Anaesthesia, 42, pp. 234-242 (1987).

Lacy PE et al., "Maintenance of normoglycemia in diabetic mice by subcutaneous xenografts of encapsulated islets," Science 1782-4 (1991).

T. Akiba, H. P. Bennetto, J. L. Stirling, and K. Tanaka, "Electricity production from alkalophilic organisms," Biotechnol., vol. 9, No. 9, 611-616, 1987. Abstract.

Kaisers U et al., "Liquid ventilation," British Journal of Anaesthesia 91 (1) : 143-151 (2003).

Steve Barash et al., "Human secretor signal peptide description by hidden Markov model and generation of a strong artificial signal peptide for secreted protein expression", Biochemical and Biophysical Research Communications 294 (May 15, 2002) 835-842.

"Membrane,", Merriam-Webster.com. Merriam-Webster, n.d. Web. Sep. 29, 2016.

An Office Action dated Jun. 11, 2015, which issued during the prosecution of U.S. Appl. No. 12/225,749.

An Office Action dated Dec. 9, 2014, which issued during the prosecution of U.S. Appl. No. 12/225,749.

An Office Action dated Sep. 7, 2007, which issued during the prosecution of U.S. Appl. No. 10/466,069.

A Notice of Allowance dated Jun. 10, 2013, which issued during the prosecution of U.S. Appl. No. 13/356,053.

Partial International Search Report dated May 27, 2015, which issued during the prosecution of Applicant's PCT/IB2015/051427.

An Office Action dated Jun. 17, 2014, which issued during the prosecution of U.S. Appl. No. 13/089,096.

An Office Action dated Mar. 13, 2015, which issued during the prosecution of U.S. Appl. No. 13/089,096.

An Office Action dated Oct. 23, 2014, which issued during the prosecution of U.S. Appl. No. 13/089,096.

Jithesh V. Veetil et al. "A Glucose Sensor Protein for Continuous Glucose Monitoring" Biosens Bioelectron. Dec. 15, 2010; 26(4): 1650-1655. doi:10.1016/j.bios.2010.08.052.

Jonghoon Choi et al: "Interactions between mesenchymal stem cells and T cells on a single cell level a nanowell array", Nano/Molecular Medicine and Engineering (NANOMED), 2012 IEEE 6th International Conference on, IEEE, Nov. 4, 2012 (Nov. 4, 2012), pp. 111-116.

An International Search Report and a Written Opinion both dated Aug. 3, 2015, which issued during the prosecution of Applicant's PCT/IB2015/051427.

European Search Report dated Sep. 9, 2014 which issued during the prosecution of Applicant's European App No. 05758905.3.

Sha Jin et al., "Construction of a Panel of Glucose Indicator Proteins for Continuous Glucose Monitoring", Biosens Bioelectron. Apr. 15, 2011; 26(8):3427-3431. doi:10.1016/j.bios.2011.01.017.

L. Leheninger, Biochemistry, Worth Publishers, Inc. 1978, Chapter 14, pp. 363-364.

Smith AJ, "Acetate assimilation by nitrobacter agilis in relation to its 'obligate autotrophy' ", Journal of Bacteriology 95:844 (1968).

Silva AI et al., "An overview on the development of a bio-artificial pancreas as a treatment of insulin-dependent diabetes mellitus," Med Res Rev 26 (2) : 181-222 (2006).

Notice of Allowance dated Jan. 21, 2015, which issued during the prosecution of U.S. Appl. No. 13/173,831.

(56) References Cited

OTHER PUBLICATIONS

An Office Action dated Aug. 31, 2010, which issued during the prosecution of U.S. Appl. No. 11/632,587.
Communication from the European Patent Office dated May 8, 2015, which issued during the prosecution of European Patent Application No. 05758905.3.
An Office Action dated Jan. 29, 2016, which issued during the prosecution of U.S. Appl. No. 12/225,749.
An Invitation to pay additional fees dated Jan. 19, 2016, which issued during the prosecution of Applicant's PCT/IL2015/051022.
An Office Action dated Mar. 2, 2017, which issued during the prosecution of U.S. Appl. No. 14/758,493.
An Office Action dated Feb. 16, 2017: which issued during the prosecution of Chinese Patent Application No. 201380073934.1.
Pieper et al. Preparation and Characterization of Porous Crosslinked Collagenous Matrices Containing Bioavailable Chondroitin Sulphate; Biomaterials, vol. 20 (1999) pp. 847-858.
Ye et al. Studies on the Use of Hollow Fibre Membrane Bioreactors for Tissue Generation by Using Rat Bone Marrow Fibroblastic Cells and a Composite Scaffold; Journal of Material Science, Material in Medicine, vol. 18 (2007) pp. 641-648.
Kovacic et al. New Insights Into Cytosolic Glucose Levels During Differentiation of 3T3-L1 Fibroblasts Into Adipocytes; The Journal of Biological Chemistry, vol. 286, No. 15 (2011) pp. 13370-13381.
Khodjakov et al. Imaging the Division Process in Living Tissue Culture Cells; Methods, vol. 38, No. 1 (2006) pp. 1-24.
Fischer et al. Stiffness-Controlled Three-Dimensional Extracellular Matrices for High-Resolution Imaging of Cell Behavior; Nature Protocols, vol. 7, No. 11 (10/252012) pp. 2056-2066.
An Office Action dated Oct. 5, 2016, which issued during the prosecution of U.S. Appl. No. 14/758,493.
Beningo KA et al., "Flexible Polyacrylamide Substrata for the Analysis of Mechanical Interactions at CellSubstratum Adhesions," in Methods in Cell Biology, vol. 69 (2002), pp. 325-339.
Whitford et al. Interest in Hollow-Fiber Perfusion Bioreactors is Growing; BioProcess International, Oct. 2009, pp. 54-63.
An International Preliminary Report on Patentability dated Jun. 30, 2015, which issued during the prosecution of Applicant's PCT/IB2013/061368.
An International Preliminary Report on Patentability dated Aug. 30, 2016, which issued during the prosecution of Applicant's PCT/IB2015/051427.
An International Preliminary Report on Patentability dated Jan. 7, 2014, which issued during the prosecution of Applicant's PCT/IL2012/000268.
An Office Action dated Jun. 7, 2016, which issued during the prosecution of U.S. Appl. No. 14/758,493.
Vyas NK et al., "Sugar and Signal-Transducer Binding Sites of the *Escherichia-coli* Galactose Chemoreceptor Protein," 1988, Science (Washington DC), vol. 242, Nr. 4883, pp. 1290-1295.
Senseonics—EASD—Poster2 (Oct. 2012).
Steinmeyer R et al., "Improved Fluorescent Proteins for Single-Molecule Research in Molecular Tracking and Co-Localization," Journal of Fluorescence, vol. 15, No. 5, Sep. 2005.
U.S. Appl. No. 62/063,211, filed Oct. 13, 2014.
An International Search Report and a Written Opinion both dated Sep. 13, 2017, which issued during the prosecution of Applicant's PCT/IL2017/050456.
Communication dated Dec. 13, 2016, which issued during the prosecution of European Patent Application No. 13821988.6.
A second Office Action in Chinese Appl. No. 201380073934.1, dated Jan. 12, 2018.
A First Examination Report in India Appl. No. 9075/DELNP/2008, dated Jan. 31, 2018.
A non-final Office Action in U.S. Appl. No. 14/881,431, dated Mar. 9, 2018.
Joseph et al., "Pressure Sensitive Adhesives with Porosity". PSTCTech Papers, published online May 31, 2010, http://www.pstc.org/files/public/TECH33Papers/2010JosephEugene.pdf, pp. 1-6 (Year: 2010).
Ross et al., "Synthetic substrates for long-term stem cell culture". Polymer vol. 53, Issue 13, Jun. 7, 2012, pp. 2533-2539. (Year: 2012).
A Rule 164(2)(b) and Article 94(3) EPC Communication issued in European Appl. No. 15787690.5, dated May 7, 2018.
A Non-Final Office Action in U.S. Appl. No. 15/360,523, dated May 4, 2018.
Translation of Communication dated Sep. 3, 2019 by the China National Intellectual Property Administration in application No. 201580067262.2.

\* cited by examiner

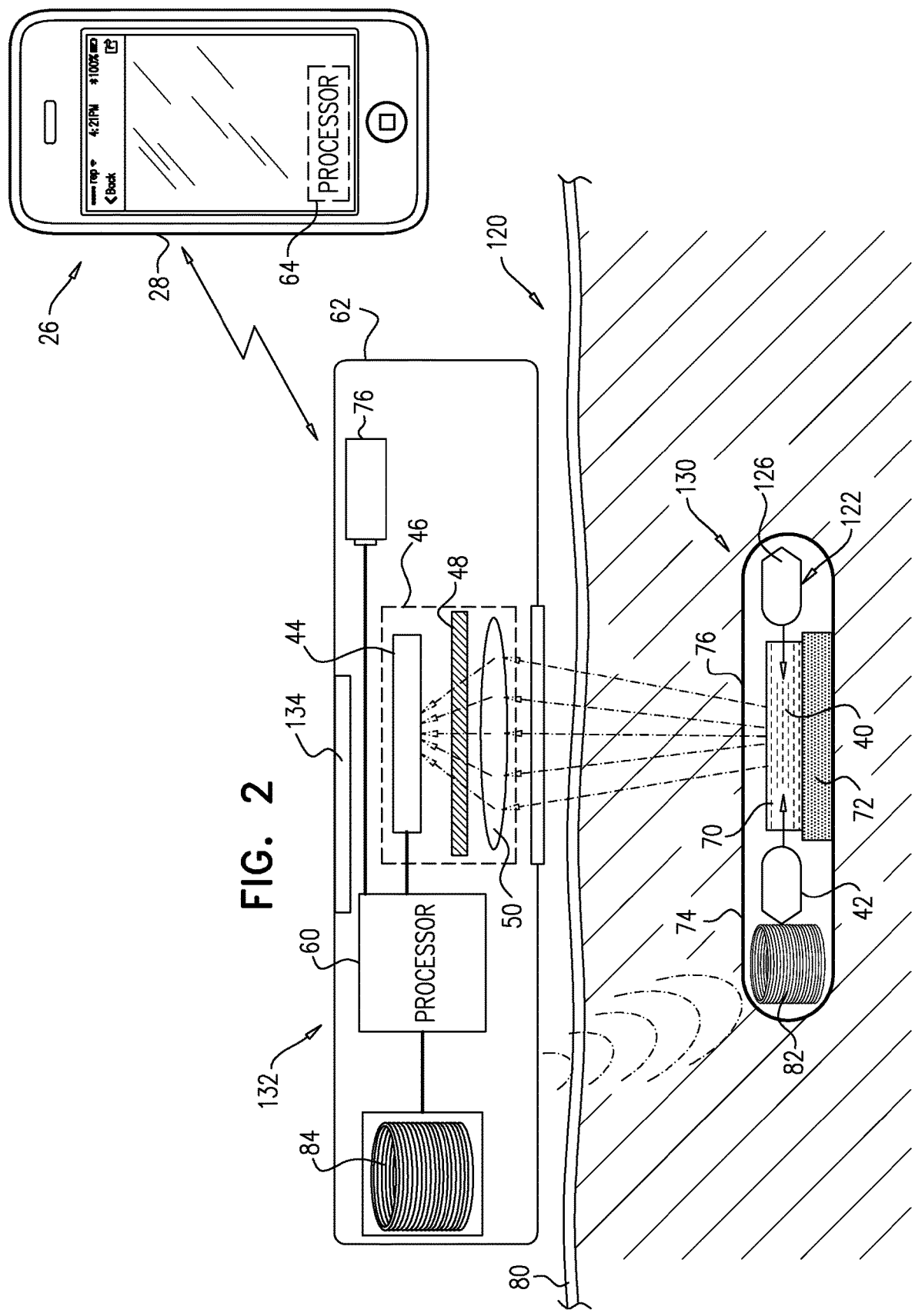

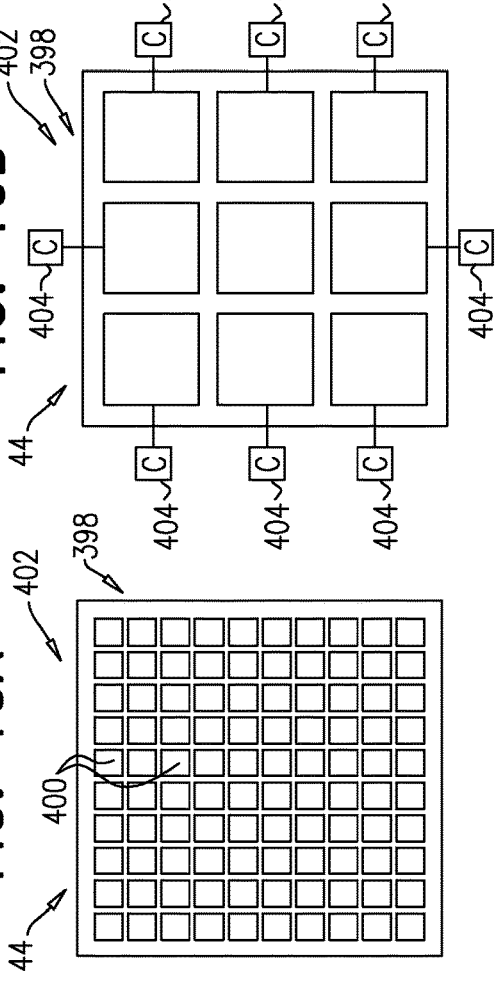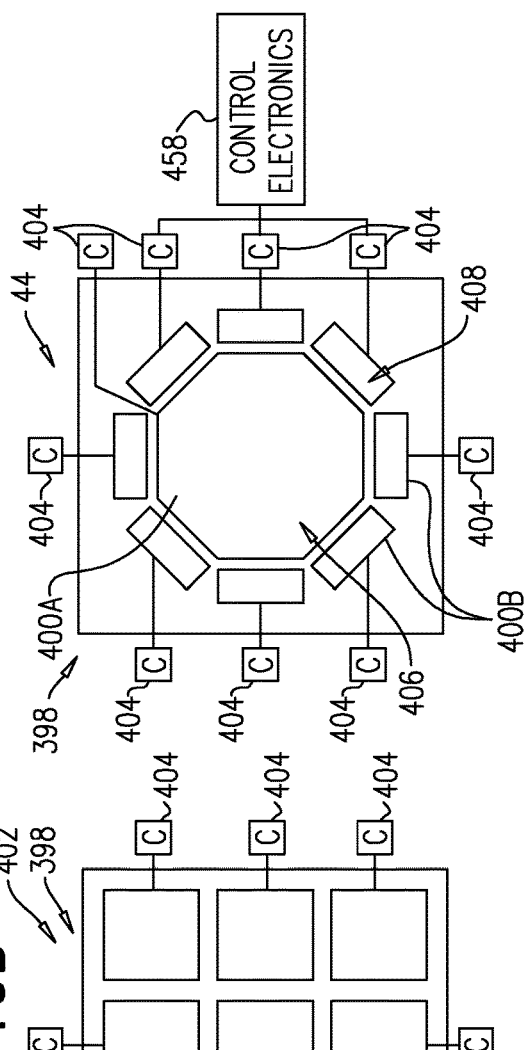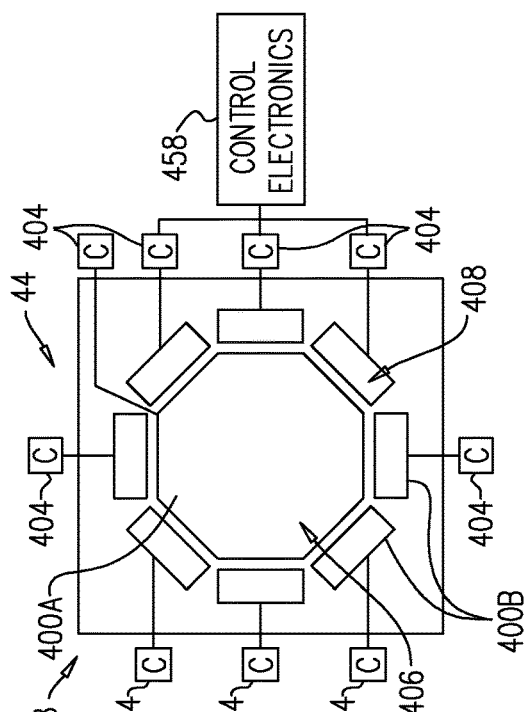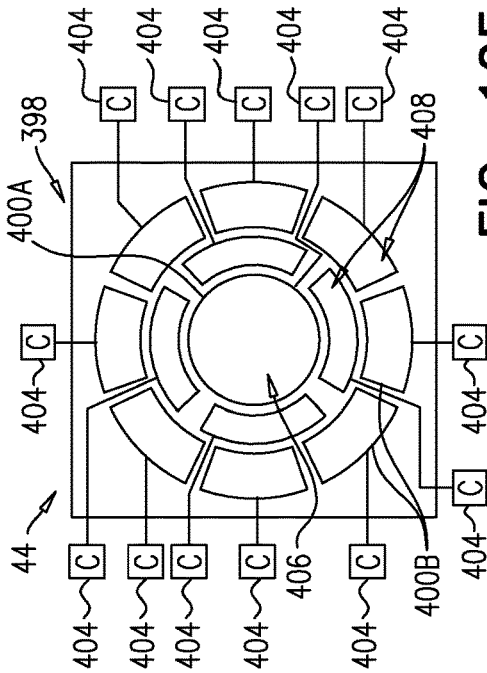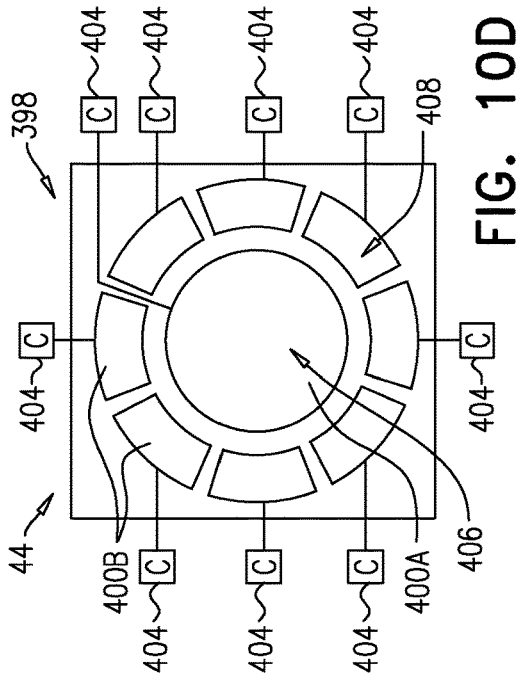

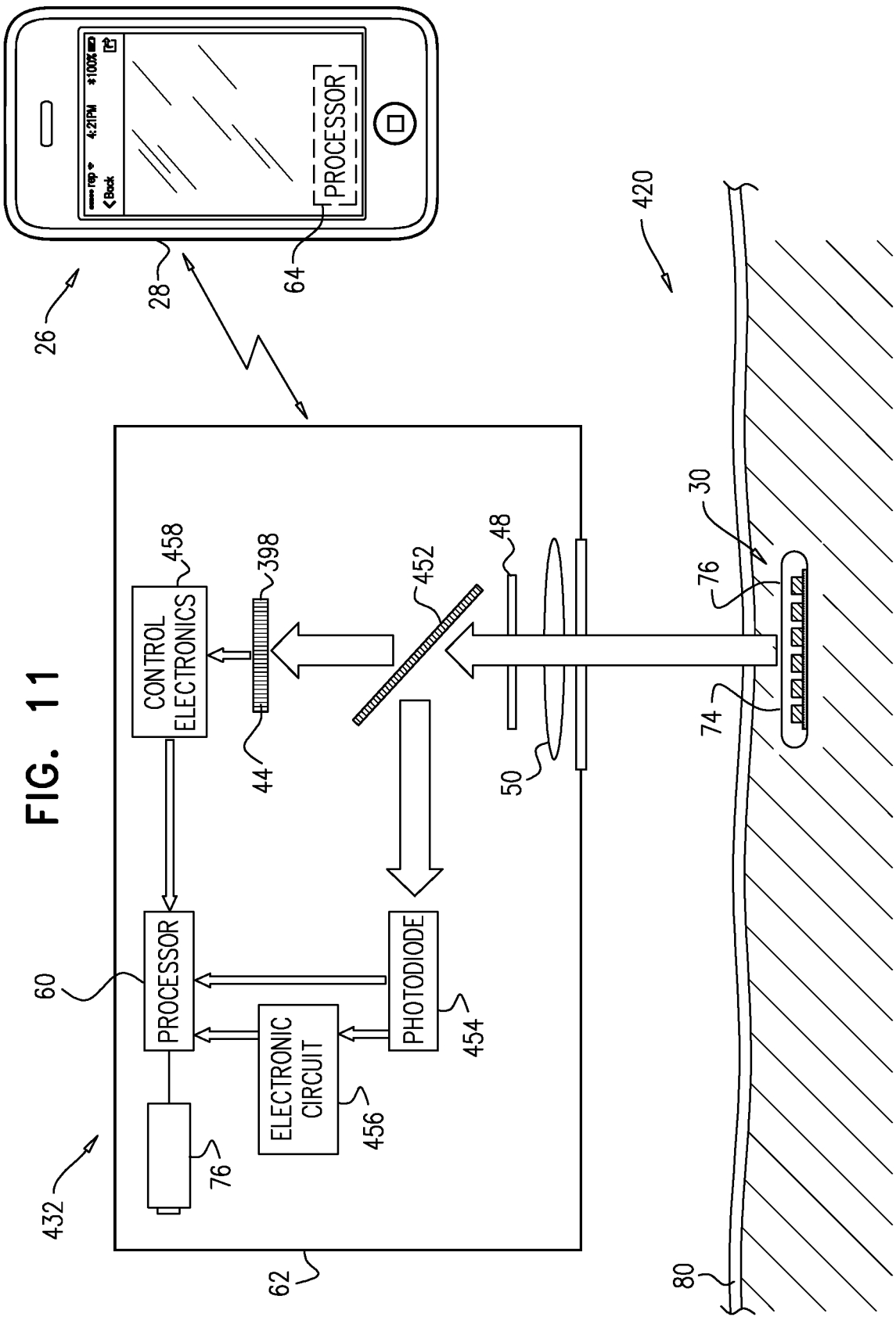

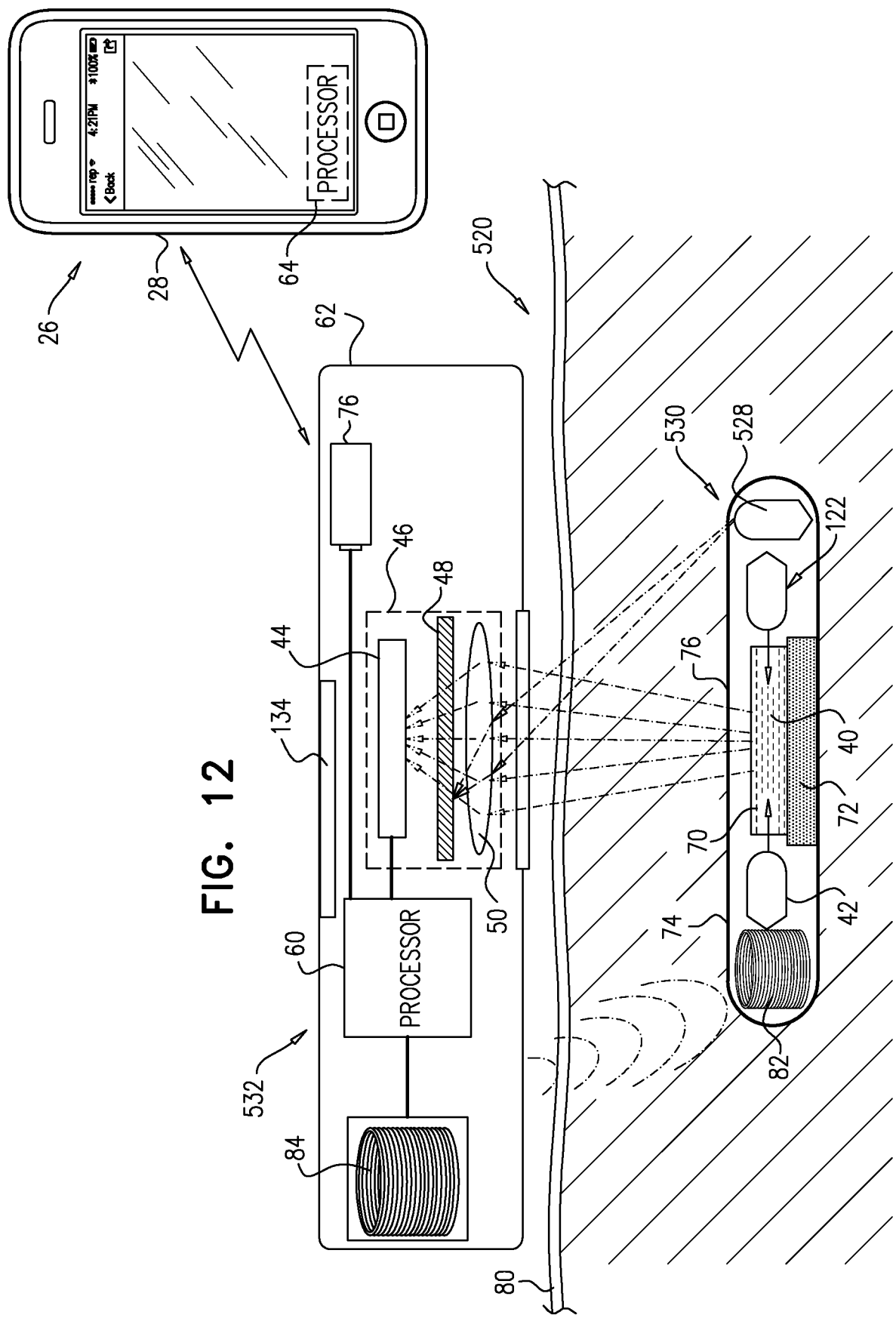

ANALYTE-SENSING DEVICE

CROSS-REFERENCE TO RELATED APPLICATIONS

The present application is the US national stage of International Application PCT/IL2015/051022, which claims priority from U.S. Provisional Application 62/063,211, filed Oct. 13, 2014, which is assigned to the assignee of the present application and is incorporated herein by reference.

FIELD OF THE APPLICATION

Some applications of the present invention relate generally to implantable sensors for detecting an analyte in a body and specifically to methods and apparatus for reading the optical signal from an implantable medical device.

BACKGROUND OF THE APPLICATION

The monitoring of various medical conditions often requires measuring the levels of various components within the blood. In order to avoid invasive repeated blood drawing, implantable sensors aimed at detecting various components of blood in the body have been developed. More specifically, in the field of endocrinology, in order to avoid repeated "finger-sticks" for drawing blood to assess the levels of glucose in the blood in patients with diabetes mellitus, implantable glucose sensors have been discussed.

One method for sensing the concentration of an analyte such as glucose relies on Fluorescence Resonance Energy Transfer (FRET). FRET involves the transfer of energy from an excited fluorophore (the donor) to another fluorophore (the acceptor) when the donor and acceptor are in close proximity to each other, leading to fluorescence emission by the acceptor. Because of the high sensitivity of the FRET signal to the relative proximity of the fluorophores it is often used in biological research as a measurement tool. For example, the concentration of an analyte such as glucose can be measured by creating a fused sensor which includes two fluorophores and a third moiety which has specific binding site for the analyte. The conformational change of the fused sensor which results from the binding of the analyte changes the distance between the fluorophores, affecting the FRET signal and thus enabling the measurement of the analyte concentration.

PCT Patent Application Publication WO 2006/006166 to Gross et al., which is incorporated herein by reference, describes a protein which includes a glucose binding site, cyan fluorescent protein (CFP), and yellow fluorescent protein (YFP). The protein is configured such that binding of glucose to the glucose binding site causes a reduction in a distance between the CFP and the YFP. Apparatus is described for detecting a concentration of a substance in a subject, the apparatus comprising a housing adapted to be implanted in the subject. The housing comprises a fluorescence resonance energy transfer (FRET) measurement device and cells genetically engineered to produce, in situ, a FRET protein having a FRET complex comprising a fluorescent protein donor, a fluorescent protein acceptor, and a binding site for the substance.

An alternative approach to glucose sensing has been discussed e.g. by Y J Heo et al., in "Towards Smart Tattoos: Implantable Biosensors for Continuous Glucose Monitoring," Adv. Healthcare Mater. 2013 January; 2(1):43-56 (Epub Nov. 26, 2012). Heo et al. provide a review of the efforts to develop analyte monitoring methods, which include placing a fluorescent material sensitive to a target analyte, e.g., glucose, under the skin and reading the optical signal through the skin, thus enabling measurement of the analyte.

In recent years, improved far-red fluorophores, having a significant portion of their emission spectrum above 650 nm, have been developed in order to exploit optical properties of biological tissue and enable in-vivo deep imaging, including, e.g., TagRFP, mRuby, mRuby2, mPlum, FusionRed, mNeptune, mNeptune2.5, mCardinal, Katushka, mKate, mKate2, mRaspberry and others. The relative emission of these fluorophores at an optical window above 650 nm is typically 10-50%, enabling sufficiently-effective detection through the skin. Additionally, infrared phytochromes such as iRFP, IFP1.4, and IFP2.0 have been developed which further push the emission spectrum into the infrared; however, these phytochromes depend on the availability of biliverdin, possibly complicating their practical use. Red fluorophores may effectively be used in conjunction with shorter-wavelengths fluorophores (e.g., green) to create FRET couples that can be used to develop different types of biosensors, as shown for example by Lam et al.

SUMMARY OF THE APPLICATION

Some applications of the present invention provide a system for transdermal detection of a concentration of an analyte, such as glucose, in a subject. The system comprises an implantable unit and an external system, which comprises an external reading unit and, optionally, an external monitor unit. The implantable unit comprises fluorescent sensor molecules, each of which comprises a binding site for the analyte, and at least one fluorescent moiety.

Accurate transdermal measurement of optical signals is challenging in practice in part because of the properties of skin and other tissue between an implanted unit and an external reading unit. Low transmission through the skin and other tissue may result in low signal-to-background and signal-to-noise ratios, compromising measurement accuracy. In addition, spatial and angular non-uniformity of the measurement may be caused by transmission non-uniformity, for example because of non-uniform skin pigmentation and/or tissue auto-fluorescence. These and other factors may compromise measurement quality and limit measurement accuracy. Some techniques of the present invention enable accurate measurement through the skin, with particular application in the measurement of the concentration of the analyte, e.g., glucose, using an implanted fluorescent responder, such as a Fluorescence Resonance Energy Transfer (FRET) biosensor. The fluorescent moiety of each of the FRET fluorescent sensor molecules comprises a donor fluorophore, and an acceptor fluorophore, as well as an analyte-binding moiety which reversibly changes its shape following specific binding to the target analyte.

Light penetration through tissue in general, and skin in particular, is greatest at the red and near infrared portions of the spectrum, i.e., at wavelengths of between about 650 and 1250 nm, with greatest penetration at between about 700 and 750 nm. Tissue absorption is substantially higher at both lower and higher wavelengths, mainly because of the high absorption of hemoglobin at lower wavelengths and water absorption at higher wavelengths. At practical subcutaneous implantation depths of about 1 to 3 mm, an optical signal at the range of 650 to 750 nm suffers some absorption and scattering, but a significant percentage of signal passes through the skin and other tissue.

Typically, the acceptor fluorophore of the FRET sensor molecules is selected such that a substantial portion of the light emitted by the acceptor fluorophore is able to penetrate through at least 0.5 mm, e.g., at least 1 mm, such as at least 2 mm of tissue (which typically includes the skin). For example, the acceptor fluorophore may be selected such that a substantial portion (e.g., at least 10%, such as at least 20%, e.g., at least 40%) of the emission spectrum of the acceptor fluorophore is at a wavelength greater than 600 nm, e.g., greater than 625 nm, greater than 650 nm, or greater than 700 nm. Typically, the emission peak wavelength corresponds approximately to this wavelength of the substantial portion of the emission spectrum, such that the emission peak wavelength of the acceptor fluorophore is greater than 600 nm, e.g., greater than 625 nm, greater than 650 nm, or greater than 700 nm.

For some applications, the implantable unit further comprises an implantable-unit light source. Typically, the implantable-unit light source is configured to generate light having an illumination peak wavelength that is greater than 300 nm and less than 600 nm, typically less than 550 nm (e.g., less than 525 nm, such as less than 500 nm, e.g., about 470 nm) and appropriate for excitation of the fluorescent moiety. Upon excitation, the fluorescent moiety emits fluorescent light having an emission peak wavelength.

The external reading unit typically comprises a light sensor, which is configured to sense fluorescent light emitted from the fluorescent moiety. The external system further comprises one or more processors, which are configured to: (i) receive, from the light sensor, at least one measurement of the fluorescent light emitted from the fluorescent moiety, and (ii) calculate the concentration of the analyte in the subject based on the at least one measurement.

This arrangement allows a relatively small and simple implantable unit, with minimal circuitry and a single implantable-unit light source. The implantable-unit light source generates light at the relatively low wavelength, such as less than 600 nm, typically less than 550 nm, e.g., less than 525 nm, which is necessary for exciting most red acceptor fluorophores, but has poor penetration of skin and other tissue. Generation of this excitation light inside the implantable unit obviates the need for the light to pass through the skin. However, the higher wavelength light emitted by the fluorescent sensor molecules has good penetration through the skin to the light sensor of the external reading unit. The external reading unit, rather than the smaller, simpler implantable unit, contains the optical elements and circuitry for sensing and processing the emitted light, thereby allowing for minimization of the size and complexity of the implantable unit.

For some applications, the implantable-unit light source is a first implantable-unit light source, which is configured to generate light having a first illumination peak wavelength appropriate for excitation of the donor fluorophore, while minimizing the direct excitation of the acceptor fluorophore. The system further comprises a second light source, which is configured to generate light having a second illumination peak wavelength appropriate for direct excitation of the acceptor fluorophore, while optionally minimizing the excitation of the donor fluorophore. For some applications, the second light source comprises a second external-unit light source, while for other applications, the second light source comprises a second implantable-unit light source.

For some applications, the one or more processors are configured to:

during one or more first time periods: (a) drive the first implantable-unit light source to generate the light having the first illumination peak wavelength, and (b) receive, from the light sensor, one or more first measurements (typically of the intensity) of the fluorescent light emitted from the acceptor fluorophore. As a result, a significant portion of the signal is related to the FRET effect and is thus sensitive to the concentration of the analyte. Typically, the emission spectrum from the acceptor fluorophore is selected to have good transmission through tissue including skin, and thus the emission peak wavelength is typically in the red or infrared portions of the spectrum;

during one or more second time periods non-overlapping with the first time periods: (a) drive the second light source to generate the light having the second illumination peak wavelength, appropriate for direct excitation of the acceptor fluorophore, and (b) receive, from the light sensor, one or more second measurements (typically of the intensity) of the fluorescent light emitted from the acceptor fluorophore. These second measurements are thus largely insensitive of the concentration of the analyte. However, these second measurements provide an optimal reference, because they are of the same emission spectrum as the first measurements, and are dependent in the same way as the first measurement on a number of factors, including (a) the concentration of the FRET sensor molecules, (b) transmission of the optical signal through tissue including skin and/or other intervening material, and through the same optical components of the system, and (c) sensor sensitivity; and calculate the concentration of the analyte in the subject based on the first and the second measurements, such as by calculating the ratio of the first and the second measurements. Typically, the one or more processors are configured to apply calibration procedures to both the first and the second measurements, including, for example, background subtraction and/or non-linearity correction. For some applications, the one or more processors are configured to calculate the concentration by dividing the first measurements (optionally calibrated) by the second measurements (optionally calibrated). The ratio thus obtained is thus corrected for common factors, including the amount of the FRET sensor molecules in the implantable unit, their distribution, transmission of the full optical path, including tissue (including skin), as well as the response of the collection channel. Differences between the two measurements that relate to the different excitation conditions, e.g., wavelength, optical path, and transmission through the tissue (including skin), are either assumed constant or otherwise calibrated.

Typically, the same collecting optics and light sensor is used to measure the emission from the acceptor fluorophore during the first and the second time periods.

The emission peak wavelength of the acceptor fluorophore is typically at least 600 nm, such as at least 625 nm (in the red or infrared portion of the spectrum), such that a substantial portion of the emission spectrum is at a wavelength above 650 nm, which has better transmission through skin and other tissue than the lower-wavelength spectrum emitted from the donor fluorophore in conventional FRET techniques. Thus, this technique, unlike convention FRET measurement techniques, enables all signal sensing to be performed under good tissue transmission conditions.

For some applications, the one or more processors are configured to use one or more algorithms in order to separate between the fluorescent light emitted from the fluorescent moiety and background (e.g., ambient) light, and to reduce (e.g., remove) the contribution of the background light to the detected light signal. For some applications, the one or more algorithms utilize prior information regarding the shape (including size), in one or two dimensions, of one or more regions of the implantable unit at which the fluorescent sensor molecules are disposed, in order to identify the fluorescent light emitted from the fluorescent moiety. For applications in which the implantable unit comprises the at least one sensor molecule chamber, which contains the fluorescent sensor molecules, the one or more algorithms utilize prior information regarding the shape (including size), in one or two dimensions, of the at least one sensor molecule chamber.

In these applications, the light sensor comprises an image sensor, i.e., a sensor that senses features of a spatial distribution of photons that impinge on the sensor. The image sensor is configured to generate one or more transdermal images of light passing from the body through tissue including skin.

For some of these applications, the one or more processors are configured to:
calculate at least one intensity of the light representing emission from the fluorescent sensor molecules, based on distinguishing between (a) one or more emission areas of the transdermal images corresponding to the locations, in one or two dimensions, of the fluorescent sensor molecules, and (b) background areas of the transdermal images, and
calculate the concentration of the analyte in the subject based on the at least one intensity of the light emitted from the fluorescent sensor molecules.

For some applications, the external system (e.g., the external reading unit) further comprises a user interface, which typically comprises a graphical display, other visual outputs, and/or an audio generator. The one or more processors are configured to (a) ascertain, responsively to one or more respective locations of the one or more emission areas of the transdermal images, a desired movement of the external reading unit with respect to an external surface of the skin, and (b) output, via the user interface, an indication of the desired movement. A user moves the external reading unit in order to better align the external reading unit with the implantable unit.

For some applications, the one or more processors are configured to use a one- or two-dimensional representation of a spatial distribution of the fluorescent sensor molecules in the implantable unit as a factor in the analysis of the transdermal images for ascertaining the one or more areas of the transdermal images corresponding to the locations, in one or two dimensions, of the fluorescent sensor molecules. For example, the one- or two-dimensional representation may be loaded in a memory of the external system before the external reading unit is provided to the user. The one or more processors are configured to analyze the one- or two-dimensional images of the sensed light with reference to the one- or two-dimensional representation in order to find a best fit between the images and the representation, and then to assume that light outside of this best fit is background noise rather than emissions from the fluorescent sensor molecules.

For some applications, the fluorescent sensor molecules are distributed within the implantable unit in a repetitive pattern, and/or in a non-uniform spatial distribution. For some applications, the fluorescent sensor molecules are distributed within the implantable unit such that in one or more distinct areas a different signal intensity is detected as compared to other areas in which the fluorescent sensor molecules are distributed For example, a sensor molecule chamber containing the fluorescent sensor molecules may have a greater or lesser thickness in the distinct areas than in the other areas. Alternatively or additionally, for some applications, the fluorescent sensor molecules are distributed within the implantable unit with one or more distinct areas of higher concentration than other areas in which the fluorescent sensor molecules are distributed.

For some applications, the implantable unit comprises at least one first implantable-unit light source and at least one second implantable-unit light source. The external reading unit is configured to drive the first and the second implantable-unit light sources to generate the light having the first and the second illumination peak wavelengths, respectively, by transmitting electromagnetic radiation at first and second different RF frequencies, respectively. As mentioned above, the first illumination peak wavelength is appropriate for excitation of the donor fluorophore, while minimizing the direct excitation of the acceptor fluorophore, and the second illumination peak wavelength is appropriate for direct excitation of the acceptor fluorophore, while optionally minimizing the excitation of the donor fluorophore.

For some applications, the implantable unit comprises first and second wireless energy receivers, which are configured to receive the electromagnetic radiation at the first and the second RF frequencies, respectively. The first and the second wireless energy receivers are electrically coupled to the first and the second implantable-unit light sources, respectively, such that the first and second wireless energy receivers, when they receive the electromagnetic radiation, activate the first and second light sources, respectively. The external reading unit thus transmits the electromagnetic radiation at the first RF frequency in order to activate the first implantable-unit light source, and at the second RF frequency in order to activate the second implantable-unit light source. Typically, the first and the second wireless energy receivers comprise respective different sized coils and/or different capacitors in order to tune the receivers to their respective RF frequencies. This configuration simplifies the implantable unit, because only minimal (possibly discrete electronics) or no circuitry is needed to activate the implantable-unit light sources. In this configuration, the length and optionally also the power of the illumination is directly controlled by the energy pulses transmitted by the external reading unit, allowing direct feedback to the one or more processors to compensate for variations in signal strength resulting, for example, from variations in the concentration of the fluorescent sensor molecules from implantable unit to implantable unit or as a function of time.

For some applications, the external reading unit comprises the first and the second wireless energy transmitters, which are configured to transmit the electromagnetic radiation at the first and the second RF frequencies, respectively, and thus activate the first and the second implantable-unit light sources, respectively. Typically, the first and the second wireless energy transmitter comprise respective different sized coils and/or different capacitors in order to tune the transmitters to their respective RF frequencies, thereby eliminating crosstalk between the transmitters.

For some applications, the implantable unit further comprises an upconversion material, which is disposed in a vicinity of the fluorescent sensor molecules. The at least one fluorescent moiety of the fluorescent sensor molecules is configured to be excited by light between a first absorption wavelength and a second absorption wavelength greater than the first absorption wavelength. The upconversion material is configured to produce emission of light having an emission peak wavelength between the first absorption wavelength and the second absorption wavelength, upon being excited with light having an excitation peak wavelength that is greater than the second absorption wavelength. The emission peak wavelength is typically in the visible light spectrum, and is appropriate for excitation of the at least one fluorescent moiety. The excitation peak wavelength is selected for good penetration through tissue including skin, and has better tissue penetration than the emission peak wavelength. The light emitted from the upconversion material is used to excite at least one fluorescent moiety of the biosensor, thus minimizing or eliminating the need to include a light source in the implantable unit. For some applications, the upconversion material comprises nanocrystals. For some applications, the emission peak wavelength is less than 700 nm, and the excitation peak wavelength is greater than 700 nm. For example, the excitation peak wavelength may be greater than 800 nm, and the upconversion material may be configured to emit light with a peak wavelength of less than 650 nm upon being excited with the excitation light with peak wavelength of greater than 800 nm.

There is therefore provided, in accordance with an inventive concept 1, apparatus for detecting a concentration of an analyte in a subject, the apparatus comprising:
an implantable unit, which is configured to be implanted in a body of the subject, and comprises:
  (a) fluorescent sensor molecules, each of which comprises (i) a binding site for the analyte, and (ii) at least one fluorescent moiety configured to emit fluorescent light; and
  (b) an implantable-unit light source that is configured to generate light having an illumination peak wavelength appropriate for excitation of the fluorescent moiety; and
an external system, which is physically separate and distinct from the implantable unit, and which comprises:
  (a) an external reading unit, which comprises a light sensor, which is configured to sense fluorescent light emitted from the fluorescent moiety having an emission peak wavelength, wherein the emission peak wavelength is between 100 and 500 nm greater than the illumination peak wavelength; and
  (b) one or more processors, which are configured to: (1) drive the implantable-unit light source to generate the light, (2) receive, from the light sensor, at least one measurement of the fluorescent light emitted from the fluorescent moiety, and (3) calculate the concentration of the analyte in the subject based on the at least one measurement.

Inventive concept 2. The apparatus according to inventive concept 1, wherein the emission peak wavelength is between 100 and 250 nm greater than the illumination peak wavelength.

Inventive concept 3. The apparatus according to inventive concept 1, wherein the emission peak wavelength is at least 150 nm greater than the illumination peak wavelength.

Inventive concept 4. The apparatus according to inventive concept 1, wherein the fluorescent moiety of each of the fluorescent sensor molecules comprises a donor fluorophore, and an acceptor fluorophore.

Inventive concept 5. The apparatus according to inventive concept 1, wherein each of the fluorescent sensor molecules comprises exactly one fluorescent moiety.

Inventive concept 6. The apparatus according to inventive concept 1, wherein each of the fluorescent sensor molecules comprises exactly two fluorescent moieties.

Inventive concept 7. The apparatus according to inventive concept 1, wherein the implantable unit further comprises at least one sensor molecule chamber, in which the fluorescent sensor molecules are disposed.

Inventive concept 8. The apparatus according to inventive concept 1, wherein the implantable unit comprises circuitry, and wherein the one or more processors are configured to drive the implantable-unit light source to generate the light by driving the circuitry of the implantable unit to activate the implantable-unit light source to generate the light.

Inventive concept 9. The apparatus according to inventive concept 1, wherein the fluorescent sensor molecules are fluorescent sensor proteins.

Inventive concept 10. The apparatus according to any one of inventive concepts 1-9, wherein the analyte is glucose, and wherein the binding site is for the glucose.

Inventive concept 11. The apparatus according to any one of inventive concepts 1-9, wherein the illumination peak wavelength is greater than 300 nm and less than 550 nm.

Inventive concept 12. The apparatus according to inventive concept 11, wherein the illumination peak wavelength is less than 525 nm.

Inventive concept 13. The apparatus according to inventive concept 12, wherein the illumination peak wavelength is less than 500 nm.

Inventive concept 14. The apparatus according to any one of inventive concepts 1-9, wherein the implantable unit has a volume of no more than 250 mm3.

Inventive concept 15. The apparatus according to any one of inventive concepts 1-9, further comprising packaging, in which the implantable unit is stored before implantation, wherein an external surface of the implantable unit is sterile while stored in the packaging.

Inventive concept 16. The apparatus according to any one of inventive concepts 1-9, wherein the apparatus is configured to measure a temperature at the implantable unit, and wherein the one or more processors are configured to generate calibration information using the measured temperature, and calculate the concentration of the analyte using the calibration information.

There is further provided, in accordance with an inventive concept 17, apparatus for detecting a concentration of an analyte in a subject, the apparatus comprising:
an implantable unit, which is configured to be implanted in a body of the subject, and comprises:
  (a) fluorescent sensor molecules, each of which comprises (i) a binding site for the analyte, and (ii) at least one fluorescent moiety; and
  (b) an implantable-unit light source that is configured to generate light having an illumination peak wavelength that is greater than 300 nm and less than 550 nm and appropriate for excitation of the fluorescent moiety; and
an external system, which is physically separate and distinct from the implantable unit, and which comprises:
  (a) an external reading unit, which comprises a light sensor, which is configured to sense fluorescent light emitted from the fluorescent moiety; and
  (b) one or more processors, which are configured to: (i) receive, from the light sensor, at least one measurement of the fluorescent light emitted from the fluorescent moiety, and (ii) calculate the concentration of the analyte in the subject based on the at least one measurement.

Inventive concept 18. The apparatus according to inventive concept 17, wherein the one or more processors are configured to drive the implantable-unit light source to generate the light.

Inventive concept 19. The apparatus according to inventive concept 18, wherein the implantable unit comprises circuitry, and wherein the one or more processors are configured to drive the implantable-unit light source to generate the light by driving the circuitry of the implantable unit to activate the implantable-unit light source to generate the light.

Inventive concept 20. The apparatus according to inventive concept 17, wherein the illumination peak wavelength is less than 525 nm.

Inventive concept 21. The apparatus according to inventive concept 20, wherein the illumination peak wavelength is less than 500 nm.

Inventive concept 22. The apparatus according to inventive concept 17, wherein the fluorescent moiety of each of the fluorescent sensor molecules comprises a donor fluorophore, and an acceptor fluorophore.

Inventive concept 23. The apparatus according to inventive concept 17, wherein each of the fluorescent sensor molecules comprises exactly one fluorescent moiety.

Inventive concept 24. The apparatus according to inventive concept 17, wherein each of the fluorescent sensor molecules comprises exactly two fluorescent moieties.

Inventive concept 25. The apparatus according to inventive concept 17, wherein the implantable unit further comprises at least one sensor molecule chamber, in which the fluorescent sensor molecules are disposed.

Inventive concept 26. The apparatus according to inventive concept 17, wherein the fluorescent sensor molecules are fluorescent sensor proteins.

Inventive concept 27. The apparatus according to any one of inventive concepts 17-26, wherein the analyte is glucose, and wherein the binding site is for the glucose.

Inventive concept 28. The apparatus according to any one of inventive concepts 17-26, wherein the fluorescent moiety is configured to emit the fluorescent light having an emission peak wavelength that is between 100 and 500 nm greater than the illumination peak wavelength.

Inventive concept 29. The apparatus according to inventive concept 28, wherein the emission peak wavelength is between 100 and 250 nm greater than the illumination peak wavelength.

Inventive concept 30. The apparatus according to inventive concept 28, wherein the emission peak wavelength is at least 150 nm greater than the illumination peak wavelength.

Inventive concept 31. The apparatus according to any one of inventive concepts 17-26, wherein the implantable unit has a volume of no more than 250 mm3.

Inventive concept 32. The apparatus according to any one of inventive concepts 17-26, further comprising packaging, in which the implantable unit is stored before implantation, wherein an external surface of the implantable unit is sterile while stored in the packaging.

Inventive concept 33. The apparatus according to any one of inventive concepts 17-26, wherein the apparatus is configured to measure a temperature at the implantable unit, and wherein the one or more processors are configured to generate calibration information using the measured temperature, and calculate the concentration of the analyte using the calibration information.

There is still further provided, in accordance with an inventive concept 34, apparatus for detecting a concentration of an analyte in a subject, the apparatus comprising:

an implantable unit, which is configured to be implanted in a body of the subject, and comprises:

(a) fluorescent sensor molecules, each of which comprises (i) a binding site for the analyte, (ii) a donor fluorophore, and (iii) an acceptor fluorophore; and (b) a first implantable-unit light source that is configured to generate light having a first illumination peak wavelength appropriate for excitation of the donor fluorophore;

a second light source that is configured to generate light having a second illumination peak wavelength appropriate for direct excitation of the acceptor fluorophore; and an external system, which is physically separate and distinct from the implantable unit, and which comprises:

(a) an external reading unit, which comprises a light sensor, which is configured to sense fluorescent light emitted from the acceptor fluorophore; and (b) one or more processors, which are configured to:

(i) during one or more first time periods: (a) drive the first implantable-unit light source to generate the light having the first illumination peak wavelength, and (b) receive, from the light sensor, one or more first measurements of the fluorescent light emitted from the acceptor fluorophore, (ii) during one or more second time periods non-overlapping with the first time periods: (a) drive the second light source to generate the light having the second illumination peak wavelength, and (b) receive, from the light sensor, one or more second measurements of the fluorescent light emitted from the acceptor fluorophore, and (iii) calculate the concentration of the analyte in the subject based on the first and the second measurements.

Inventive concept 35. The apparatus according to inventive concept 34, wherein the external reading unit comprises the second light source.

Inventive concept 36. The apparatus according to inventive concept 34, wherein the implantable unit comprises the second light source.

Inventive concept 37. The apparatus according to inventive concept 36, wherein the external reading unit is configured to drive the first and the second light sources to generate the light having the first and the second illumination peak wavelengths, respectively, by transmitting electromagnetic radiation at first and second different frequencies, respectively.

Inventive concept 38. The apparatus according to inventive concept 34, wherein the implantable unit further comprises at least one sensor molecule chamber, in which the fluorescent sensor molecules are disposed.

Inventive concept 39. The apparatus according to inventive concept 34, wherein the fluorescent sensor molecules are fluorescent sensor proteins.

Inventive concept 40. The apparatus according to any one of inventive concepts 34-39, wherein the first illumination peak wavelength is greater than 300 nm and less than 550 nm.

Inventive concept 41. The apparatus according to inventive concept 40, wherein the first illumination peak wavelength is less than 525 nm.

Inventive concept 42. The apparatus according to inventive concept 41, wherein the first illumination peak wavelength is less than 500 nm.

Inventive concept 43. The apparatus according to any one of inventive concepts 34-39, wherein the second illumination peak wavelength is greater than 300 nm and less than 650 nm.

Inventive concept 44. The apparatus according to any one of inventive concepts 34-39, wherein the first illumination peak wavelength is greater than 300 nm and less than 550 nm, and the second illumination peak wavelength is greater than 300 nm and less than 650 nm.

Inventive concept 45. The apparatus according to any one of inventive concepts 34-39, wherein the acceptor fluorophore is configured to emit the fluorescent light having an emission peak wavelength that is between 100 and 500 nm greater than the first illumination peak wavelength.

Inventive concept 46. The apparatus according to any one of inventive concepts 34-39, wherein the analyte is glucose, and wherein the binding site is for the glucose.

Inventive concept 47. The apparatus according to any one of inventive concepts 34-39, wherein the implantable unit has a volume of no more than 250 mm3.

Inventive concept 48. The apparatus according to any one of inventive concepts 34-39, further comprising packaging, in which the implantable unit is stored before implantation, wherein an external surface of the implantable unit is sterile while stored in the packaging.

Inventive concept 49. The apparatus according to any one of inventive concepts 34-39, wherein the apparatus is configured to measure a temperature at the implantable unit, and wherein the one or more processors are configured to generate calibration information using the measured temperature, and calculate the concentration of the analyte using the calibration information.

There is additionally provided, in accordance with an inventive concept 50, apparatus for detecting a concentration of an analyte in a subject, the apparatus comprising:

an implantable unit, which is configured to be implanted in a body of the subject, and comprises (a) fluorescent sensor molecules, each of which comprises (i) a binding site for the analyte, (ii) a donor fluorophore, and (iii) an acceptor fluorophore;

one or more light sources;

a light sensor, which is configured to sense fluorescent light emitted from the acceptor fluorophore; and one or more processors, which are configured to:
drive the one or more light sources to (a) during a plurality of first time periods, generate light having a first illumination peak wavelength appropriate for excitation of the donor fluorophore, and (b) during a plurality of second time periods non-overlapping with the first time periods, generate light having a second illumination peak wavelength appropriate for direct excitation of the acceptor fluorophore,
receive, from the light sensor, respective measurements of the fluorescent light emitted from the acceptor fluorophore during (a) the first time periods and (b) the second time periods,
calculate the concentration of the analyte in the subject based on the respective measurements,
during a first operational period that includes one or more of the first time periods and one or more of the second time periods, set a ratio of an aggregate duration of the first time periods to an aggregate duration of the second time periods to have a first value, and
during a second operational period that is after the first operational period and that includes one or more of the first time periods and one or more of the second time periods, set the ratio to have a second value that is different from the first value.

Inventive concept 51. The apparatus according to inventive concept 50, wherein the second value of the ratio is greater than the first value of the ratio.

Inventive concept 52. The apparatus according to inventive concept 50, wherein the first operation period has a duration of at least one week.

Inventive concept 53. The apparatus according to inventive concept 50, wherein the one or more processors are configured to set the ratio to have the second value based on a decrease in signal strength of the fluorescent sensor molecules.

Inventive concept 54. The apparatus according to inventive concept 50, wherein the one or more processors are configured to set the ratio to have the second value based on a decrease in a concentration of the fluorescent sensor molecules.

Inventive concept 55. The apparatus according to inventive concept 54, wherein the one or more processors are configured to ascertain the decrease in the concentration of the fluorescent sensor molecules.

Inventive concept 56. The apparatus according to inventive concept 55,
wherein the light sensor comprises an image sensor, which is configured to generate one or more transdermal images of the fluorescent light emitted from the acceptor fluorophore, and
wherein the one or more processors are configured to, during one or more third time periods non-overlapping with the first time periods: (a) drive the one or more light sources to generate the light having the second illumination peak wavelength, and (b) calculate the concentration of the fluorescent sensor molecules, by analyzing a spatial distribution of the fluorescent light in the transdermal images.

Inventive concept 57. The apparatus according to inventive concept 56, wherein the one or more processors are configured to, during the one or more third time periods, analyze the distribution of the fluorescent light in the transdermal images by calculating an extent of absorption of the fluorescent light emitted from the acceptor fluorophore as a function of distance from the one or more second light sources.

Inventive concept 58. The apparatus according to inventive concept 50,
wherein the one or more light sources comprise one or more first light sources and one or more second light sources, and
wherein the one or more processors are configured to drive the one or more first light sources to generate the light having the first illumination peak wavelength, and the one or more second light sources to generate the light having the second illumination peak wavelength.

Inventive concept 59. The apparatus according to inventive concept 58, wherein the implantable unit comprises the one or more first light sources and the one or more second light sources.

Inventive concept 60. The apparatus according to inventive concept 59, wherein the one or more processors are configured to drive the first and the second light sources to generate the light having the first and the second illumination peak wavelengths, respectively, by transmitting electromagnetic radiation at first and second different frequencies, respectively.

Inventive concept 61. The apparatus according to inventive concept 58, further comprising an external reading unit, which is physically separate and distinct from the implantable unit, and which comprises the one or more second light sources, wherein the implantable unit comprises the one or more first light sources.

Inventive concept 62. The apparatus according to inventive concept 50, wherein the implantable unit further comprises at least one sensor molecule chamber, in which the fluorescent sensor molecules are disposed.

Inventive concept 63. The apparatus according to inventive concept 50, wherein the fluorescent sensor molecules are fluorescent sensor proteins.

Inventive concept 64. The apparatus according to any one of inventive concepts 50-63, wherein the analyte is glucose, and wherein the binding site is for the glucose.

Inventive concept 65. The apparatus according to any one of inventive concepts 50-63, wherein the implantable unit has a volume of no more than 250 mm3.

Inventive concept 66. The apparatus according to any one of inventive concepts 50-63, further comprising packaging, in which the implantable unit is stored before implantation, wherein an external surface of the implantable unit is sterile while stored in the packaging.

Inventive concept 67. The apparatus according to any one of inventive concepts 50-63, further comprising an external reading unit, which is physically separate and distinct from the implantable unit, and which comprises the light sensor.

Inventive concept 68. The apparatus according to any one of inventive concepts 50-63, wherein the implantable unit comprises the light sensor.

Inventive concept 69. The apparatus according to any one of inventive concepts 50-63, wherein the apparatus is configured to measure a temperature at the implantable unit, and wherein the one or more processors are configured to generate calibration information using the measured temperature, and calculate the concentration of the analyte using the calibration information.

There is yet additionally provided, in accordance with an inventive concept 70, apparatus for detecting a concentration of an analyte in a subject, the apparatus comprising:

an implantable unit, which is configured to be implanted in a body of the subject, and comprises (a) fluorescent sensor molecules, each of which comprises (i) a binding site for the analyte, (ii) a donor fluorophore, and (iii) an acceptor fluorophore;

one or more light sources;

a light sensor, which is configured to sense fluorescent light emitted from the acceptor fluorophore; and one or more processors, which are configured to:
drive the one or more light sources to, during a plurality of first time periods alternating with a plurality of second time periods non-overlapping with the first time periods:
(a) during the first time periods, (i) generate light having a first illumination peak wavelength appropriate for excitation of the donor fluorophore, and (ii) receive, from the light sensor, measurements of first intensities of the fluorescent light emitted from the acceptor fluorophore, and
(b) during the second time periods, (i) generate light having a second illumination peak wavelength appropriate for direct excitation of the acceptor fluorophore, and (ii) receive, from the light sensor, measurements of second intensities of the fluorescent light emitted from the acceptor fluorophore,
for each of a plurality of the first and the second time periods, respectively, set a first energy of the light generated having the first illumination peak wavelength, and a second energy of the light generated having the second illumination peak wavelength, so as to regulate, toward a target value, a relationship of values of the first and the second intensities of the sensed fluorescent light, and
calculate the concentration of the analyte in the subject based in part on the first energy of the generated light having the first illumination peak wavelength and the second energy of the generated light having the second illumination peak wavelength.

Inventive concept 71. The apparatus according to inventive concept 70, wherein the one or more processors are configured to regulate a ratio of the values of the first and the second energies of the sensed fluorescent light, toward the target value.

Inventive concept 72. The apparatus according to inventive concept 70, wherein the one or more processors are configured to regulate a difference between the values of the first and the second energies of the sensed fluorescent light, toward the target value.

Inventive concept 73. The apparatus according to inventive concept 72, wherein the one or more processors are configured to reduce a difference between the values of the first and the second energies of the sensed fluorescent light, toward the target value.

Inventive concept 74. The apparatus according to inventive concept 72, wherein the one or more processors are configured to minimize a difference between the values of the first and the second energies of the sensed fluorescent light, toward the target value.

Inventive concept 75. The apparatus according to inventive concept 70, wherein the one or more processors are configured to calculate the concentration of the analyte in the subject based in part on a ratio of (a) the first energy of the generated light having the first illumination peak wavelength and (b) the second energy of the generated light having the second illumination peak wavelength.

Inventive concept 76. The apparatus according to inventive concept 70,
wherein the one or more light sources comprise one or more first light sources and one or more second light sources, and
wherein the one or more processors are configured to drive the one or more first light sources to generate the light having the first illumination peak wavelength, and the one or more second light sources to generate the light having the second illumination peak wavelength.

Inventive concept 77. The apparatus according to inventive concept 76, wherein the implantable unit comprises the one or more first light sources and the one or more second light sources.

Inventive concept 78. The apparatus according to inventive concept 77, further comprising an external reading unit, which is physically separate and distinct from the implantable unit, and which is configured to drive the first and the second light sources to generate the light having the first and the second illumination peak wavelengths, respectively, by transmitting electromagnetic radiation at first and second different frequencies, respectively.

Inventive concept 79. The apparatus according to inventive concept 76, further comprising an external reading unit, which is physically separate and distinct from the implantable unit, and which comprises the one or more second light sources, wherein the implantable unit comprises the one or more first light sources.

Inventive concept 80. The apparatus according to inventive concept 70, wherein the fluorescent sensor molecules are fluorescent sensor proteins.

Inventive concept 81. The apparatus according to inventive concept 70, wherein the implantable unit further comprises at least one sensor molecule chamber, in which the fluorescent sensor molecules are disposed.

Inventive concept 82. The apparatus according to any one of inventive concepts 70-81, wherein the analyte is glucose, and wherein the binding site is for the glucose.

Inventive concept 83. The apparatus according to any one of inventive concepts 70-81, wherein the implantable unit has a volume of no more than 250 mm3.

Inventive concept 84. The apparatus according to any one of inventive concepts 70-81, further comprising packaging, in which the implantable unit is stored before implantation, wherein an external surface of the implantable unit is sterile while stored in the packaging.

Inventive concept 85. The apparatus according to any one of inventive concepts 70-81, further comprising an external reading unit, which is physically separate and distinct from the implantable unit, and which comprises the light sensor.

Inventive concept 86. The apparatus according to any one of inventive concepts 70-81, wherein the implantable unit comprises the light sensor.

Inventive concept 87. The apparatus according to any one of inventive concepts 70-81, wherein the apparatus is configured to measure a temperature at the implantable unit, and wherein the one or more processors are configured to generate calibration information using the measured temperature, and calculate the concentration of the analyte using the calibration information.

There is yet additionally provided, in accordance with an inventive concept 88, apparatus for detecting a concentration of an analyte in a subject, the apparatus comprising:

an implantable unit, which is configured to be implanted in a body of the subject, and comprises fluorescent sensor molecules, each of which comprises a binding site for the analyte, and is configured to emit fluorescent light in response to excitation light; and an external system, which is physically separate and distinct from the implantable unit, and which comprises an external reading unit, which comprises an image sensor, which is configured to generate one or more transdermal images of light passing from the body through skin; and one or more processors, which are configured to:
calculate at least one intensity of the light representing emission from the fluorescent sensor molecules, based on distinguishing between (a) one or more emission areas of the transdermal images corresponding to locations, in one or two dimensions, of the fluorescent sensor molecules, and (b) background areas of the transdermal images, and calculate the concentration of the analyte in the subject based on the at least one intensity of the light emitted from the fluorescent sensor molecules.

Inventive concept 89. The apparatus according to inventive concept 88, wherein the one or more processors are configured to calculate the at least one intensity of the light representing emission from the fluorescent sensor molecules, based on distinguishing between (a) the one or more emission areas of the transdermal images corresponding to locations, in two dimensions, of the fluorescent sensor molecules, and (b) the background areas of the transdermal images.

Inventive concept 90. The apparatus according to inventive concept 89, wherein the image sensor comprises an equally-spaced two-dimensional array of equally-sized sensor elements arranged in a rectangular grid having at least two sensor elements in each direction, and wherein the transdermal images comprise two-dimensional pixelated images.

Inventive concept 91. The apparatus according to inventive concept 90, wherein the image sensor comprises an image sensor selected from the group consisting of: a CCD sensor and a CMOS sensor.

Inventive concept 92. The apparatus according to inventive concept 90, wherein the grid has at least 1024 sensor elements in each direction.

Inventive concept 93. The apparatus according to inventive concept 90, wherein the grid has no more than 32 sensor elements in each direction.

Inventive concept 94. The apparatus according to inventive concept 93, wherein the grid has no more than 16 sensor elements in each direction.

Inventive concept 95. The apparatus according to inventive concept 94, wherein the grid has no more than 4 sensor elements in each direction.

Inventive concept 96. The apparatus according to inventive concept 90, wherein each of the sensor elements has a surface area of at least 1 mm2.

Inventive concept 97. The apparatus according to inventive concept 96, wherein each of the sensor elements has a surface area of at least 4 mm2.

Inventive concept 98. The apparatus according to inventive concept 88, wherein the image sensor comprises at least three sensor elements, which are (a) arranged to sense light from different respective portions of a total field of view of the image sensor, and (b) not arranged as sensor elements of a rectangular grid of sensor elements.

Inventive concept 99. The apparatus according to inventive concept 98, wherein the image sensor comprises at least five sensor elements.

Inventive concept 100. The apparatus according to inventive concept 98, wherein the image sensor comprises no more than 1,024 sensor elements.

Inventive concept 101. The apparatus according to inventive concept 100, wherein the image sensor comprises no more than 64 sensor elements.

Inventive concept 102. The apparatus according to inventive concept 98, wherein at least two of the sensor elements have different respective surface shapes.

Inventive concept 103. The apparatus according to inventive concept 98, wherein at least two of the sensor elements have different respective surface areas.

Inventive concept 104. The apparatus according to inventive concept 103, wherein the one or more processors are configured to calculate the at least one intensity of the light representing emission from the fluorescent sensor molecules, based on distinguishing between (a) the one or more emission areas of the transdermal images corresponding to locations, in two dimensions, of the fluorescent sensor molecules, and (b) the background areas of the transdermal images.

Inventive concept 105. The apparatus according to inventive concept 104, wherein the sensor elements comprise:
one or more central sensor elements, disposed in a central area of the image sensor; and
two or more peripheral sensor elements, disposed generally surrounding the one or more central sensor elements.

Inventive concept 106. The apparatus according to inventive concept 105, wherein at least one of the one or more central sensor elements has a first surface shape, and at least one of the two or more peripheral sensor elements has a second surface shape that is different from the first surface shape.

Inventive concept 107. The apparatus according to inventive concept 106, wherein the one or more central sensor elements comprise exactly one central sensor element.

Inventive concept 108. The apparatus according to inventive concept 105, wherein the one or more central sensor elements have a central sensor surface area in aggregate, and wherein the two or more peripheral sensor elements have a peripheral sensor average surface area, which is less than the central sensor total surface area.

Inventive concept 109. The apparatus according to inventive concept 108, wherein at least one of one or more central sensor elements has a first surface shape, and at least one of the two or more peripheral sensor elements has a second surface shape that is different from the first surface shape.

Inventive concept 110. The apparatus according to inventive concept 108, wherein the one or more central sensor elements comprise exactly one central sensor element.

Inventive concept 111. The apparatus according to inventive concept 108, wherein the one or more processors are configured to use the one or more central sensor elements to predominantly sense the light emitted by the fluorescent sensor molecules, and the two or more peripheral sensor elements to predominantly sense background light not emitted by the fluorescent sensor molecules.

Inventive concept 112. The apparatus according to inventive concept 105, wherein the one or more processors are configured to ascertain the one or more emission areas of the transdermal images corresponding to the locations, in two dimensions, of the fluorescent sensor molecules by ascertaining that the one or more central sensor elements sense predominantly fluorescent light emitted by the fluorescent sensor molecules.

Inventive concept 113. The apparatus according to inventive concept 88, wherein the image sensor comprises at least three sensor elements, which comprise respective sampling circuitries, each of which circuitries is configured to output a value indicative of an intensity of light sensed by the corresponding sensor element.

Inventive concept 114. The apparatus according to inventive concept 113, wherein the external reading unit comprises control electronics, which are configured to simultaneously read the sampling circuitries.

Inventive concept 115. The apparatus according to inventive concept 88, wherein the external reading unit further comprises a user interface, and wherein the one or more processors are configured to:
ascertain, responsively to one or more respective locations of the one or more emission areas of the transdermal images, a desired movement of the external reading unit with respect to an external surface of the skin, and
output, via the user interface, an indication of the desired movement.

Inventive concept 116. The apparatus according to inventive concept 115, wherein the indication of the desired movement includes a direction of the desired movement with respect to the external surface of the skin.

Inventive concept 117. The apparatus according to inventive concept 115, wherein the one or more processors are configured to calculate the at least one intensity of the light representing emission from the fluorescent sensor molecules, based on distinguishing between (a) the one or more emission areas of the transdermal images corresponding to locations, in two dimensions, of the fluorescent sensor molecules, and (b) the background areas of the transdermal images.

Inventive concept 118. The apparatus according to inventive concept 117, wherein the image sensor comprises at least three sensor elements, which comprise:
one or more central sensor elements, which are disposed in a central area of the image sensor; and
two or more peripheral sensor elements, which are disposed generally surrounding the one or more central sensor elements, and wherein the one or more processors are configured to ascertain the desired movement of the external reading unit by ascertaining that a first intensity of light sensed by one or more first ones of the peripheral sensor elements is greater than a second intensity of light sensed by one or more second ones of the peripheral sensor elements.

Inventive concept 119. The apparatus according to inventive concept 118, wherein the one or more central sensor elements have a central sensor total surface area in aggregate, and wherein the two or more peripheral sensor elements have a peripheral sensor average surface area, which is less than the central sensor total surface area.

Inventive concept 120. The apparatus according to inventive concept 118, wherein the one or more processors are configured to ascertain that the desired movement is in a direction from the one or more central sensor elements toward the one or more first ones of the peripheral sensor elements.

Inventive concept 121. The apparatus according to inventive concept 118, wherein the one or more central sensor elements comprise exactly one central sensor element.

Inventive concept 122. The apparatus according to inventive concept 118, wherein at least one of one or more central sensor elements has a first surface shape, and at least one of the two or more peripheral sensor elements has a second surface shape that is different from the first surface shape.

Inventive concept 123. The apparatus according to inventive concept 115, wherein the one or more processors are configured to output the indication upon ascertaining, by the one or more processors, that at least a portion of the fluorescent sensor molecules does not appear in the transdermal images.

Inventive concept 124. The apparatus according to inventive concept 88, wherein the external system further comprises a user interface, and wherein the one or more processors are configured to:
ascertain, responsively to one or more respective locations of the one or more emission areas of the transdermal images, a desired change in disposition of the external reading unit with respect to an external surface of the skin, and
output, via the user interface, an indication of the desired change in disposition.

Inventive concept 125. The apparatus according to inventive concept 124, wherein the change in disposition is a change in position of the external reading unit with respect to the external surface of the skin.

Inventive concept 126. The apparatus according to inventive concept 124, wherein the change in disposition is a change in orientation of the external reading unit with respect to the external surface of the skin.

Inventive concept 127. The apparatus according to inventive concept 124, wherein the one or more processors are configured to output the indication upon ascertaining, by the one or more processors, that at least a portion of the fluorescent sensor molecules does not appear in the transdermal images.

Inventive concept 128. The apparatus according to inventive concept 88, wherein the one or more processors are configured to calculate a background intensity of the light at the emission spectrum at the background areas of the transdermal images, and to correct the calculated at least one intensity of light representing the emission from the fluorescent sensor molecules using the background intensity.

Inventive concept 129. The apparatus according to inventive concept 128, wherein the one or more processors are configured to correct the calculated at least one intensity of the light representing the emission from the fluorescent sensor molecules by subtracting the background intensity from an intensity of the light in the one or more emission areas of the transdermal images.

Inventive concept 130. The apparatus according to inventive concept 88, wherein the one or more processors are configured to use a two-dimensional representation of a spatial distribution of the fluorescent sensor molecules in the implantable unit as a factor in an analysis of the transdermal images for ascertaining the one or more emission areas of the transdermal images.

Inventive concept 131. The apparatus according to inventive concept 130, wherein the fluorescent sensor molecules are distributed within the implantable unit in a repetitive pattern.

Inventive concept 132. The apparatus according to inventive concept 130, wherein the fluorescent sensor molecules are distributed within the implantable unit in a non-uniform spatial distribution.

Inventive concept 133. The apparatus according to inventive concept 130, wherein the fluorescent sensor molecules are distributed within the implantable unit with one or more distinct areas of lower concentration than other areas of the implantable unit in which the fluorescent sensor molecules are distributed.

Inventive concept 134. The apparatus according to inventive concept 130, wherein the fluorescent sensor molecules are distributed within the implantable unit with one or more distinct areas of higher concentration than other areas of the implantable unit in which the fluorescent sensor molecules are distributed.

Inventive concept 135. The apparatus according to inventive concept 88, wherein the implantable unit further comprises at least one sensor molecule chamber, in which the fluorescent sensor molecules are disposed.

Inventive concept 136. The apparatus according to inventive concept 135,
wherein the at least one sensor molecule chamber comprises (a) a substrate, which defines one or more surfaces, and (b) a membrane,
wherein the fluorescent sensor molecules are disposed in the at least one sensor molecule chamber between the membrane and the one or more surfaces of the substrate,
wherein the one or more surfaces have an average reflectivity, and one or more sub-areas of the one or more surfaces have a sub-area reflectivity that is greater than the average reflectivity, and
wherein the one or more processors are configured to use one or more respective locations one or more areas of the transdermal images corresponding to locations, in two dimensions, of the sub-areas as a factor in an analysis of the transdermal images for ascertaining the locations, in two dimensions, of the fluorescent sensor molecules.

Inventive concept 137. The apparatus according to inventive concept 136, wherein the sub-area reflectivity that is at least twice the average reflectivity.

Inventive concept 138. The apparatus according to inventive concept 136, wherein the sub-areas are distributed within the at least one sensor molecule chamber in a repetitive pattern.

Inventive concept 139. The apparatus according to inventive concept 88, wherein the fluorescent sensor molecules are fluorescent sensor proteins.

Inventive concept 140. The apparatus according to any one of inventive concepts 88-139, wherein the analyte is glucose, and wherein the binding site is for the glucose.

Inventive concept 141. The apparatus according to any one of inventive concepts 88-139, wherein each of the fluorescent sensor molecules comprises a donor fluorophore, and an acceptor fluorophore.

Inventive concept 142. The apparatus according to any one of inventive concepts 88-139, wherein the apparatus is configured to measure a temperature at the implantable unit, and wherein the one or more processors are configured to generate calibration information using the measured temperature, and calculate the concentration of the analyte using the calibration information.

Inventive concept 143. The apparatus according to any one of inventive concepts 88-139, wherein the implantable unit has a volume of no more than 250 mm3.

Inventive concept 144. The apparatus according to any one of inventive concepts 88-139, further comprising packaging, in which the implantable unit is stored before implantation, wherein an external surface of the implantable unit is sterile while stored in the packaging.

Inventive concept 145. Apparatus for detecting a concentration of an analyte in a subject, the apparatus comprising an implantable unit, which is configured to be implanted in a body of the subject, and comprises:
fluorescent sensor molecules, each of which comprises (i) a binding site for the analyte, and (ii) at least one fluorescent moiety, which is configured to be excited by light between a first absorption wavelength and a second absorption wavelength greater than the first absorption wavelength; and
an upconversion material, which is disposed in a vicinity of the fluorescent sensor molecules, and which is configured to produce emission of light having an emission peak wavelength between the first absorption wavelength and the second absorption wavelength, upon being excited with light having an excitation peak wavelength that is greater than the second absorption wavelength.

Inventive concept 146. The apparatus according to inventive concept 145, wherein the second absorption wavelength is less than 700 nm, and the excitation peak wavelength is greater than 700 nm.

Inventive concept 147. The apparatus according to inventive concept 146, wherein the excitation peak wavelength is greater than 800 nm.

Inventive concept 148. The apparatus according to inventive concept 147, wherein the first absorption wavelength is greater than 400 nm, and the excitation peak wavelength is less than 1100 nm.

Inventive concept 149. The apparatus according to inventive concept 145, wherein the second absorption wavelength is at least 250 nm less than the excitation peak wavelength.

Inventive concept 150. The apparatus according to inventive concept 145,
wherein the second absorption wavelength is less than 550 nm, and
wherein the excitation peak wavelength is greater than 700 nm.

Inventive concept 151. The apparatus according to inventive concept 145, wherein the upconversion material comprises nanocrystals.

Inventive concept 152. The apparatus according to any one of inventive concepts 145-151, wherein the apparatus further comprises an external system, which is physically separate and distinct from the implantable unit, and which comprises an external reading unit, which comprises a light source that is configured to generate the light having the excitation peak wavelength.

Inventive concept 153. The apparatus according to inventive concept 152, wherein the external reading unit further comprises a light sensor, which is configured to sense fluorescent light emitted from the fluorescent moiety, and wherein the external system further comprises one or more processors, which are configured to (a) drive the light source to generate the light having the excitation peak wavelength, (b) receive, from the light sensor, at least one measurement of the fluorescent light emitted from the fluorescent moiety, and (c) calculate the concentration of the analyte in the subject based on the at least one measurement.

Inventive concept 154. The apparatus according to inventive concept 152, wherein the light source is a first light source, and the excitation peak wavelength is a first excitation peak wavelength, and wherein the external reading unit further comprises a second light source, which is configured to generate light having a second excitation peak wavelength (a) of greater than 700 nm, and (b) that is different from the first excitation peak wavelength.

Inventive concept 155. The apparatus according to inventive concept 154, wherein the fluorescent moiety of each of the fluorescent sensor molecules comprises a donor fluorophore, and an acceptor fluorophore, wherein the light generated by the first light source having the first excitation peak wavelength is appropriate, after upconversion by the upconversion material, for excitation of the donor fluorophore, wherein the light generated by the second light source having the second excitation peak wavelength is appropriate, after upconversion by the upconversion material, for direct excitation of the acceptor fluorophore, and wherein the one or more processors are configured to:
(a) during one or more first time periods: (i) drive the first light source to generate the light having the first excitation peak wavelength, and (ii) receive, from the light sensor, one or more first measurements of the fluorescent light emitted from the acceptor fluorophore,
(b) during one or more second time periods non-overlapping with the first time periods: (i) drive the second light source to generate the light having the second excitation peak wavelength, and (ii) receive, from the light sensor, one or more second measurements of the fluorescent light emitted from the acceptor fluorophore, and
(c) calculate the concentration of the analyte in the subject based on the first and the second measurements.

Inventive concept 156. The apparatus according to inventive concept 155, wherein the acceptor fluorophore is configured to emit fluorescent light having a peak wavelength greater than 625 nm.

Inventive concept 157. The apparatus according to inventive concept 154, wherein the upconversion material comprises:

a first upconversion material, which is more efficient at upconverting the light at the first excitation peak wavelength than the light at the second excitation peak wavelength; and a second upconversion material, which is more efficient at upconverting the light at the second excitation peak wavelength than the light at the first excitation peak wavelength.

Inventive concept 158. The apparatus according to inventive concept 157, wherein the first and the second upconversion materials comprise respective nanocrystals of different types.

Inventive concept 159. The apparatus according to any one of inventive concepts 145-151, wherein each of the fluorescent sensor molecules comprises exactly one fluorescent moiety.

Inventive concept 160. The apparatus according to any one of inventive concepts 145-151, wherein each of the fluorescent sensor molecules comprises exactly two fluorescent moieties.

Inventive concept 161. The apparatus according to any one of inventive concepts 145-151, wherein the implantable unit further comprises a dichroic mirror, which is configured to allow passage therethrough of the light at the excitation peak wavelength, and to reflect and inhibit passage therethrough of the light at the emission peak wavelength.

There is also provided, in accordance with an inventive concept 162, a method for detecting a concentration of an analyte in a subject, the method comprising:

implanting, in a body of the subject, an implantable unit, which comprises:
(a) fluorescent sensor molecules, each of which comprises (i) a binding site for the analyte, and (ii) at least one fluorescent moiety configured to emit fluorescent light; and
(b) an implantable-unit light source that is configured to generate light having an illumination peak wavelength appropriate for excitation of the fluorescent moiety;

placing an external reading unit of an external system above skin of the subject, wherein the external reading unit comprises a light sensor, which is configured to sense fluorescent light emitted from the fluorescent moiety having an emission peak wavelength, wherein the emission peak wavelength is between 100 and 500 nm greater than the illumination peak wavelength, and wherein the external system is physically separate and distinct from the implantable unit; and activating one or more processors of the external system to: (1) drive the implantable-unit light source to generate the light, (2) receive, from the light sensor, at least one measurement of the fluorescent light emitted from the fluorescent moiety, and (3) calculate the concentration of the analyte in the subject based on the at least one measurement.

The present invention will be more fully understood from the following detailed description of embodiments thereof, taken together with the drawings, in which:

BRIEF DESCRIPTION OF THE DRAWINGS

FIG. 2 is a schematic illustration of another system for transdermal detection of a concentration of an analyte in a subject, in accordance with an application of the present invention;

FIGS. 10A-E are schematic illustrations of configurations of an image sensor, in accordance with respective applications of the present invention;

FIG. 11 is a schematic illustration of another system for transdermal detection of a concentration of an analyte in a subject, in accordance with an application of the present invention; and FIG. 12 is a schematic illustration of yet another system for transdermal detection of a concentration of an analyte in a subject, in accordance with an application of the present invention.

DETAILED DESCRIPTION OF APPLICATIONS

Figure 1:
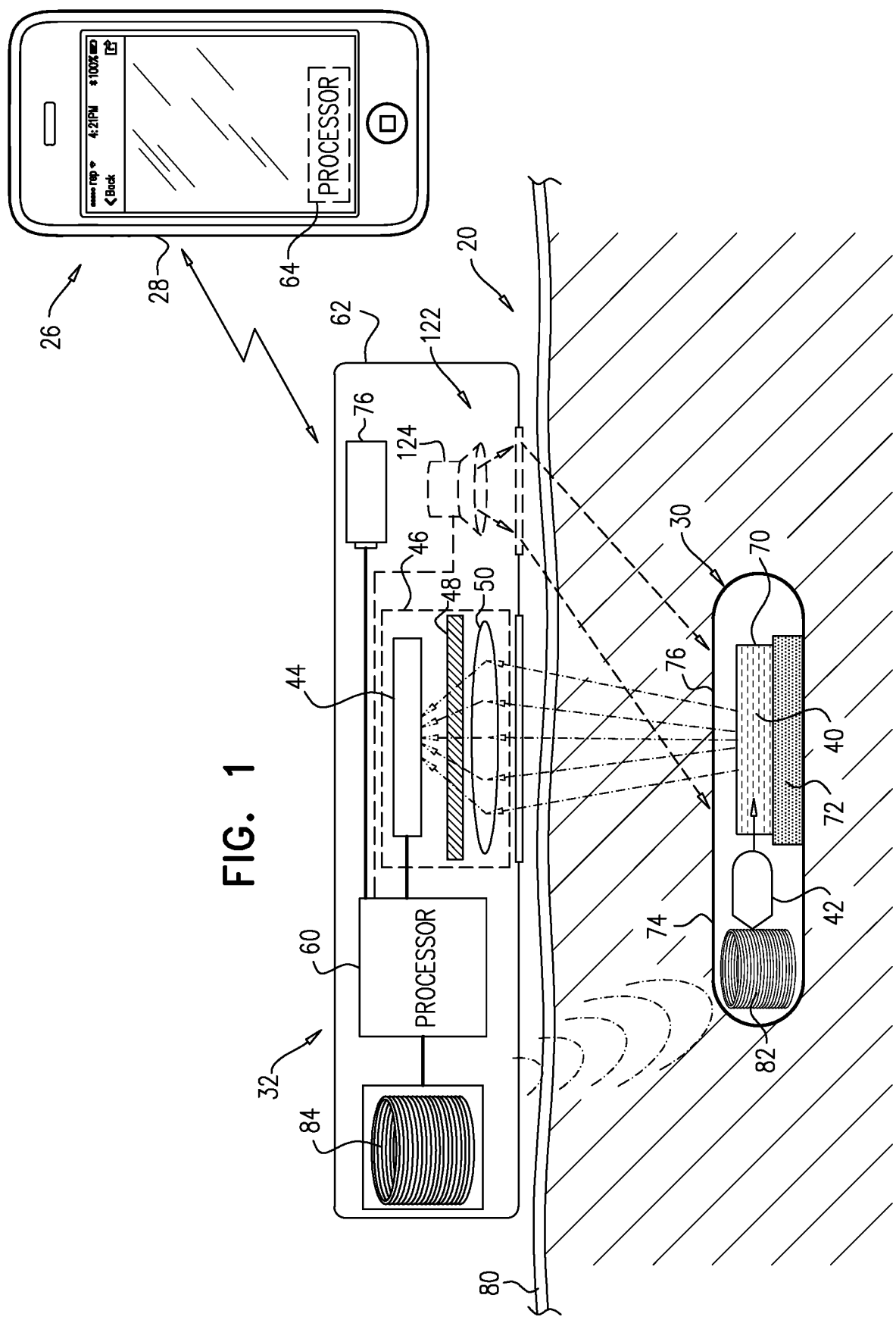
FIG. 1 is a schematic illustration of a system for transdermal detection of a concentration of an analyte in a subject, in accordance with an application of the present invention.

FIG. 1 is a schematic illustration of a system 20 for transdermal detection of a concentration of an analyte in a subject, in accordance with an application of the present invention. System 20 comprises an implantable unit 30, which is configured to be implanted in a body of the subject, and an external system 26, which is physically separate and distinct from implantable unit 30. External system 26 comprises an external reading unit 32 and, optionally, an external monitor unit 28.

Implantable unit 30 comprises fluorescent sensor molecules 40, each of which comprises a binding site for the analyte, and at least one fluorescent moiety. A number of fluorescent compounds have been described in the literature for the purpose of analyte sensing, including different fluorescent reporters, e.g., Concanavalin-A, fluorescein, and fluorophores derived from various marine fauna, such as GFP and its derivatives. The analyte sensing is based on different mechanisms, including, e.g., specific enzymes such as glucose oxidase and glucose dehydrogenase, and bacterial-driven analyte-binding proteins (see, for example, Pickup J C et al., "Fluorescence-based glucose sensors," Biosensors and Bioelectronics 20 (2005) 2555-2565 (available online Nov. 21, 2004)). For some applications, the analyte is glucose, and the binding site is for glucose.

For some applications, fluorescent sensor molecules 40 comprise Fluorescence Resonance Energy Transfer (FRET) sensor molecules. The fluorescent moiety of each of fluorescent sensor molecules 40 comprises a donor fluorophore and an acceptor fluorophore, as well as an analyte-binding moiety which reversibly changes its shape following specific binding to the target analyte. Typically, the acceptor fluorophore of the FRET sensor molecules is selected such that a substantial portion of the light emitted by the acceptor fluorophore is able to penetrate through at least 0.5 mm, e.g., at least 1 mm, such as at least 2 mm of tissue (which typically includes skin 80). For example, the acceptor fluorophore may be selected such that a substantial portion (e.g., at least 10%, such as at least 20%, e.g., at least 40%) of the emission spectrum of the acceptor fluorophore is at a wavelength greater than 625 nm, e.g., greater than 650 nm, greater than 675 nm, or greater than 700 nm. Typically, the emission peak wavelength corresponds approximately to this wavelength of the substantial portion of the emission spectrum, such that the emission peak wavelength of the acceptor fluorophore is greater than 600 nm, e.g., greater than 625 nm, greater than 650 nm, greater than 675 nm, or greater than 700 nm. For example, the emission peak may be between 625 nm and 675 nm.

For some applications, the system is configured to excite the FRET sensor molecules with a single excitation frequency, and to measure the resulting emission from the donor and the acceptor at two different frequencies, respectively, as is standard in the FRET art. For other applications, the system is configured to excite the FRET sensor molecules at two different excitation frequencies, and to measure the resulting emission from the FRET sensor molecules at a single acceptor emission frequency, such as described hereinbelow with reference to FIGS. 1 and 2.

For some applications, the FRET sensor molecules comprise a yellow fluorophore having substantial emission in the range 500-650 nm, which is suitable for exciting red or far-red fluorophores having an excitation spectrum substantially at the same wavelength range.

For example, the acceptor fluorophore may comprise a far-red fluorophore, such as mKate, mKate2, mRuby2, mCardinal, mNeptune1, mNeptune2, or mNeptune2.5, as are known in the art.

For some applications, the donor fluorophore comprises a yellow fluorophore, such as EYFP, Citrine, tagYFP, mVenus, mClover, mNeon, or mBanana, as are known in the art.

For some applications, each of the FRET sensor molecules is a FRET protein, which comprises (a) a green or yellow fluorescent protein as the donor fluorophore, (b) a red or infrared fluorescent protein as the acceptor fluorophore, with at least 10%, such as at least 20%, of the emission of the acceptor at wavelengths greater than 650 nm, and (c) a glucose binding protein having a dissociation factor for glucose, for example, with a Kd in the range of 2 to 10 mM, enabling sensitive measurement to be taken in the physiological range of glucose concentrations.

For other applications, each of fluorescent sensor molecules 40 comprises exactly one fluorescent moiety, rather than a FRET molecule. For some applications, each of fluorescent sensor molecules 40 comprises exactly two fluorescent moieties.

For some applications, implantable unit 30 further comprises an implantable-unit light source 42. Typically, implantable-unit light source 42 is configured to generate light having a first illumination peak wavelength that is greater than 300 nm and less than 600 nm, typically less than 550 nm (e.g., less than 525 nm, such as less than 500 nm, e.g., about 470 nm) and appropriate for excitation of the fluorescent moiety. Upon excitation, the fluorescent moiety emits fluorescent light having an emission peak wavelength. Alternatively or additionally, for some applications, the emission peak wavelength is between 100 and 500 nm greater than the first illumination peak wavelength, such as between 100 and 250 nm greater than the first illumination peak wavelength. For some applications, the emission peak wavelength is at least 150 nm greater than the first illumination peak wavelength.

For some applications, implantable-unit light source 42 comprises a laser; typically, the laser generates the light at substantially a single wavelength, in which case the single wavelength is the first illumination peak wavelength. Alternatively, implantable-unit light source 42 comprises a light emitting diode (LED); typically, the first illumination peak wavelength of the LED is less than 550 nm, e.g., less than 525 nm, such as less than 500 nm, and the full-width-half-maximum of the LED emission spectrum is typically between 10-40 nm.

Implantable unit 30 typically comprises an enclosure 74, in which the other components of the implantable unit are disposed. Enclosure 74 has at least one transparent surface 76, which allows the light generated by fluorescent sensor molecules 40 to exit the implantable unit, and, for applications in which one or more external-unit light sources are provided, for light generated by the external-unit light source(s) to enter the implantable unit. Typically, implantable unit 30 has a volume of no more than 250 mm3, such as less than 100 mm3, e.g., less than 75 mm3. For some applications, packaging is provided, in which implantable unit 30 is stored before implantation, and an external surface of implantable unit 30 is sterile while stored in the packaging.

External reading unit 32 comprises a light sensor 44, which is configured to sense fluorescent light emitted from the fluorescent moiety. For some applications, external reading unit 32 comprises an optical unit 46, which comprises light sensor 44 and additional optical components, such as at least one filter 48 and/or at least one lens 50. For some applications, such as described hereinbelow with reference to FIGS. 10A-E, light sensor 44 comprises a plurality of sensor elements aligned toward respective portions of the total field of view of optical unit 46 (optionally, though the same or different optical elements), such as an array of sensor elements configured to generate an image of the fluorescent signal, such as described hereinbelow with reference to FIGS. 10A and 10B. For some applications, implantable unit 30 comprises light sensor 44 (configuration not shown).

External system 26 further comprises one or more processors, which are configured to: (i) receive, from light sensor 44, at least one measurement of the fluorescent light emitted from the fluorescent moiety, and (ii) calculate the concentration of the analyte in the subject based on the at least one measurement. Optionally, the one or more processors are configured to drive implantable-unit light source 42 to generate the light. For applications in which implantable unit 30 comprises minimal or no circuitry, the one or more processors drive implantable-unit light source 42 to generate the light substantially without any intervening processing by the implantable unit, i.e., the one or more processors substantially directly drive the implantable-unit light source. For other applications in which implantable unit 30 comprises more extensive circuitry (such as a processor), the one or more processors of external system 26 drive the circuitry of the implantable unit (such as by transmitting energy or data to the circuitry) to activate implantable-unit light source 42 to generate the light. (These two ways of driving are applicable to all configurations described herein in which the one or more processors of the external system drive the implantable unit and/or implantable-unit light sources to generate light.) Alternatively, the implantable unit is configured to periodically generate the light, without triggering and without data communication from the external reading unit.

For some applications, external reading unit 32 comprises a housing 62, which contains both light sensor 44 and at least one processor 60 of the one or more processors of external system 26, such as shown in FIG. 1. Processor 60 comprises digital and/or analog components, and typically comprises one or more integrated circuits. Alternatively or additionally, for other applications, at least one processor 64 of the one or more of the processors are located outside of housing 62 of external reading unit 32, in external monitor unit 28 of external system 26, which may comprise, for example, a generic computer system, such as a conventional desktop computer, laptop computer, smart phone, tablet computer, or other computer which comprises memory and/or a display. External monitor unit 28 unit typically comprises software for carrying out at least a portion of the functions prescribed by the present invention. This software may be downloaded to the computer in electronic form over a network, for example, or it may alternatively be supplied on tangible media, such as CD-ROM. For some applications, the one or more processors comprise the at least one processor 60, which is located in the external reading unit, and the at least one processor 64 that is located outside of the external reading unit in the external monitor unit; for these applications, functions of the one or more processors described herein, and recited in the claims herein, may optionally be distributed among the at least one processor 60 and the at least one processor 64. For example, the at least one processor 60 of the external reading unit may be configured to receive the measurements of light emitted from the fluorescent moiety, and the at least one processor 64 of external monitor unit 28 may be configured to calculate the concentration of the analyte. For applications in which external monitor unit 28 is provided, external reading unit 32 is in data communication with external monitor unit 28, such as via one or more wires, wirelessly, and/or over at least one network, e.g., a local network and/or a wide area network, such as the Internet.

For some applications, system 20 is configured to measure the temperature at the position of the implantable unit, and the one or more processors are configured to generate calibration information using the measured temperature, and calculate the concentration of the analyte using the calibration information, such as described hereinbelow with reference to FIGS. 1-12. Because sensor protein binding properties and optical response may depend on temperature, and temperature in the tissue may change over time, this calibration may substantially enhance the measured accuracy. The calibration process may rely on either prior knowledge of the temperature sensitivity of the sensor protein, or may be based on a learning system that uses data collected during the calibration process and/or during continuous use of the system. Additionally, the system may be configured to perform a measurement only if the sensor temperature is between upper and lower temperature limit values. Providing such limits may avoid producing erroneous measurements which are taken beyond the established accuracy range of the temperature calibration. For example, the upper temperature limit value may be at least 39 degrees C., e.g., at least 42 degrees C., and the lower temperature limit value may be no more than 32 degrees C., e.g., no more than 28 degrees C.

For some applications, implantable unit 30 further comprises at least one sensor molecule chamber 70, in which fluorescent sensor molecules 40 are disposed. For some applications, such as described hereinbelow with reference to FIGS. 3A-C, 5, and 7, implantable unit 30 further comprises at least one cell chamber 86, typically adjacent to the at least one sensor molecule chamber 70. The cell chamber contains live cells which are engineered to produce and secrete the fluorescent sensor molecules, for example, as described in WO 2006/006166 to Gross et al., which is incorporated herein by reference. In these applications, implantable unit 30 typically further comprises a membrane 72 permeable to nutrients; membrane 72 optionally implements techniques described in WO 2006/006166 to Gross et al. and/or WO 2014/102743 to Brill et al., which are incorporated herein by reference. For other applications, implantable unit 30 comprises at least one chamber that serves as both sensor molecule chamber 70 and cell chamber 86; in other words, the cells secrete the fluorescent sensor molecules into the chamber, and the fluorescent sensor molecules remain in the chamber with the cells. For other applications, fluorescent sensor molecules 40 are disposed on a surface of enclosure 74 of implantable unit 30, rather than in a chamber.

Implantable unit 30 is typically implanted between 0.5 mm and 3 mm below the surface of skin 80 of the subject, for example in the dermis, in fat layers below the dermis, or subcutaneously, typically above muscle. During measurement of the concentration of the analyte, external reading unit 32 is placed above skin 80 (either in or not in contact with the external surface of the skin). External reading unit 32 performs optical reading of the light emitted from the implanted unit through the skin, and optionally provides measurement data to external monitor unit 28, for example by wireless transmission, e.g., using Wi-Fi, Bluetooth, or an IR link. The external reading unit may perform the transmission generally continuously, after each measurement point, and/or by request, in which case data is stored in the external reading unit until requested by the external monitor unit.

The external reading unit may be attached to the body, e.g., by adhesive tape; loosely placed on the body, e.g., as a wristwatch; or manually placed on the skin surface for each measurement.

External system 26 (e.g., external monitor unit 28 and/or external reading unit 32) may perform calibration of the raw data to enable accurate measurement of the analyte concentration. The external monitor unit and/or the external reading unit perform and provide numerical and visual display to the user, and/or provide calibrated data to one or more other systems, such as to a therapeutic system, e.g., a controller of an artificial pancreas system, as known in the art.

For some applications, external reading unit 32 and external monitor unit 28 are provided in a single, unified unit. This configuration may be particularly useful if measurements are taken on-demand whenever the user brings the external reading unit sufficiently close to the implantable unit.

For some applications, implantable unit 30 further comprises a wireless energy receiver 82, which is configured to receive electromagnetic radiation for powering implantable-unit light source 42. Wireless energy receiver 82 is electrically coupled to implantable-unit light source 42. For some applications, the wireless energy receiver, when it receives the electromagnetic radiation, activates the implantable-unit light source. For some applications, wireless energy receiver 82 comprises a coil or an antenna. For some applications, external reading unit 32 comprises a wireless energy transmitter 84, which is configured to transmit the electromagnetic radiation, as is typically done in RFID systems, or, e.g., to transmit power by magnetic induction. For some applications, the wireless energy transmitter comprises a coil or an antenna. For some applications, external reading unit 32 transmits power to implantable unit 30 whenever a measurement of the concentration of the analyte is required.

For some application, the one or more processors are configured to drive implantable-unit light source 42 (and/or the other light sources described herein) to generate the light in pulses. Each of the pulses typically has a duration of at least 0.01 msec, no more than 10 msec, and/or between 0.01 and 10 msec, such as between 1 and 3 msec.

Alternatively, for some applications, the implantable unit is configured to illuminate the fluorescent sensor at a constant repetition interval without requiring an external trigger and without data communication from the external reading unit. In this implementation, the implantable unit may comprise a capacitor or battery (not shown) to store energy between the time of charging and a later time in which illumination is performed. The external charging of the implantable unit may suffice in this case for multiple illumination cycles and need not be synchronized with the measurements.

Reference is still made to FIG. 1, and is additionally made to FIG. 2, which is a schematic illustration of a system 120 for transdermal detection of a concentration of an analyte in a subject, in accordance with an application of the present invention. System 120 may implement any of the techniques described herein regarding system 20, described hereinabove with reference to FIG. 1. Like reference numeral refer to like elements. System 120 comprises an implantable unit 130 and an external reading unit 132.

For some applications, fluorescent sensor molecules 40 comprise FRET sensor molecules. The fluorescent moiety of each of fluorescent sensor molecules 40 comprises a donor fluorophore and an acceptor fluorophore, as well as an analyte-binding moiety which reversibly changes its shape following specific binding to the target analyte.

For some applications, implantable-unit light source 42 is a first implantable-unit light source 42, which is configured to generate light at the first illumination peak wavelength appropriate for excitation of the donor fluorophore, while minimizing the direct excitation of the acceptor fluorophore. For some of these applications, the system (system 20 or 120) further comprises a second light source 122, which is configured to generate light at a second illumination peak wavelength appropriate for direct excitation of the acceptor fluorophore, while optionally minimizing the excitation of the donor fluorophore. For some applications, second light source 122 comprises a second external-unit light source 124, which external reading unit 132 comprises, such as shown in FIG. 1. For other applications, second light source 122 comprises a second implantable-unit light source 126, which implantable unit 130 comprises, such as shown in FIG. 2. For all applications in the present application in which one or more external-unit light sources are provided, associated optics may be provided, such as a lens 380, as shown by way of example in FIGS. 6 and 9, described hereinbelow.

For some applications, the one or more processors are configured to:
during one or more first time periods: (a) drive first implantable-unit light source 42 to generate light having the first illumination peak wavelength, appropriate for the excitation of the donor fluorophore, and (b) receive, from light sensor 44, one or more first measurements (typically of the total energy or peak intensity) of the fluorescent light emitted from the acceptor fluorophore, optionally after having passed through the at least one filter 48. As a result, a significant portion of the signal is related to the FRET effect and is thus sensitive to the concentration of the analyte. Typically, the emission peak wavelength emitted from the acceptor fluorophore is selected to have good transmission through tissue including skin 80, and thus is typically in the red or infrared portions of the spectrum, e.g., between 650 and 1250 nm. Typically, the at least one filter 48 is configured to pass light having a wavelength between 650 nm and 800 nm such that the majority of the light emitted by the acceptor fluorophore and transmitted through skin 80 is able to pass, while other wavelengths, which may contain background light, are blocked by the filter;

during one or more second time periods non-overlapping with the first time periods: (a) drive second light source 122 to generate the light having the second illumination peak wavelength, appropriate for direct excitation of the acceptor fluorophore, and (b) receive, from light sensor 44, one or more second measurements (typically of the total energy or peak intensity) of the fluorescent light emitted from the acceptor fluorophore, optionally after having passed through the at least one filter 48. These second measurements are thus largely insensitive of the concentration of the analyte. However, these second measurements provide an optimal reference, because they of the same wavelength as the first measurements, and are dependent in the same way as the first measurement on a number of factors, including (a) the concentration of the FRET sensor molecules, (b) transmission of the optical signal through tissue including skin 80 and/or other intervening material, and through the same optical components of the system, and (c) sensor sensitivity; and calculate the concentration of the analyte in the subject based on the first and the second measurements, such as by calculating the ratio of the first and the second measurements. Typically, the one or more processors are configured to apply calibration procedures to both the first and the second measurements, including, for example, background subtraction and/or non-linearity correction. For some applications, the one or more processors calculate the concentration by dividing the first measurements (optionally calibrated) by the second measurements (optionally calibrated). The ratio thus obtained is thus corrected for common factors, including the amount of the FRET sensor molecules in the implantable unit, their distribution, transmission of the full optical path, including tissue (including skin 80), as well as the response of the collection channel. Differences between the two measurements that relate to the different excitation conditions, e.g., wavelength, optical path, and transmission through the tissue (including skin), are either assumed constant or otherwise calibrated.

Typically, the same collecting optics and light sensor is used to measure the emission from the acceptor fluorophore during the first and the second time periods.

In contrast, standard FRET measurements are made by illuminating the FRET sensor at a single excitation wavelength, which excites the donor fluorophore, and two simultaneous measurements of fluorescence emitted from both the acceptor and the donor fluorophores.

Typically, the emission peak wavelength of the acceptor fluorophore is at least 625 nm (in the red or infrared portion of the spectrum), which has better transmission through skin 80 and other tissue than the lower-wavelength emissions from the donor fluorophore in conventional FRET techniques. Thus, this technique, unlike convention FRET measurement techniques, enables all signal collection to be done under optimal tissue transmission conditions.

For some applications, first light source 42 generates light having the first illumination peak wavelength that is greater than 300 nm and less than 550 nm, e.g., less than 525 nm, such as less than 500 nm. Because light in this range of wavelengths is generated by first implantable-unit light source 42, the light does not need to pass through skin 80 or other tissue. Light in this range of wavelengths does not have good effective penetration through tissue including skin, and thus the light reaching the implant would be highly attenuated if generated by an external light source.

For some applications, second light source 122 generates light having the second illumination peak wavelength that is greater than 300 nm and less than 650 nm.

For some applications, implantable unit 30 is configured to drive implantable-unit light source 42 to generate light at the first illumination peak wavelength (appropriate for excitation of the donor fluorophore), in a train of pulses beginning concurrently with receipt of the electromagnetic radiation received by wireless energy receiver 82, and continuing as long as energy transmission continues. For configurations in which implantable-unit light source 42 comprises a plurality of light sources 42, e.g., two or three light sources that generate light at different respective illumination peak wavelengths, the train of pulses may comprise respective trains of pulses generated during respective sequential time periods by the respective light sources. Implantable unit 30 may be configured to repeat the full train of pulses generated by all of the light sources periodically as long as the energy transmission continues. Alternatively, implantable unit 30 may be configured to continue the train of pulses generated at the first illumination peak wavelength (appropriate for excitation of the donor fluorophore), such as by first implantable-unit light source 42, as long as the energy transmission continues. (It may be appropriate to illuminate the donor fluorophore for a greater amount of time than the acceptor fluorophore, because the emission using excitation at the first illumination peak wavelength typically has the smallest signal-to-noise ratio.

Figure 3A:
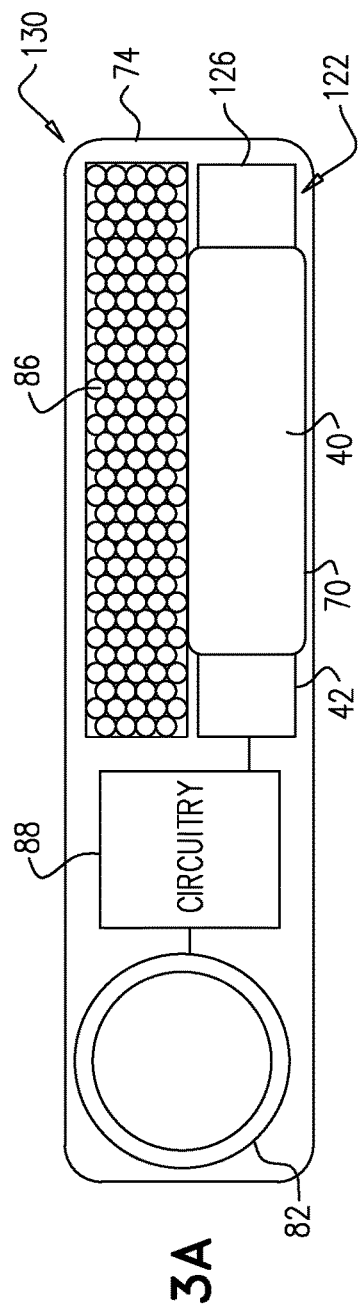
FIGS. 3A-C are schematic top-view illustrations of several configurations of an implantable unit of the system of FIG. 2, in accordance with respective applications of the present invention.
Figure 3B:
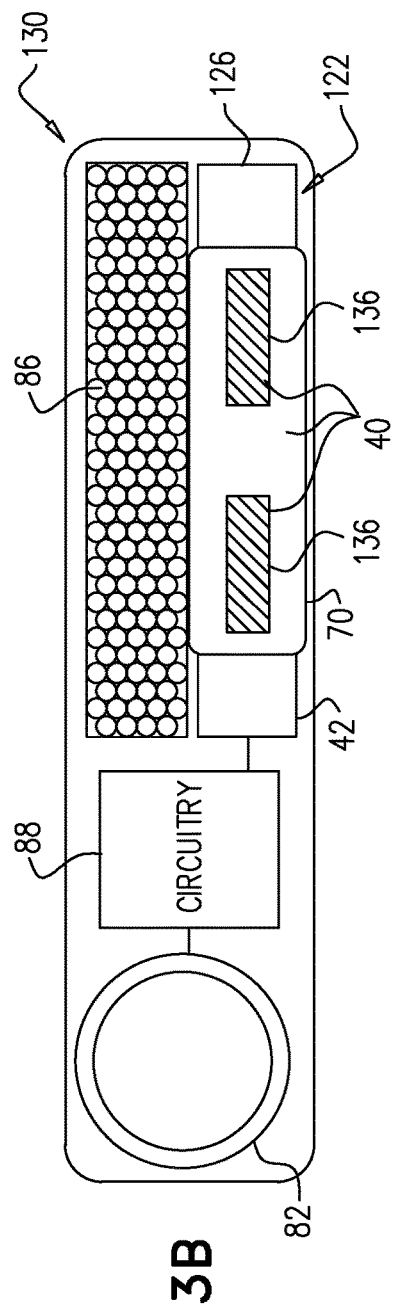
Figure 3C:
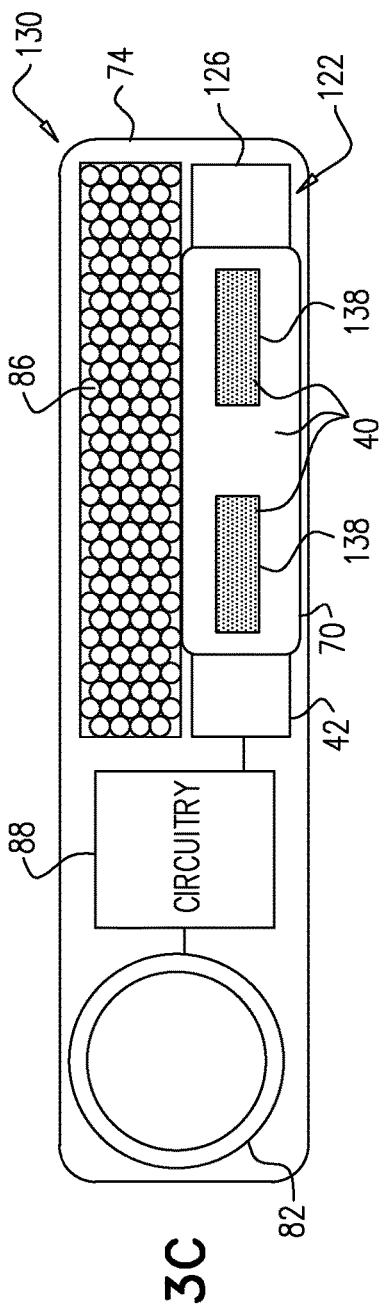

Reference is made to FIGS. 3A-C, which are schematic top-view illustrations of several configurations of implantable unit 130, in accordance with respective applications of the present invention. Each of fluorescent sensor molecules 40 comprises a binding site for the analyte, and is configured to emit fluorescent light having at least one emission peak wavelength in response to excitation light. For some of these applications, fluorescent sensor molecules 40 are fluorescent sensor proteins, and implantable unit 30 further comprises the at least one cell chamber 86, which contains live cells genetically engineered to produce the proteins in situ, such as by continuously expressing the proteins. For example, the proteins may comprise FRET proteins having FRET complexes. For some applications, the cells secrete the sensor protein, while for other applications, the cells express but do not secrete a sensor protein. The at least one cell chamber 86 may be implemented using techniques described in WO 2006/006166 to Gross et al. and/or WO 2014/102743 to Brill et al., mutatis mutandis. For some applications, implantable unit 30 comprises circuitry, which receives power from wireless energy receiver 82, and drives first and second implantable-unit light sources 42 and 126 to generate light. For some applications, implantable unit 30 may be pre-filled with any fluorescent reporter and/or is repeatedly re-filled with a fluorescent reporter, e.g., through a dedicated filling port.

Figure 4:
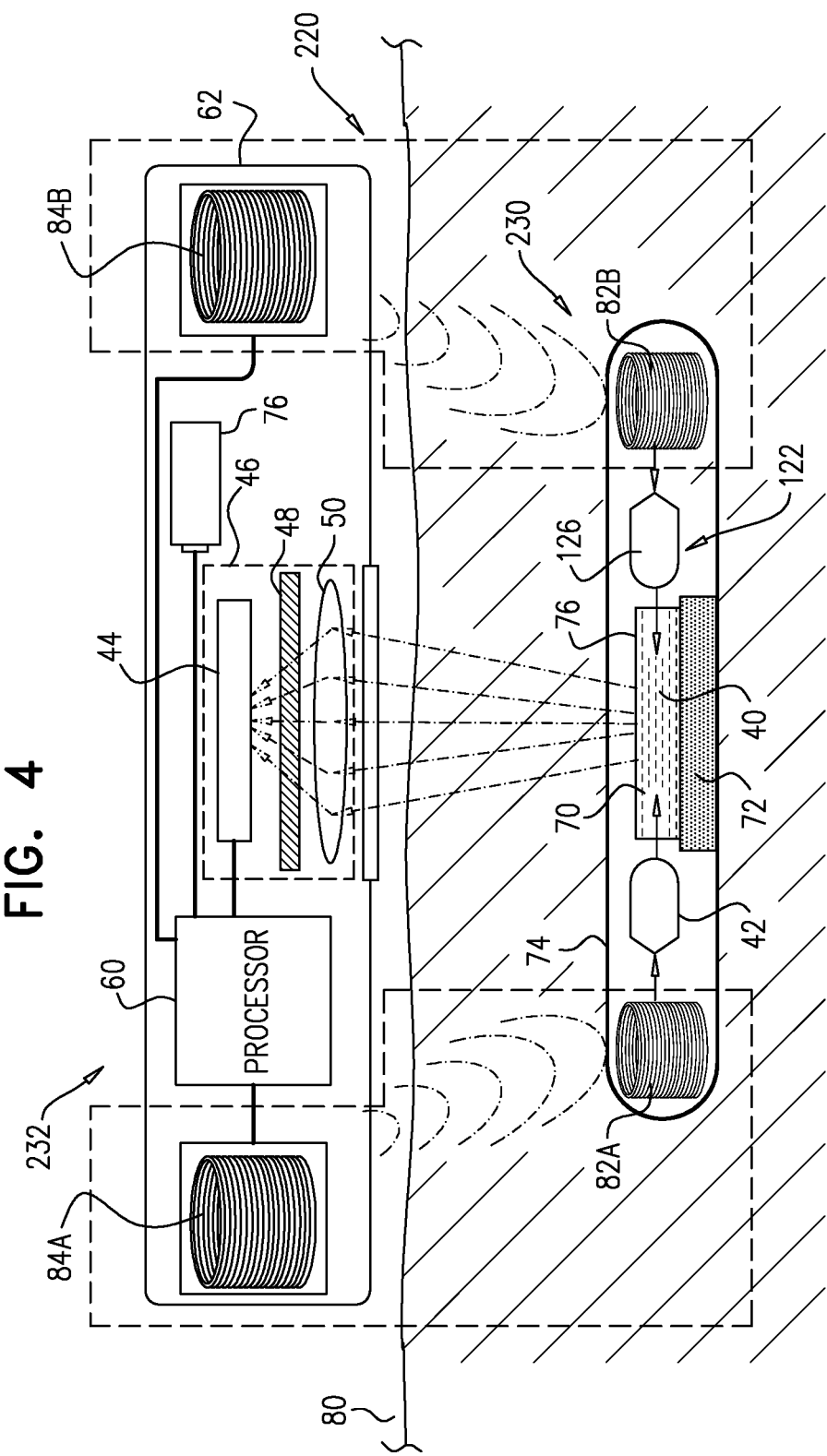
FIG. 4 is a schematic illustration of yet another system for transdermal detection of a concentration of an analyte in a subject, in accordance with an application of the present invention.
Figure 5:
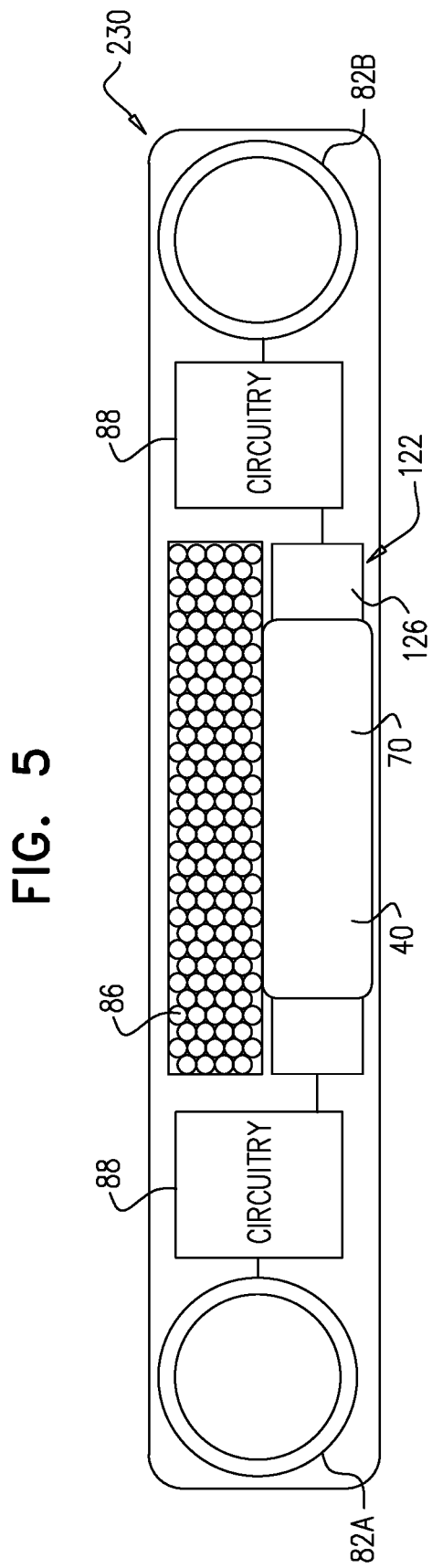
FIG. 5 is a schematic top-view illustration of an implantable unit of the system of FIG. 4, in accordance with an application of the present invention.

Reference is now made to FIG. 4, which is a schematic illustration of a system 220 for transdermal detection of a concentration of an analyte in a subject, in accordance with an application of the present invention. Reference is also made to FIG. 5, which is a schematic top-view illustration of an implantable unit 230 of system 220, in accordance with an application of the present invention. System 220 further comprises an external reading unit 232. System 220 may implement any of the techniques described herein regarding system 20 or system 120, described hereinabove with reference to FIGS. 1 and 2, respectively. Like reference numeral refer to like elements.

In this configuration, implantable unit 230 comprises at least one first implantable-unit light source 42 and at least one second implantable-unit light source 126. External reading unit 232 is configured to drive first and second implantable-unit light sources 42 and 126 to generate the light having the first and the second illumination peak wavelengths, respectively, by transmitting electromagnetic radiation at first and second different RF frequencies, respectively. As mentioned above, the first illumination peak wavelength is appropriate for excitation of the donor fluorophore, while minimizing the direct excitation of the acceptor fluorophore, and the second illumination peak wavelength is appropriate for direct excitation of the acceptor fluorophore, while optionally minimizing the excitation of the donor fluorophore.

For some applications, implantable unit 230 comprises first and second wireless energy receivers 82A and 82B, which are configured to receive the electromagnetic radiation at the first and the second RF frequencies, respectively. First and second wireless energy receivers 82A and 82B are electrically coupled to first and second implantable-unit light sources 42 and 126, respectively, such that the first and second wireless energy receivers, when they receive the electromagnetic radiation, activate the first and second light sources, respectively. External reading unit 232 thus transmits the electromagnetic radiation at the first RF frequency in order to activate first implantable-unit light source 42, and at the second RF frequency in order to activate second implantable-unit light source 126. Typically, first and second wireless energy receivers 82A and 82B comprise respective different sized coils and/or different capacitors in order to tune the receivers to their respective RF frequencies. This configuration simplifies implantable unit 230, because only minimal (possible discrete electronics) or no circuitry is needed to activate the implantable-unit light sources. In this configuration, the length and optionally also the power of the illumination is directly controlled by the energy pulses transmitted by external reading unit 232, allowing direct control by the one or more processors to compensate for variations in signal strength. Such variations may result, for example, from variations in the concentration of fluorescent sensor molecules 40 from implantable unit to implantable unit or as a function of time.

For some applications, external reading unit 232 comprises first and second wireless energy transmitters 84A and 84B, which are configured to transmit the electromagnetic radiation at the first and the second RF frequencies, respectively, and thus activate first and second implantable-unit light sources 42 and 126, respectively. Typically, first and second wireless energy transmitter 84A and 84B comprise respective different sized coils and/or different capacitors in order to tune the transmitters to their respective RF frequencies, thereby eliminating crosstalk between the transmitters. Alternatively, external reading unit 232 comprises a wireless energy transmitter that is configured transmit at the first and the second RF frequencies under the control of the one or more processors, for example comprising a single coil.

Figure 6:
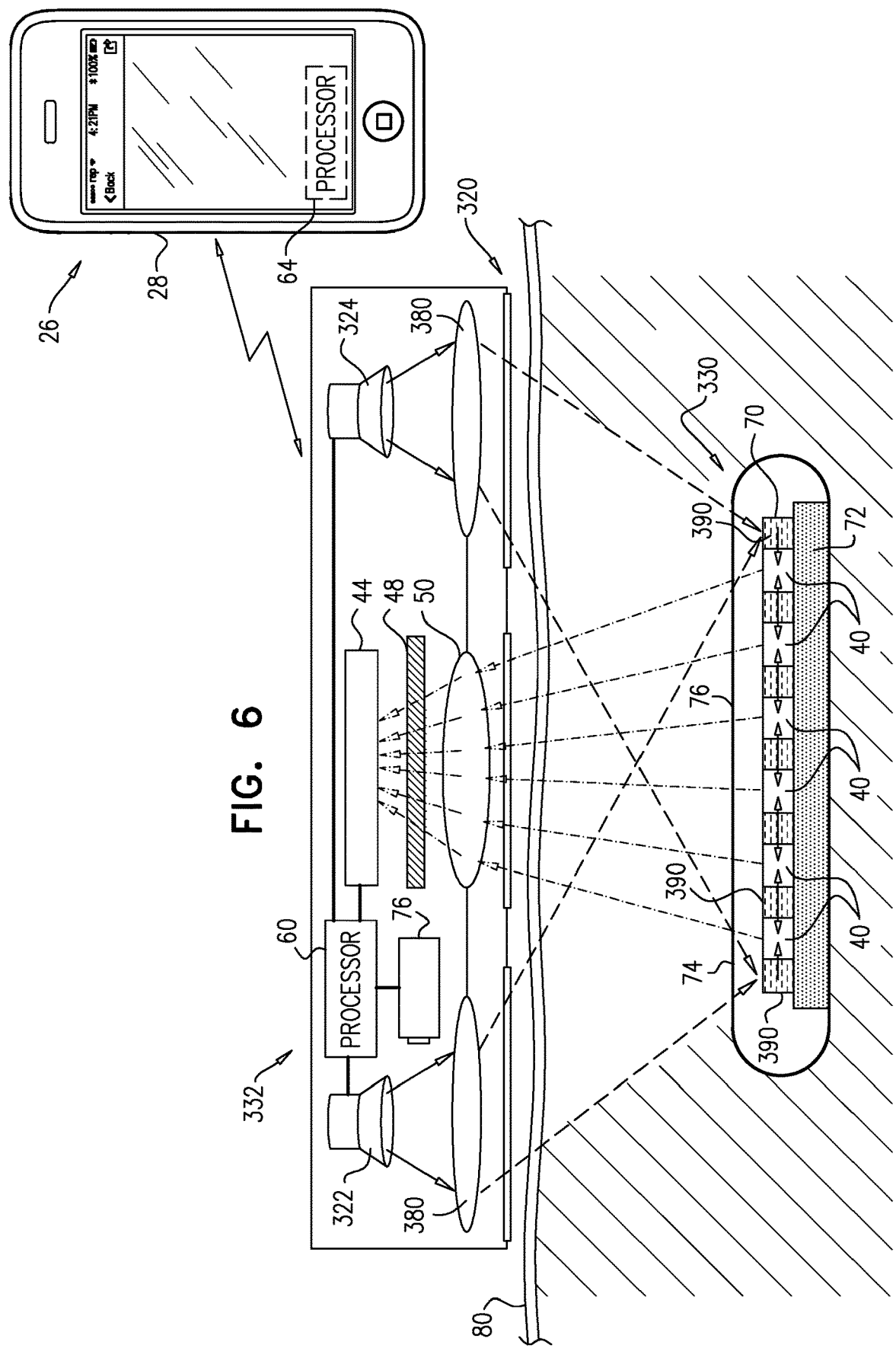
FIG. 6 is a schematic illustration of a still another system for transdermal detection of a concentration of an analyte in a subject, in accordance with an application of the present invention.
Figure 7:
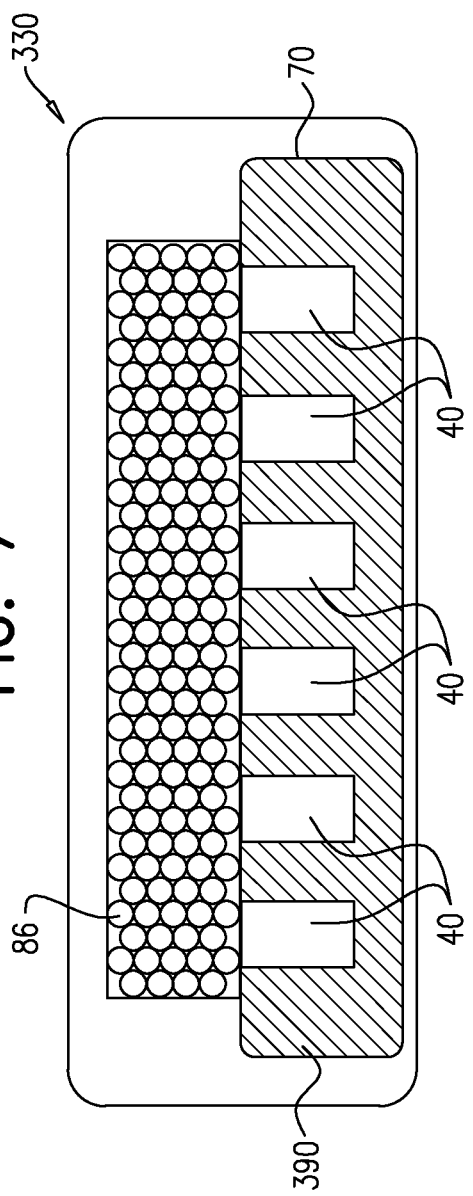
FIG. 7 is a schematic top-view illustration of an implantable unit of the system of FIG. 6, in accordance with an application of the present invention.
Figure 9:
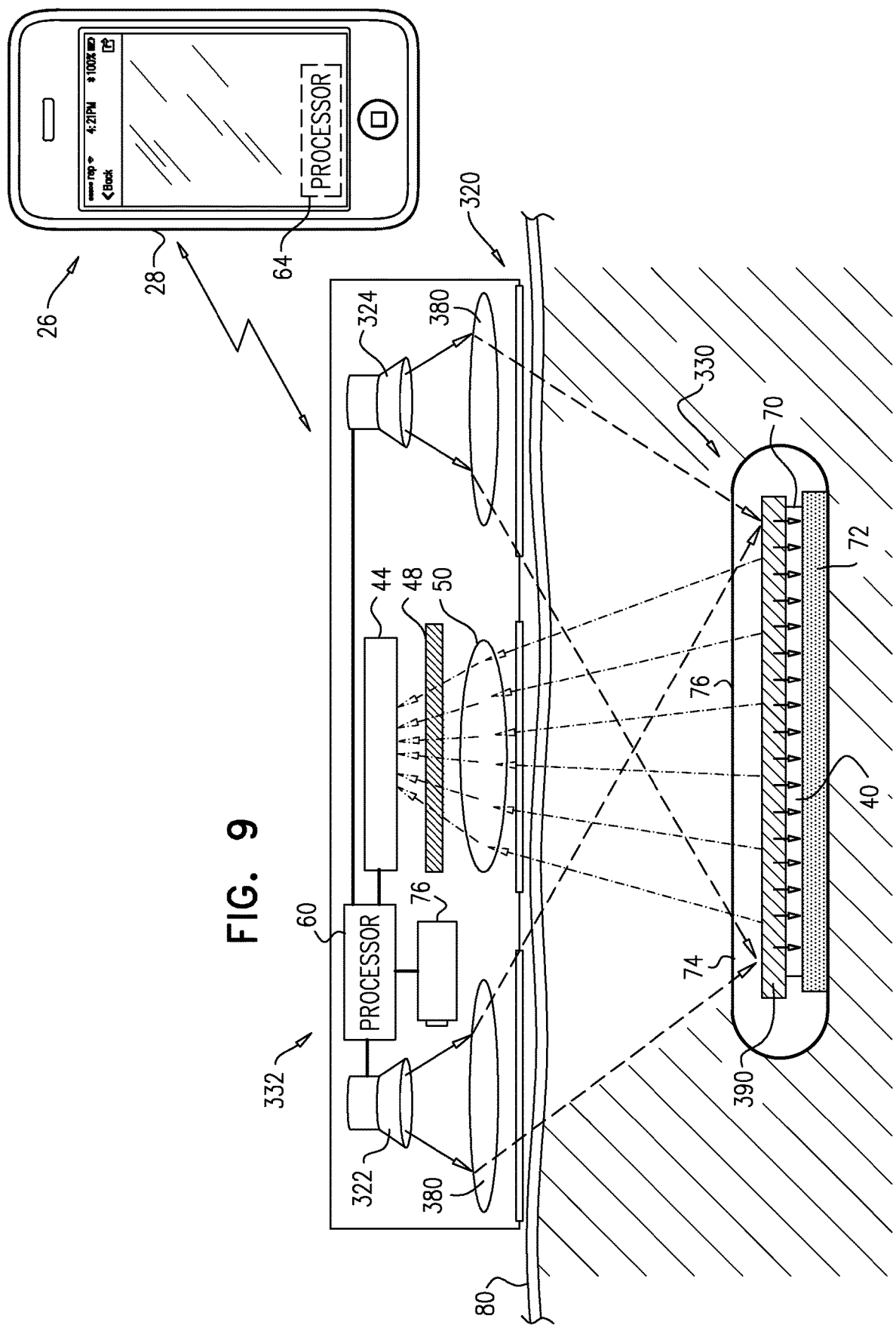
FIG. 9 is a schematic illustration of an alternative configuration of the system of FIG. 6, in accordance with an application of the present invention.

Reference is now made to FIGS. 6 and 9, which are schematic illustrations of a system 320 for transdermal detection of a concentration of an analyte in a subject, in accordance with respective applications of the present invention. Reference is also made to FIG. 7, which is a schematic top-view illustration of an implantable unit 330 of system 320 in the configuration shown in FIG. 6, in accordance with an application of the present invention. System 320 further comprises an external reading unit 332. System 320 may implement any of the techniques described herein regarding systems 20, 120, or 220. Like reference numeral refer to like elements.

As mentioned above, each of fluorescent sensor molecules 40 comprises (i) a binding site for the analyte, and (ii) at least one fluorescent moiety, which is configured to be excited by light at the illumination peak wavelength.

Implantable unit 330 further comprises an upconversion material 390, which is disposed in a vicinity of fluorescent sensor molecules 40. The at least one fluorescent moiety of fluorescent sensor molecules 40 is configured to be excited by light between a first absorption wavelength and a second absorption wavelength greater than the first absorption wavelength. Upconversion material 390 is configured to produce emission of light having an emission peak wavelength between the first absorption wavelength and the second absorption wavelength, upon being excited with light having an excitation peak wavelength that is greater than the second absorption wavelength. The excitation peak wavelength is selected for good penetration through tissue including skin 80, and has better tissue penetration than the emission peak wavelength.

For some applications, upconversion material 390 comprises nanocrystals. Nanocrystals have been extensively explored for upconversion; for example, see Meng Wang, et al., "Upconversion Nanoparticles: Synthesis, Surface Modification, and Biological Applications," Nanomedicine 2011 December 7(6):710-729. Commercially-available nanocrystals for upconversion can also be purchased, for example, from Sigma-Aldrich Corporation (St. Louis, Mo.) under the commercial name Sunstone™, employing a 976 nm excitation wavelength and emission wavelengths ranging between 475 nm and 804 nm. Specifically, 475 nm is a good choice for exciting many green fluorophores that can be used as donors in the biosensor protein.

Typically, in applications in which the fluorescent moiety is a fluorescent protein, the emission light from the upconversion material, in order to be appropriate for excitation of the fluorescent protein, has a peak wavelength within a range of wavelengths determined by the fluorescent protein absorption spectrum. Typically, the absorption spectrum of the fluorescent protein has significant absorption in a wavelength band of about 100-150 nm width, and any light source having significant intensity within this wavelength band is effective in exciting the fluorescent protein.

For some applications, such as shown in FIGS. 6 and 7, upconversion material 390 is distributed in alternating areas of upconversion material and fluorescent sensor molecules 40 within a single layer within the at least one sensor molecule chamber 70, in order to provide close proximity of the upconversion material to the fluorescent sensor molecules. For some applications, upconversion material 390 is disposed in a layer adjacent fluorescent sensor molecules 40, such as above (as shown in FIG. 9) or below (arrangement not shown), in order to provide close proximity of the upconversion material to the fluorescent sensor molecules. For some applications, the upconversion material is mixed with the fluorescent sensor molecules, e.g., by disposing both materials within the same encapsulation material, e.g. hydrogel.

For some applications, the second absorption wavelength is less than 700 nm, and the excitation peak wavelength is greater than 700 nm. For example, the excitation peak wavelength may be greater than 800 nm, such as greater than 950 nm, e.g., greater than 1000 nm. For some applications, the first absorption wavelength is greater than 400 nm, and the excitation peak wavelength is less than 1100 nm. Alternatively or additionally, for some applications, the second absorption wavelength is at least 250 nm less than the excitation peak wavelength. Further alternatively or additionally, for some applications, the second absorption wavelength is less than 550 nm, and the excitation peak wavelength is greater than 700 nm.

In the configurations described with reference to FIGS. 6-9, external reading unit 332 typically comprises at least one external-unit light source 322, which is configured to generate the light having the excitation peak wavelength, which is typically less than 700 nm for these configurations.

For some applications, external-unit light source 322 is a first external-unit light source 322, and the excitation peak wavelength is a first excitation peak wavelength, and external reading unit 332 further comprises a second external-unit light source 324, which is configured to generate light having a second excitation peak wavelength that is (a) greater than 700 nm and (b) different from the first excitation peak wavelength. For some applications, as described hereinabove, the fluorescent moiety of each of fluorescent sensor molecules 40 comprises a donor fluorophore and an acceptor fluorophore. The light generated by first external-unit light source 322 having the first excitation peak wavelength is appropriate, after upconversion by upconversion material 390, for excitation of the donor fluorophore. The light generated by second external-unit light source 324 having the second excitation peak wavelength is appropriate, after upconversion by upconversion material 390, for direct excitation of the acceptor fluorophore.

For some applications, external reading unit 332 comprises optics and/or motion systems that are configured to move the beam of the at least one external-unit light source 322 across a wide field of view, e.g., similar to the area of the external reading unit, until the external reading unit identifies an optimal excitation efficiency (which is typically better than that achieved by uniform illumination of the entire field of view). Alternatively, such as described hereinbelow with reference to FIGS. 10A-E, external reading unit 132 may be configured to indicate to the user a desired movement direction of the external reading unit using user interface 134, such that the user manually aligns the at least one external-unit light source 322 at the optimal location.

For some applications, external reading unit 332 comprises multiple external-unit light sources 322 having the same peak excitation wavelength, and one or more processors enabling the selection of one or more external-unit light source enabling better excitation efficiency as compare to operation of all external-unit light sources.

For some applications, the one or more processors are configured to:
during one or more first time periods: (i) drive first external-unit light source 322 to generate light having the first excitation peak wavelength, and (ii) receive, from light sensor 44, one or more first measurements of the fluorescent light emitted from the acceptor fluorophore, during one or more second time periods non-overlapping with the first time periods: (i) drive second external-unit light source 324 to generate light having the second excitation peak wavelength, and (ii) receive, from light sensor 44, one or more second measurements of the fluorescent light emitted from the acceptor fluorophore, and calculate the concentration of the analyte in the subject based on the first and the second measurements.

For some applications, the acceptor fluorophore is configured to emit fluorescent light having a peak wavelength greater than 625 nm, such as greater than 650 nm.

For some applications, upconversion material 390 comprises (a) a first upconversion material, which is more efficient at upconverting the light at the first excitation peak wavelength than the light at the second excitation peak wavelength, and (b) a second upconversion material, which is more efficient at upconverting the light at the second excitation peak wavelength than the light at the first excitation peak wavelength. For some applications, the first and the second upconversion materials comprise respective nanocrystals of different types, e.g., having different sizes, or comprising different materials and/or coatings. The two different nanocrystal types may be used together in order to optimize the upconversion efficiency at the two specific wavelengths of the light sources of the external reading unit.

Figure 8:
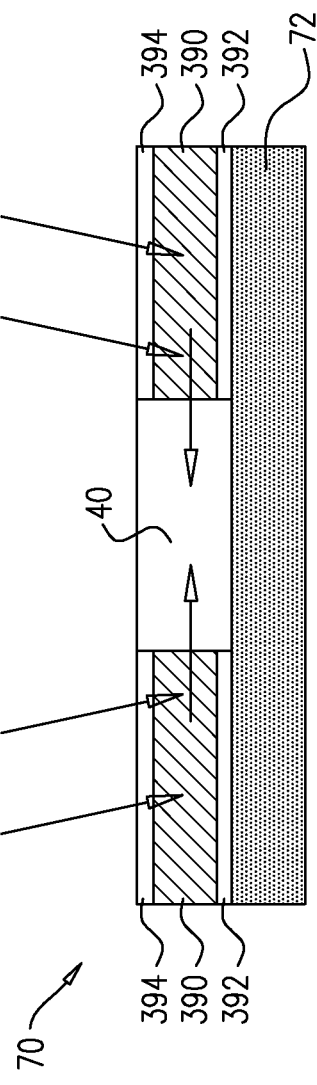
FIG. 8 is a schematic cross-sectional illustration of a portion of the implantable unit of FIG. 7, in accordance with an application of the present invention.

Reference is made to FIG. 8, which is a schematic cross-sectional illustration of a portion of implantable unit 330, in accordance with an application of the present invention. In this configuration, implantable unit 330 further comprises at least one mirror 392 arranged at a bottom surface of upconversion material 390. The at least one mirror 392 reflects the emission light from upconversion material 390 in a generally perpendicular direction toward fluorescent sensor molecules 40. Alternatively or additionally, implantable unit 330 further comprises a dichroic mirror 394 arranged at a top surface of upconversion material 390. Dichroic mirror 394 is configured to be transparent to the light at the excitation peak wavelength (e.g., infrared radiation or specific portions of infrared radiation), while reflecting the light at the emission peak wavelength (e.g., visible light or specific portions of visible light). Dichroic mirror 394 thus allows the light at the excitation peak wavelength (e.g., infrared) to pass into upconversion material 390, while inhibiting the upconverted light at the emission peak wavelength (e.g., visible light) from escaping in the direction of the dichroic mirror (and light source). As a result, the light at the emission peak wavelength is better utilized towards exciting fluorescent sensor molecules 40. For applications in which both mirror 392 and dichroic mirror 394 are provided, the mirrors are generally placed on opposite sides of upconversion material 390, such as shown in FIG. 8.

For some applications, each of the fluorescent sensor molecules comprises exactly one fluorescent moiety. Alternatively, for some applications, each of the fluorescent sensor molecules comprises exactly two fluorescent moieties.

Reference is made to FIG. 1-9, and is additionally made to FIGS. 10A-E, which are schematic illustrations of configurations of light sensor 44, in accordance with respective applications of the present invention. In these applications, light sensor 44 comprises an image sensor 398, i.e., a sensor that senses features of a spatial distribution of photons that impinge on the sensor. Image sensor 398 comprises a plurality of sensor elements 400. For some applications, the one or more processors are configured to use one or more algorithms in order to separate between (a) the fluorescent light emitted from the fluorescent moiety and (b) background (e.g., ambient) light, and to reduce (e.g., remove, typically by subtracting) the contribution of the background light to the detected light signal. Under ordinary illumination conditions, background light may give rise to a background signal that is detected by most or all of sensor elements 400, regardless of whether the sensor elements detect a significant level of emissions from fluorescent sensor molecules 40. The one or more processors are configured to compare the signals generated by the different sensor elements 400 to evaluate the background level that is also sensed by those sensor elements that sense emission from fluorescent sensor molecules 40. The one or more processors are configured to remove this background (generally by subtraction), thereby minimizing the affect of ambient light conditions on the performance of the system.

For some applications, the one or more algorithms utilize prior information regarding the shape (including size), typically in two dimensions (and optionally in one or three dimensions), of one or more regions of implantable unit 130 at which fluorescent sensor molecules 40 are disposed, in order to identify the fluorescent light emitted from the fluorescent moiety. For example, the algorithms may use a Fourier analysis in case of a repetitive structure or any specific (e.g., matched) filter that enhances the signal because of its known spatial distribution. For applications in which implantable unit 130 comprises the at least one sensor molecule chamber 70, which contains fluorescent sensor molecules 40, the one or more algorithms utilize prior information regarding the shape (including size), typically in two dimensions (and optionally in one or three dimensions), of the at least one sensor molecule chamber 70. For applications in which fluorescent sensor molecules 40 are disposed on a surface of enclosure 74 of implantable unit 30, the one or more algorithms utilize prior information regarding the shape (including size), typically in two dimensions (and optionally in one or three dimensions), of the regions at which fluorescent sensor molecules 40 are disposed. For some these applications, image sensor 398 implements techniques described hereinbelow with reference to FIG. 11. In these applications, the external reading unit comprises image sensor 398. It is noted that FIGS. 10A-E, like the other figures, are not drawn to scale.

For some applications, the one or more processors are configured to:
calculate at least one intensity of the light representing emission from fluorescent sensor molecules 40, based on distinguishing between (a) one or more emission areas of the transdermal images corresponding to the locations, in one or two dimensions, of fluorescent sensor molecules 40, and (b) background areas of the transdermal images, e.g., by subtracting the average background intensity from the sensor emission areas, and
calculate the concentration of the analyte in the subject based on the at least one intensity of the light emitted from fluorescent sensor molecules 40.

For some applications, as shown schematically in FIGS. 10A and 10B, image sensor 398 comprises an equally-spaced two-dimensional array 402 of equally-sized sensor elements 400 arranged in a rectangular grid having at least two sensor elements in each direction, e.g., a CCD or CMOS image sensor. The image sensor is configured to generate one or more two-dimensional pixelated transdermal images of light passing from the body through tissue including skin 80. For some applications, as shown schematically in FIG. 10A (in which the actual size of the array is substantially larger than schematically shown, for example 1024×1024 sensor elements), the image sensor is configured to generate high-resolution images (for example, including at least 1024×1024 pixels), as is known in the art, using, for example, a CCD or CMOS image sensor.

For other applications, image sensor 398 comprises a smaller number of sensor elements 400, which are not necessarily arranged as a grid, such that image sensor 398 is configured to generate low-resolution images. For example, image sensor 398 may comprise no more than 1,024 sensor elements 400, such as no more than 64 sensor elements, no more than 32 sensor elements, no more than 25 sensor elements, no more than nine sensors elements, or no more than four sensor elements. Typically, image sensor 398 comprises at least three sensor elements 400, such as at least four or five sensor elements 400, e.g., at least eight sensor elements 400. For some applications, each of sensor elements 400 has a surface area of at least 1 mm2, such as at least 4 mm2, and/or no more than 100 mm2, such as no more than 50 mm2.

In these applications, sensor elements 400 typically comprise respective sampling circuitries 404. Typically, each of sampling circuitries 404 is configured to output a digital or analogue value indicative of an intensity of light sensed by the corresponding sensor element 400. Typically, the external reading unit comprises control electronics 458, which are configured to simultaneously read sampling circuitries 404 (typically independently, and typically in parallel). (For clarity of illustration, control electronics 458 is shown only in FIG. 10C, and is shown connected to only a subset of the circuitries; in practice, control electronics 458 is connected to all of the circuitries, and typically is additionally provided in the configurations shown in FIGS. 10B, 10D, and 10E.) (In contrast, each image sensor in a CCD or CMOS image sensor does not have its own dedicated sampling circuitry.) For some applications, control electronics 458 are configured to sample all of sampling circuitries 404 in no more than 3 msec, such as no more than 2 msec, e.g., no more than 1 msec. For some applications, these quick sampling periods approximately match the duration of illumination of fluorescent sensor molecules 40. For some applications, sampling circuitries 404 samples each of the sensor elements during the illumination of fluorescent sensor molecules 40 and before and/or after the illumination.

These techniques may thus provide a faster response time than a conventional pixelated image sensor (e.g., a CCD or CMOS image sensor), which allows synchronization of sensing with the illumination pulse, and thus may allow the one or more processors to reject background that is not synchronized with the illumination pulse. These techniques may also provide increased design flexibility. Thus the system may enjoy the benefit of removing background both in time and in space while keeping the high collection efficiency of the sensor.

For some of these applications, such as shown in FIG. 10B, image sensor 398 comprises equally-spaced two-dimensional array 402 of equally-sized sensor elements arranged in a rectangular grid having at least two sensor elements in each direction, and the transdermal images comprise two-dimensional pixelated images. Typically, in these applications, image sensor 398 comprises no more than 32 sensor elements in each direction, e.g., no more than 16 sensor elements in each direction, such as no more than 5 sensor elements in each direction, e.g., 2×2, 3×3, 4×4, or 5×5 sensor elements. For example, image sensor 398 may comprise an array of 12-30 sensor elements.

For some applications, such as shown by way of example in FIGS. 10C, 10D, and 10E, sensor elements 400 are (a) arranged to sense light from different respective portions of a total field of view of image sensor 398, and (b) not arranged as sensor elements of a rectangular grid of sensor elements. For example, the field of view of the image sensor may be about 20×20 mm.

For some applications, such as shown in FIGS. 10C, 10D, and 10E, at least two of sensor elements 400 have different respective surface shapes and/or different respective surface areas.

For some applications, sensor elements 400 comprise:
one or more central sensor elements 400A, which are disposed in a central area 406 of image sensor 398. Central sensor elements 400A are configured to obtain the signal under the best orientation conditions; and
two or more (e.g., four or more) peripheral sensor elements 400B, which are disposed generally surrounding central sensor elements 400A (in a peripheral area 408 of image sensor 398). Peripheral sensor elements 400B are configured to enable removal of background light and/or alignment of the external reading unit.

For some applications, at least one of the one or more central sensor elements 400A has a first surface shape, and at least one of the two or more peripheral sensor elements 400B has a second surface shape that is different from the first surface shape. For some applications, the one or more central sensor elements 400A comprise exactly one central sensor element 400A. For some of these applications, as shown in FIG. 10C, central sensor element 400A is polygonal and has more than four sides, e.g., is hexagonal or octagonal. For others of these applications, such as shown in FIGS. 10D and 10E, central sensor element 400A is elliptical, e.g., circular.

For some applications, such as shown in FIG. 10E, peripheral sensor elements 400B are arranged in two or more rings around the one or more central sensor elements 400A at respective average distances from the one or more central sensor elements 400A.

For some applications:
the one or more central sensor elements 400A have a central sensor total surface area in aggregate,
the two or more peripheral sensor elements 400B have a peripheral sensor average surface area,
all of the sensor elements 400 (both the one or more central sensor elements 400A and the two or more peripheral sensor elements 400B) have a total sensors surface are in aggregate.

For some applications, the peripheral sensor average surface area is less than the central sensor total surface area. For some applications, the central sensor total surface area is at least 50% of the total sensors surface area, and/or no more than 35%, e.g., no more than 25%, of the total sensors surface area. The use of one or more relatively large central sensor elements 400A generally improves the signal-to-noise ratio, because the signal typically scales with sensor element area, while noise typically scales at a lower power, e.g., the square root of the area. It is therefore advantageous for best signal to noise (SNR) to use only the signal coming from pixels (elements in an array) that detect significant levels of signal and avoid using other elements that are providing mainly background signal. It is therefore of advantage to use a specially designed sensor array that can combine the benefits of both an array and a single sensor element.

For some applications, the one or more processors are configured to use the one or more central sensor elements 400A to predominantly sense the light emitted by fluorescent sensor molecules 40, and the two or more peripheral sensor elements 400B to predominantly sense background light not emitted by fluorescent sensor molecules 40. For some applications, the one or more processors are configured to ascertain the one or more emission areas of the transdermal images corresponding to the locations, in one or two dimensions, of the fluorescent sensor molecules by ascertaining that the one or more central sensor elements 400A sense predominantly fluorescent light emitted by fluorescent sensor molecules 40 (for example, at last 50% of the light sensed by the one or more central sensor elements 400A is emitted from fluorescent sensor molecules 40), and, optionally, to further ascertain that the one or more peripheral sensor elements 400B sense predominantly background (e.g., ambient) light not emitted by fluorescent sensor molecules 40 (for example, at last 50% of the light sensed by the one or more peripheral sensor elements 400B is not be emitted from fluorescent sensor molecules 40).

For some applications, sensor elements 400 may be arranged in a vector along a single spatial axis (configuration not shown).

For some applications, the one or more processors evaluate the background (e.g., ambient) light level using image sensor 398 by:
classifying sensor elements 400 such that some of the sensor elements 400 are classified as sensing predominantly background (e.g., ambient) (e.g., at least 50%) light ("background sensor elements"; these typically correspond to the one or more peripheral sensor elements 400B) and some other sensor elements 400 are classified as sensing predominantly (e.g., at least 50%) light generated by fluorescent sensor molecules 40 ("signal sensor elements"; these typically correspond to the one or more central sensor elements 400A), and
based on the values and spatial distribution of the background sensor elements, evaluate a background light level at the position of the signal sensor elements, e.g., by an average over the background sensor elements, or by fitting the background sensor elements by a continuous function and evaluating the value of the function at a central location representing the signal sensor elements.

For some applications, external reading unit 132 further comprises a user interface 134, which typically comprises a graphical display, other visual outputs, and/or an audio generator. User interface 134 may be incorporated into housing 62 of external reading unit 132, or may be in a separate component in data communication (wireless or wired) with housing 62 of external reading unit 132. The one or more processors are configured to (a) ascertain, responsively to one or more respective locations of the one or more emission areas of the transdermal images, a desired movement of external reading unit 132 (e.g., of optical unit 46) with respect to an external surface of skin 80, and (b) output, via user interface 134, an indication of the desired movement. A user moves external reading unit 132 in order to better align the external reading unit with the implantable unit. These techniques are optionally used in combination with the background removal techniques described above; the one or more processors use the background light sensed by the sensor elements not positioned over fluorescent sensor molecules 40 after centering, for correction of the light sensed from the fluorescent sensor molecules 40, as described above.

For some applications, the indication of the desired movement includes a direction of the desired movement with respect to the external surface of the skin. For some applications, user interface 134 is configured to guide the user to position the external reading unit at the most appropriate location, e.g., using crosshairs, arrows, or other visual or audio indicators (e.g., including pitch and/or volume) of the desired location and/or desired motion toward the desired location. For example, the most appropriate location may be with a center of the field of view of image sensor 398 (e.g., the one or more central sensor elements 400A) placed over fluorescent sensor molecules 40. For some applications, the one or more processors are configured to: (a) ascertain, responsively to one or more respective locations of the one or more emission areas of the transdermal images, a desired change in disposition of the external reading unit with respect to an external surface of the skin, and (b) output, via user interface 134, an indication of the desired change in disposition. For example, the change in disposition may be a change in position of external reading unit 132 with respect to the external surface of the skin, and/or a change in orientation (e.g., rotational orientation) of the external reading unit with respect to the external surface of the skin. Typically, the system generates an output instructing the user to reposition the external reading unit only if the system detects a positioning error beyond a certain limit.

For some applications, the one or more processors are configured to output the indication upon ascertaining, by the one or more processors, that at least a portion of fluorescent sensor molecules 40 does not appear in the transdermal images. For some applications, the one or more processors are configured to output an indication, via user interface 134, if the light signal cannot be measured, e.g., after a certain amount of time or number of attempts, and/or when the implantable unit is located to be beyond a certain distance from the center of the field of view of the image sensor.

As mentioned above, for some applications image sensor 398 comprises at least three sensor elements, which comprise one or more central sensor elements 400A, which are disposed in central area 406 of image sensor 398, and two or more peripheral sensor elements 400B, which are disposed generally surrounding the one or more central sensor elements 400A. For some of these applications, the one or more processors are configured to ascertain the desired movement of external reading unit 132 by ascertaining that a first intensity of light sensed by one or more first ones of the peripheral sensor elements 400B is greater than a second intensity of light sensed by one or more second ones of the peripheral sensor elements 400B. For some of these applications, the one or more processors are configured to ascertain that the desired movement is in a direction from the one or more central sensor elements 400A toward the one or more first ones of the peripheral sensor elements 400B. This is repeated until the intensity of light sensed by all of the peripheral sensor elements 400B is approximately equal, indicating that the one or more central sensor elements 400A are approximately centered over fluorescent sensor molecules 40.

For some of these applications, the one or more central sensor elements 400A have the central sensor total surface area in aggregate, and the two or more peripheral sensor elements 400B have the peripheral average surface area, which is less than the central sensor total surface area. For some of these applications, the one or more central sensor elements 400A comprise exactly one central sensor element 400A. For some of these applications, at least one of one or more central sensor elements 400A has a first surface shape, and at least one of the two or more peripheral sensor elements 400B has a second surface shape that is different from the first surface shape.

These techniques are optionally used in combination with the background removal techniques described above; the background light sensed by the two or more peripheral sensor elements 400B not after centering is used for correction of the light sensed by the one or more central sensor elements 400A from the fluorescent sensor molecules 40, as described above.

For some applications, the one or more processors are configured to calculate a background intensity of the light at the at least one peak wavelength at the background areas of the transdermal images, and to correct the calculated at least one intensity of light representing the net emission from the fluorescent sensor molecules using the background intensity. For some applications, the one or more processors are configured to correct the calculated at least one intensity of the light representing the emission from fluorescent sensor molecules 40 by subtracting the background intensity from an intensity of the light in the one or more emission areas of the transdermal images.

For some applications, the one or more processors are configured to use a one- or two-dimensional representation of a spatial distribution of fluorescent sensor molecules 40 in implantable unit 130 as a factor in the analysis of the transdermal images for ascertaining the one or more areas of the transdermal images corresponding to the locations, in one or two dimensions, of fluorescent sensor molecules 40. For example, the one- or two-dimensional representation may be loaded in a memory of external system 26 (e.g., the external reading unit) before the external reading unit is provided to the user. The one or more processors are configured to analyze the one- or two-dimensional images of the sensed light with reference to the one- or two-dimensional representation in order to find a best fit between the images and the representation, and then to assume that light outside of this best fit is background noise rather than emissions from fluorescent sensor molecules 40.

For some applications, the fluorescent sensor molecules are distributed within the implantable unit in a repetitive pattern, and/or in a non-uniform spatial distribution. For some applications, fluorescent sensor molecules 40 are distributed within the implantable unit such that in one or more (e.g., a plurality of) distinct areas, a different signal intensity is detected as compared to other areas in which the fluorescent sensor molecules are distributed. For example, sensor molecule chamber 70 containing the fluorescent sensor molecules may have a lesser thickness in distinct areas 136 than in the other areas, or a greater thickness in distinct areas 138 than in other areas.

As mentioned above, for some applications, implantable unit 130 further comprises the at least one sensor molecule chamber 70, in which fluorescent sensor molecules 40 are disposed. For some of these applications, the at least one sensor molecule chamber 70 comprises (a) a substrate, which defines one or more surfaces, and (b) a membrane. Fluorescent sensor molecules 40 are disposed in the at least one sensor molecule chamber 70 between the membrane and the one or more surfaces of the substrate. The one or more surfaces have an average reflectivity, and one or more sub-areas of the one or more surfaces have a sub-area reflectivity that is greater than the average reflectivity. The one or more processors are configured to use one or more respective locations of one or more areas of the transdermal images corresponding to locations, in one or two dimensions, of the sub-areas in as a factor in the analysis of the transdermal images for ascertaining the locations of the one or more areas of transdermal images corresponding to the locations, in one or two dimensions, of the fluorescent sensor molecules. For some applications, the sub-area reflectivity is at least twice the average reflectivity. Alternatively or additionally, for some applications, the sub-areas are distributed within the at least one sensor molecule chamber 70 in a repetitive pattern.

For some applications, the one or more processors are configured to use the known spatial distribution, in one or two dimensions, of the fluorescent sensor molecules in the implantable unit as a factor in the analysis of the transdermal images for ascertaining the one or more areas of location of the implantable unit in the transdermal images corresponding to the locations, in one or two dimensions, of the fluorescent sensor molecules.

For some applications, the one or more processors are configured to, during one or more third time periods non-overlapping with the first time periods described hereinbelow with reference to FIGS. 1-12: (a) drive the one or more light sources to generate the light having the second illumination peak wavelength, and (b) calculate the concentration of fluorescent sensor molecules 40, by analyzing a spatial distribution of the fluorescent light in the transdermal images. For some applications, the one or more processors are configured to, during the one or more third time periods, analyze the distribution of the fluorescent light in the transdermal images by calculating an extent of absorption of the fluorescent light emitted from the acceptor fluorophore as a function of distance from the one or more second light sources.

For some applications, the one or more processors may be configured to use measurements at different times in order to remove background emissions. For example, the one or more processors may be configured to evaluate the background signal using one or more measurements taken before and/or after the light source(s) generate light, and subtract such background signal from the measured light, e.g., to measure the signal at several times during generation of light by the light source(s) and to fit the measured values to the known function of the generated light. This technique may be practiced in combination with the background removal techniques described above.

Reference is now made to FIG. 11, which is a schematic illustration of a system 420 for transdermal detection of a concentration of an analyte in a subject, in accordance with an application of the present invention. System 420 comprises an implantable unit 30 and an external reading unit 432, which is physically separate and distinct from implantable unit 30. Implantable unit 30 may implement any of the techniques described hereinabove regarding implantable units 30, 130, 230, and/or 330. Other than as described below, external reading unit 432 may implement any of the techniques described herein regarding external reading units 32, 132, 232, 332, and/or 532, described hereinabove with reference to FIGS. 1-9 and/or FIGS. 10A-E.

External reading unit 432 comprises light sensor 44, which, in this configuration, comprises image sensor 398, which may implement any of the configurations described hereinabove with reference to FIGS. 10A-E. External reading unit 432 further comprises at least one fast response sensor element 454, e.g., a photodiode. A beam splitter 452 may be provided to share the optical detection path with the image sensor and the at least one fast response sensor element. One or more light sources may be provided in external reading unit 432 (such as shown in FIGS. 1, 6, and/or 9), and/or in implantable unit 30 (such as shown in FIGS. 1, 2, and/or 4). If the light source(s) are provided in the external reading unit, the light source(s) may share part of the optical path with the collection channel, such as using a beam splitter. Alternatively, for some applications, the image sensor and the fast response sensor element are aimed at non-identical portions of the total field of view, without using a beam-splitter. The non-identical portions may either partially overlap one another, or may be entirely non-overlapping with one another.

For some applications, the one or more processors are configured to use image sensor 398 to identify the location of fluorescent sensor molecules 40 (and thus implantable unit 30) and guide the user to improve the position of external reading unit 432 with respect to the implantable unit, such as to position the implantable unit in the center of the field of view of the image sensor. For example, such guidance may be provided using the techniques described hereinabove with reference to FIGS. 1-9 and 10A-E. Alternatively or additionally, for some applications, the one or more processors are configured to use image sensor 398 to evaluate the background signal generated by ambient light, such as using the techniques described hereinabove with reference to FIGS. 1-9 and 10A-E.

External reading unit 432 comprises a high-frequency electronic circuit 456, which samples fast response sensor element 454, thereby enabling the integration of only the signal that is synchronized with the illumination pulses generated by the light sources, rejecting all ambient light that is collected at different times. External reading unit 432 may also comprise control electronics 458, for processing the signal(s) generated by image sensor 398.

For some applications, using both types of sensors (image sensor 398 and fast response sensor element 454) combines the benefits of both types of sensors and provides enhanced measurement accuracy. For example, the one or more processors may be configured to:

drive the one or more light sources to provide pulse illumination to fluorescent sensor molecules 40 in implantable unit 30;

synchronize the measurements of both image sensor 398 and the at least one fast response sensor element 454 such that the pulse of the light source is included in the integration time of both measurement channels;

evaluate the background (e.g., ambient) light level using image sensor 398 by: (a) classifying all sensor elements 400 of the image such that some of the sensor elements 400 are classified as containing predominantly background light (e.g., at least 50%, such as at least 80%) ("background sensor elements") and some other sensor elements are classified as containing predominantly signal/fluorescent light (e.g., at least 50%, such as at least 80%) generated by fluorescent sensor molecules 40 ("signal sensor elements"), and (2) based on the values and spatial distribution of the background sensor elements, evaluate a background light level at the position of the signal sensor elements, e.g., by an average over the background sensor elements, or by fitting the background sensor elements by a continuous function and evaluating the value of the function at a central location representing the signal sensor elements; and/or adjust the background light level for the differences in integration times and sensitivity between the two sets of sensors, and remove the adjusted background light level from the signal generated by the at least one fast response sensor element, as taken at the time of the illumination pulse generated by light source(s).

These techniques generally provide good accuracy of the measured signal, because both spatial filtering enabled by image sensor 398 and the temporal filtering enabled by the at least one fast response sensor element 454 provide improved removal of background noise.

Reference is now made to FIG. 12, which is a schematic illustration of a system 520 for transdermal detection of a concentration of an analyte in a subject, in accordance with an application of the present invention. The features of this configuration may be implemented in combination with any of the techniques described herein; like reference numeral refer to like elements. For example, system 520 may implement the techniques for individually driving the implantable-unit light sources from the external unit described hereinabove with reference to FIG. 4. System 520 comprises an implantable unit 530, and an external reading unit 532.

Implantable unit 530 comprises three light sources: (a) first implantable-unit light source 42, which is configured to emit light appropriate for excitation of the donor fluorophore, (b) second implantable-unit light source 126, which is configured to emit light appropriate for direct excitation of the acceptor fluorophore, (c) a third implantable-unit light source 528 configured to emit light having a peak wavelength appropriate for effective penetration through the tissue (which typically includes skin 80), e.g., greater than 650 nm. The strength of the signal emitted by third implantable-unit light source 528 does not vary based on the level of sensor protein or analyte, and thus may be useful for several functions, such as described below.

Typically, third implantable-unit light source 528 is configured to illuminate in the general direction of the external reading unit. Alternatively or additionally, at least one reflective surface located within the implantable unit may reflect the light from third implantable-unit light source 528 in the general direction of the external reading unit. Alternatively, third implantable-unit light source 528 is directed in any general direction, e.g., in the direction of sensor molecule chamber 70, and light arrives to light sensor 44 of external reading unit 432 via scattering.

For some applications, external reading unit 532 is configured to activate third implantable-unit light source 528 to operate at third time periods not overlapping the first and second time periods during which the first and the second light sources operate.

For some applications, external reading unit 532 is configured to operate third implantable-unit light source 528 in order to enable easier alignment of the external reading unit location with respect to the implantable unit, as discussed above regarding embodiments in which the user receives an indication of desired movement of the external reading unit. The light generated by third implantable-unit light source 528 may also be useful for locating the implantable unit for extraction of the unit from the subject's body. Alternatively or additionally, the light generated by third implantable-unit light source 528 may provide an indication that the circuitry of the implantable unit is functioning properly even when no light can be detected from the acceptor fluorophore. By calculating the ratio between the intensity of the emission when exciting using second implantable-unit light source 126 (which directly excites the acceptor fluorophore) and the intensity measured with third implantable-unit light source 526, the one or more processors may obtain additional information, e.g., regarding the amount of active biosensor protein in the implantable unit. By tracking this ratio over a long time, e.g., by comparing the current value to the value immediately following implantation, the one or more processors may alert the user of the need to replace the implantable unit within some time, based on a decline in this ratio. Because the emission when exciting the acceptor fluorophore directly is not dependent on glucose concentration, such a measurement and alert cannot be confounded by current glucose values.

Alternatively or additionally, for some applications, external reading unit 532 is configured to evaluate the transmission through the tissue of the light generated by third implantable-unit light source 528, and to utilize this information for the calibration of the measurement of the analyte concentration and/or for the alignment process.

Alternatively or additionally, for some applications, external reading unit 532 is configured to operate third implantable-unit light source 528 as a reference in order to evaluate the amount of fluorescent sensor molecules, e.g., fluorescent protein, in the implantable unit and utilize this information as an indication of the sensor unit status, or as an input factor in order to adjust the duration and/or the intensity of the illumination of the first and/or second light sources.

Alternatively or additionally, the implantable unit is configured to use third implantable-unit light source 528 to transmit a signal indicative of a measured temperature at the position of the implantable unit, such as described hereinbelow with reference to FIGS. 1-12.

Reference is made to FIGS. 1-12. In some applications of the present invention, the one or more processors are configured to change a ratio of the duration or the total energy of the light pulse at the first illumination peak wavelength to the duration or the total energy of the light pulse at the second illumination peak wavelength. Such a change in ratio (which may include repeated changes over time) may be desirable to achieve acceptable signal levels and/or correct for changes (typically decreases) in the concentration of fluorescent sensor molecules 40 in the implantable device over time, typically in configurations in which each of fluorescent sensor molecules 40 comprises (i) a binding site for the analyte, (ii) a donor fluorophore, and (iii) an acceptor fluorophore, such as described hereinabove. For some applications, the one or more processors are configured to:

drive one or more light sources (external-unit light sources, internal-unit light sources, or a combination of external-unit and internal-unit light sources) to (a) during a plurality of first time periods, generate light having the first illumination peak wavelength appropriate for excitation of the donor fluorophore, and (b) during a plurality of second time periods non-overlapping with the first time periods, generate light having the second illumination peak wavelength appropriate for direct excitation of the acceptor fluorophore; techniques may be used that are described hereinabove with reference to FIGS. 1 and 2 for calculating the concentration of the analyte;

receive, from light sensor 44, respective measurements of the fluorescent light emitted from the acceptor fluorophore during (a) the first time periods and (b) the second time periods; techniques may be used that are described hereinabove with reference to FIGS. 1 and 2 for calculating the concentration of the analyte;

calculate the concentration of the analyte in the subject based on the respective measurements; techniques may be used that are described hereinabove with reference to FIGS. 1 and 2 for calculating the concentration of the analyte;

during a first operational period that includes one or more of the first time periods and one or more of the second time periods, set a ratio of an aggregate duration of the first time periods to an aggregate duration of the second time periods to have a first value; and during a second operational period that is after the first operational period and that includes one or more of the first time periods and one or more of the second time periods, set the ratio to have a second value that is different from the first value, such as greater than the first value of the ratio.

For some applications, the first operation period has a duration of at least one week.

For some applications, the one or more processors are configured to set the ratio to have the second value based on a decrease in signal strength of fluorescent sensor molecules 40. For some applications, the one or more processors are configured to set the ratio to have the second value based on a decrease in a concentration of fluorescent sensor molecules 40. For some applications, the one or more processors are configured to ascertain the decrease in the concentration of fluorescent sensor molecules 40.

For some applications, light sensor 44 comprises an image sensor, which is configured to generate one or more transdermal images of the fluorescent light emitted from the acceptor fluorophore. The one or more processors are configured to, during one or more third time periods non-overlapping with the first time periods: (a) drive the one or more light sources to generate the light at the second illumination peak wavelength, and (b) calculate the concentration of fluorescent sensor molecules 40, by analyzing a spatial distribution of the fluorescent light in the transdermal images. For some applications, the one or more processors are configured to, during the one or more third time periods, analyze the distribution of the fluorescent light in the transdermal images by calculating an extent of absorption of the fluorescent light emitted from the acceptor fluorophore as a function of distance from the one or more second light sources.

For some applications, the one or more light sources comprise one or more first light sources and one or more second light sources. The one or more processors are configured to drive the one or more first light sources to generate the light at the first illumination peak wavelength, and the one or more second light sources to generate the light at the second illumination peak wavelength. For some applications, the implantable unit comprises the one or more first light sources and the one or more second light sources, such as described hereinabove with reference to FIG. 4. For other applications, the implantable unit comprises the one or more first light sources, and the external reading unit comprises the one or more second light sources.

Reference is again made to FIGS. 1-12. In some applications of the present invention, typically in configurations in which each of fluorescent sensor molecules 40 comprises (i) a binding site for the analyte, (ii) a donor fluorophore, and (iii) an acceptor fluorophore, such as described hereinabove, the one or more processors are configured to:

drive the one or more light sources to, during a plurality of first time periods alternating with a plurality of second time periods non-overlapping with the first time periods:
(a) during the first time periods, (i) generate light having a first illumination peak wavelength appropriate for excitation of the donor fluorophore, and (ii) receive, from the light sensor, measurements of first intensities of the fluorescent light emitted from the acceptor fluorophore, and
(b) during the second time periods, (i) generate light having a second illumination peak wavelength appropriate for direct excitation of the acceptor fluorophore, and (ii) receive, from the light sensor, measurements of second intensities of the fluorescent light emitted from the acceptor fluorophore, for each of a plurality of the first and the second time periods, respectively, set a first energy of the light (i.e., the integral overtime of the intensity of the light) generated having the first illumination peak wavelength, and a second energy of the light generated having the second illumination peak wavelength, so as to regulate, toward a target value, a relationship of values of the first and the second intensities of the sensed fluorescent light; for example, the one or more processors may regulate a ratio of the values, or may regulate a difference between the values (e.g., reduce a difference between the values, and/or minimize a difference between the values), and calculate the concentration of the analyte in the subject based in part on the first energy of the generated light having the first illumination peak wavelength and the second energy of the generated light having the second illumination peak wavelength, for example, based in part on a ratio of (a) the first energy of the generated light having the first illumination peak wavelength and (b) the second energy of the generated light having the second illumination peak wavelength.

This technique may correct for changes (typically decreases) in the concentration of fluorescent sensor molecules 40 in the implantable device over time. For example, a lower concentration of fluorescent sensor molecules 40 under given illumination conditions may result in a lower signal. The system thus increases the illumination energy (e.g., by increasing the intensity and/or pulse length), resulting in a higher signal. This is repeated until the signal is within a predefined band of values. This technique may thus help maximize the measurement signal-to-noise ratio to enable accurate measurement, such as by using relatively higher excitation energies when the response from the implantable unit is low, e.g., because of a low concentration of fluorescent sensor molecules or a low concentration of the analyte, e.g., glucose. This technique thus provides automatic compensation for low fluorescent sensor molecules 40 concentration, which enables measurement while the concentration is too low for accurate measurement under standard conditions. To the extent that changing the excitation energy from pulse to pulse creates changes in background, the techniques described hereinabove with reference to FIGS. 1-9 and 10A-E may optionally be used to remove the background.

For some applications, the one or more light sources comprise one or more first light sources and one or more second light sources, and the one or more processors are configured to drive the one or more first light sources to generate the light at the first illumination peak wavelength, and the one or more second light sources to generate the light at the second illumination peak wavelength. For some applications, the implantable unit comprises the one or more first light sources and the one or more second light sources, such as described hereinabove with reference to FIG. 4. For other applications, the implantable unit comprises the one or more first light sources, and the external reading unit comprises the one or more second light sources.

Reference is again made to FIGS. 1-12. In some applications of the present invention, the implantable unit is configured to measure the temperature at the position of the implantable unit, and to transmit the measured temperature to the external reading unit, such as for generation of calibration information, as described hereinabove with reference to FIG. 1. For example, the implantable unit may comprise at least one temperature-sensitive electronic element such that the time delay between the triggering of the illumination by the external reading unit and the actual timing of the illumination pulse depends on implantable unit temperature. The triggering of the illumination in this context may be, for example, the beginning of the charging pulse supplied to the implantable unit, and the timing of the illumination pulse may be measured, for example, from the timing of the peak intensity of the detected light in the sensor. Alternatively, for applications in which the implant circuitry is configured to generate a train of light pulses (such as using third implantable-unit light source 528, described hereinabove with reference to FIG. 12), the implantable unit may be configured such that the at least one temperature-sensitive element in the circuitry causes a change in the time between successive light pulses as a function of temperature; such a change can be readily identified by the external reading unit by analyzing the received optical signal. The temperature-sensitive element may comprise, for example, a thermistor or a temperature sensitive capacitor.

These techniques may be used in combination with any of the configurations of the system described herein.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Pat. No. 7,951,357 to Gross et al.;
US Patent Application Publication 2010/0160749 to Gross et al.;
US Patent Application Publication 2010/0202966 to Gross et al.;
US Patent Application Publication 2011/0251471 to Gross et al.;
US Patent Application Publication 2012/0059232 to Gross et al.;
US Patent Application Publication 2013/0006069 to Gil et al.;
PCT Publication WO 2006/006166 to Gross et al.;
PCT Publication WO 2007/110867 to Gross et al.;
PCT Publication WO 2010/073249 to Gross et al.;
PCT Publication WO 2013/001532 to Gil et al.;
PCT Publication WO 2014/102743 to Brill et al.;
U.S. Provisional Patent Application 60/588,211, filed Jul. 14, 2004;
U.S. Provisional Patent Application 60/658,716, filed Mar. 3, 2005;
U.S. Provisional Patent Application 60/786,532, filed Mar. 27, 2006;
U.S. Provisional Patent Application 61/746,691, filed Dec. 28, 2012; and
U.S. Provisional Patent Application 61/944,936, filed Feb. 26, 2014.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for detecting a concentration of an analyte in a subject, the apparatus comprising:
 an implantable unit, which is configured to be implanted in a body of the subject, and comprises:
 (a) fluorescent sensor molecules, each of which comprises (i) a binding site for the analyte, (ii) a donor fluorophore, and (iii) an acceptor fluorophore;
 (b) a first implantable-unit light source that is configured to generate light having a first illumination peak wavelength appropriate for excitation of the donor fluorophore;
 (c) a second implantable-unit light source that is configured to generate light having a second illumination peak wavelength appropriate for direct excitation of the acceptor fluorophore; and
 (d) a third implantable-unit light source configured to emit light having a peak wavelength appropriate for effective penetration through tissue; and
 an external system, which is physically separate and distinct from the implantable unit, and which comprises:
 (a) an external reading unit, which comprises a light sensor, which is configured to sense fluorescent light emitted from the acceptor fluorophore; and
 (b) one or more processors, which are configured to:
  (i) during one or more first time periods: (a) drive the first implantable-unit light source to generate the light having the first illumination peak wavelength, and (b) receive, from the light sensor, one or more first measurements of the fluorescent light emitted from the acceptor fluorophore, and
  (ii) during one or more second time periods non-overlapping with the first time periods: (a) drive the second implantable-unit light source to generate the light having the second illumination peak wavelength, and (b) receive, from the light sensor, one or more second measurements of the fluorescent light emitted from the acceptor fluorophore,
 wherein the apparatus is configured to measure a temperature at the implantable unit,
 wherein the implantable unit is configured to use the third implantable-unit light source to transmit an optical signal indicative of the measured temperature, wherein the strength of the optical signal emitted by the third implantable-unit light source does not vary based on a level of the fluorescent sensor molecules or a concentration of the analyte, and
 wherein the one or more processors of the external system are configured to generate calibration information using the measured temperature, and calculate the concentration of the analyte in the subject based on the first and the second measurements and using the calibration information.

2. The apparatus according to claim 1, wherein the external reading unit is configured to drive the first implantable-unit light source and the second implantable-unit light source to generate the light having the first and the second illumination peak wavelengths, respectively, by transmitting electromagnetic radiation at first and second different frequencies, respectively.

3. The apparatus according to claim 1, wherein the implantable unit further comprises at least one sensor molecule chamber, in which the fluorescent sensor molecules are disposed.

4. The apparatus according to claim 1, wherein the fluorescent sensor molecules are fluorescent sensor proteins.

5. The apparatus according to claim 1, wherein the first illumination peak wavelength is greater than 300 nm and less than 550 nm.

6. The apparatus according to claim 5, wherein the first illumination peak wavelength is less than 525 nm.

7. The apparatus according to claim 6, wherein the first illumination peak wavelength is less than 500 nm.

8. The apparatus according to claim 1, wherein the second illumination peak wavelength is greater than 300 nm and less than 650 nm.

9. The apparatus according to claim 1, wherein the first illumination peak wavelength is greater than 300 nm and less than 550 nm, and the second illumination peak wavelength is greater than 300 nm and less than 650 nm.

10. The apparatus according to claim 1, wherein the acceptor fluorophore is configured to emit the fluorescent light having an emission peak wavelength that is between 100 and 500 nm greater than the first illumination peak wavelength.

11. The apparatus according to claim 1, wherein the analyte is glucose, and wherein the binding site is for the glucose.

12. The apparatus according to claim 1, wherein the implantable unit has a volume of no more than 250 mm$^3$.

13. The apparatus according to claim 1, further comprising packaging, in which the implantable unit is stored before implantation, wherein an external surface of the implantable unit is sterile while stored in the packaging.

14. The apparatus according to claim 1,
wherein the implantable unit further comprises implant circuitry, which (a) is configured to generate a train of light pulses using the third implantable-unit light source, and (b) comprises at least one temperature-sensitive element,
wherein the implantable unit is configured such that the at least one temperature-sensitive element causes a change in time between successive light pulses as a function of temperature, and
wherein the external system is configured to identify the change in time by analyzing the received optical signal.

15. The apparatus according to claim 1,
wherein the implantable unit further comprises implant circuitry, and
wherein the one or more processors are configured to drive the first implantable-unit light source to generate the light having the first illumination peak wavelength by transmitting energy to the implant circuitry to activate the first implantable-unit light source to generate the light having the first illumination peak wavelength.

16. The apparatus according to claim 1, wherein the implantable unit is configured to drive the third implantable-unit light source to transmit the optical signal during one or more third time periods non-overlapping with the first and second time periods.

17. A method for detecting a concentration of an analyte in a subject, the method comprising:
implanting, in a body of the subject, an implantable unit, wherein the implantable unit is configured to measure a temperature at the implantable unit, and wherein the implantable unit comprises:
(a) fluorescent sensor molecules, each of which comprises (i) a binding site for the analyte, (ii) a donor fluorophore, and (iii) an acceptor fluorophore;
(b) a first implantable-unit light source that is configured to generate light having a first illumination peak wavelength appropriate for excitation of the donor fluorophore;
(c) a second implantable-unit light source that is configured to generate light having a second illumination peak wavelength appropriate for direct excitation of the acceptor fluorophore;
(d) a third implantable-unit light source configured to emit light having a peak wavelength appropriate for effective penetration through tissue, wherein the implantable unit is configured to use the third implantable-unit light source to transmit an optical signal indicative of the measured temperature, wherein the strength of the optical signal emitted by the third implantable-unit light source does not vary based on a level of the fluorescent sensor molecules or a concentration of the analyte; and
placing an external reading unit of an external system above skin of the subject, wherein the external system includes one or more processors, and wherein the external reading unit comprises a light sensor, which is configured to sense fluorescent light emitted from the acceptor fluorophore, wherein the external system is physically separate and distinct from the implantable unit, and when the external reading unit has been placed above the skin:
(a) during one or more first time periods: (i) driving the first implantable-unit light source to generate the light having the first illumination peak wavelength, and (ii) receiving, from the light sensor, one or more first measurements of the fluorescent light emitted from the acceptor fluorophore,
(b) during one or more second time periods non-overlapping with the first time periods: (i) driving the second implantable-unit light source to generate light having the second illumination peak wavelength appropriate for direct excitation of the acceptor fluorophore, and (ii) receiving, from the light sensor, one or more second measurements of the fluorescent light emitted from the acceptor fluorophore,
(c) during one or more third time periods non-overlapping with the first and second time periods: (i) driving the third implantable-unit light source to generate the optical signal, and (ii) receiving the optical signal generated by the third implantable-unit light source,
(d) generating calibration information using the measured temperature, and
(e) calculating the concentration of the analyte in the subject based on the first and the second measurements and using the calibration information.

18. The method according to claim 17, wherein implanting the implantable unit comprises implanting the implantable unit that:
further comprises implant circuitry, which (a) is configured to generate a train of light pulses using the third implantable-unit light source, and (b) comprises at least one temperature-sensitive element,
is configured such that the at least one temperature-sensitive element causes a change in time between successive light pulses as a function of temperature, and wherein the external system is configured to identify the change in time by analyzing the received optical signal.

\* \* \* \* \*